US011584927B2

(12) United States Patent
Short

(10) Patent No.: US 11,584,927 B2
(45) Date of Patent: *Feb. 21, 2023

(54) CONDITIONALLY ACTIVE CHIMERIC ANTIGEN RECEPTORS FOR MODIFIED T-CELLS

(71) Applicant: BioAtla, Inc., San Diego, CA (US)

(72) Inventor: Jay M. Short, Jackson, WY (US)

(73) Assignee: BioAtla, Inc., San Diego, CA (US)

( * ) Notice: Subject to any disclaimer, the term of this patent is extended or adjusted under 35 U.S.C. 154(b) by 1082 days.

This patent is subject to a terminal disclaimer.

(21) Appl. No.: 16/053,166

(22) Filed: Aug. 2, 2018

(65) Prior Publication Data

US 2018/0340021 A1 Nov. 29, 2018

Related U.S. Application Data

(60) Division of application No. 15/052,487, filed on Feb. 24, 2016, now abandoned, which is a continuation-in-part of application No. PCT/US2015/047197, filed on Aug. 27, 2015.

(60) Provisional application No. 62/043,067, filed on Aug. 28, 2014.

(51) Int. Cl.
| | |
|---|---|
| *C12N 15/10* | (2006.01) |
| *C07K 14/705* | (2006.01) |
| *C07K 14/725* | (2006.01) |
| *C07K 14/735* | (2006.01) |
| *C07K 16/28* | (2006.01) |
| *A61K 39/395* | (2006.01) |
| *C07K 16/18* | (2006.01) |
| *A61K 35/17* | (2015.01) |
| *A61K 38/00* | (2006.01) |
| *A61K 39/00* | (2006.01) |

(52) U.S. Cl.
CPC ...... *C12N 15/1058* (2013.01); *A61K 39/3955* (2013.01); *A61K 39/39558* (2013.01); *C07K 14/705* (2013.01); *C07K 14/7051* (2013.01); *C07K 14/70503* (2013.01); *C07K 14/70521* (2013.01); *C07K 14/70535* (2013.01); *C07K 16/18* (2013.01); *C07K 16/28* (2013.01); *C07K 16/2863* (2013.01); *C12N 15/102* (2013.01); *A61K 35/17* (2013.01); *A61K 38/00* (2013.01); *A61K 2039/5156* (2013.01); *A61K 2039/572* (2013.01); *C07K 2317/31* (2013.01); *C07K 2317/622* (2013.01); *C07K 2317/92* (2013.01); *C07K 2317/94* (2013.01); *C07K 2319/02* (2013.01); *C07K 2319/03* (2013.01)

(58) Field of Classification Search
CPC .............. C12N 15/1058; C12N 15/102; A61K 39/39558; A61K 39/3955; A61K 38/00; A61K 2039/5156; A61K 2039/572; C07K 16/2863; C07K 16/28; C07K 16/18; C07K 14/705; C07K 14/70503; C07K 14/7051; C07K 14/70521; C07K 14/70535; C07K 2317/31; C07K 2317/92; C07K 2317/94; C07K 2319/02; C07K 2310/03

USPC ............... 435/440; 530/387.3, 388.22, 388.8
See application file for complete search history.

(56) References Cited

U.S. PATENT DOCUMENTS

| | | |
|---|---|---|
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |

(Continued)

FOREIGN PATENT DOCUMENTS

| | | |
|---|---|---|
| AU | 2013306390 A1 | 2/2015 |
| EP | 404097 A2 | 12/1990 |

(Continued)

OTHER PUBLICATIONS

Vajdos et al. (2002) J. Mol. Biol., vol. 320, 415-428.*

(Continued)

*Primary Examiner* — Anne Marie S Wehbe
(74) *Attorney, Agent, or Firm* — Mendelsohn Dunleavy, P.C.

(57) ABSTRACT

This disclosure relates to a chimeric antigen receptor for binding with a target antigen. The chimeric antigen receptor comprises at least one antigen specific targeting region including a multispecific antibody evolved from a wild-type antibody or a fragment thereof and having at least one of: (a) a decrease in activity in the assay at the normal physiological condition compared to the wild-type antibody or the fragment thereof, and (b) an increase in activity in the assay under the aberrant condition compared to the wild-type antibody or the fragment thereof. A method for using the chimeric antigen receptor and cytotoxic cells for cancer treatment is also provided. A method for producing the chimeric antigen receptor is also provided.

14 Claims, 16 Drawing Sheets

(15 of 16 Drawing Sheet(s) Filed in Color)

(56) References Cited

U.S. PATENT DOCUMENTS

| | | | |
|---|---|---|---|
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,676,980 A | 6/1987 | Segal et al. |
| 4,683,195 A | 7/1987 | Mullis et al. |
| 4,704,362 A | 11/1987 | Itakura et al. |
| 4,737,456 A | 4/1988 | Weng et al. |
| 4,777,127 A | 10/1988 | Suni et al. |
| 4,797,368 A | 1/1989 | Carter et al. |
| 4,816,567 A | 3/1989 | Cabilly et al. |
| 4,946,778 A | 8/1990 | Ladner et al. |
| 5,139,941 A | 8/1992 | Muzyczka et al. |
| 5,143,854 A | 9/1992 | Pirrung et al. |
| 5,208,020 A | 5/1993 | Chari et al. |
| 5,219,740 A | 6/1993 | Miller et al. |
| 5,362,852 A | 11/1994 | Geoghegan |
| 5,416,064 A | 5/1995 | Chari et al. |
| 5,434,049 A | 7/1995 | Okano et al. |
| 5,500,362 A | 3/1996 | Robinson et al. |
| 5,556,752 A | 9/1996 | Lockhart et al. |
| 5,571,894 A | 11/1996 | Wels et al. |
| 5,587,458 A | 12/1996 | King et al. |
| 5,624,821 A | 4/1997 | Winter et al. |
| 5,632,957 A | 5/1997 | Heller et al. |
| 5,635,483 A | 6/1997 | Pettit et al. |
| 5,641,870 A | 6/1997 | Rinderknecht et al. |
| 5,648,260 A | 7/1997 | Winter et al. |
| 5,663,149 A | 9/1997 | Pettit et al. |
| 5,700,637 A | 12/1997 | Southern |
| 5,712,374 A | 1/1998 | Kunstmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,744,305 A | 4/1998 | Fodor et al. |
| 5,767,237 A | 6/1998 | Sakakibara et al. |
| 5,767,285 A | 6/1998 | Hamann et al. |
| 5,770,456 A | 6/1998 | Holmes |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,800,992 A | 9/1998 | Fodor et al. |
| 5,807,522 A | 9/1998 | Brown et al. |
| 5,821,337 A | 10/1998 | Carter et al. |
| 5,830,645 A | 11/1998 | Pinkel et al. |
| 5,858,358 A | 1/1999 | June et al. |
| 5,866,174 A | 2/1999 | Harada et al. |
| 5,869,046 A | 2/1999 | Presta et al. |
| 5,877,296 A | 3/1999 | Hamann et al. |
| 5,959,098 A | 9/1999 | Goldberg et al. |
| 5,965,452 A | 10/1999 | Kovacs |
| 5,994,136 A | 11/1999 | Naldini et al. |
| 6,013,440 A | 1/2000 | Lipshutz et al. |
| 6,013,516 A | 1/2000 | Verma et al. |
| 6,022,963 A | 2/2000 | McGall et al. |
| 6,045,996 A | 4/2000 | Cronin et al. |
| 6,048,695 A | 4/2000 | Bradley et al. |
| 6,054,270 A | 4/2000 | Southern |
| 6,124,431 A | 9/2000 | Sakakibara et al. |
| 6,171,586 B1 | 1/2001 | Lam et al. |
| 6,194,551 B1 | 2/2001 | Idusogie et al. |
| 6,214,345 B1 | 4/2001 | Firestone et al. |
| 6,248,516 B1 | 6/2001 | Winter et al. |
| 6,258,606 B1 | 7/2001 | Kovacs |
| 6,261,776 B1 | 7/2001 | Pirrung et al. |
| 6,267,958 B1 | 7/2001 | Andya et al. |
| 6,277,489 B1 | 8/2001 | Abbott et al. |
| 6,277,628 B1 | 8/2001 | Johann et al. |
| 6,352,694 B1 | 3/2002 | June et al. |
| 6,441,163 B1 | 8/2002 | Chari et al. |
| 6,534,055 B1 | 3/2003 | June et al. |
| 6,602,684 B1 | 8/2003 | Umana et al. |
| 6,630,579 B2 | 10/2003 | Chari et al. |
| 6,692,964 B1 | 2/2004 | June et al. |
| 6,737,056 B1 | 5/2004 | Presta |
| 6,797,514 B2 | 9/2004 | Berenson et al. |
| 6,867,041 B2 | 3/2005 | Berenson et al. |
| 6,884,799 B2 | 4/2005 | Kamal et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,913,748 B2 | 7/2005 | Widdison |
| 6,985,321 B2 | 1/2006 | Winter |
| 7,048,311 B2 | 5/2006 | Thurston et al. |
| RE39,151 E | 6/2006 | Chari et al. |
| 7,067,318 B2 | 6/2006 | June et al. |
| 7,067,511 B2 | 6/2006 | Thurston et al. |
| 7,087,409 B2 | 8/2006 | Barbas, III et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,265,105 B2 | 9/2007 | Thurston et al. |
| 7,276,497 B2 | 10/2007 | Chari et al. |
| 7,332,581 B2 | 2/2008 | Presta |
| 7,371,826 B2 | 5/2008 | Presta |
| 7,375,078 B2 | 5/2008 | Feng |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,527,791 B2 | 5/2009 | Adams et al. |
| 7,528,126 B2 | 5/2009 | Howard et al. |
| 7,557,099 B2 | 7/2009 | Howard et al. |
| 7,659,241 B2 | 2/2010 | Senter et al. |
| 8,217,149 B2 | 7/2012 | Irving et al. |
| 8,709,755 B2 | 4/2014 | Short et al. |
| 8,853,369 B2 | 10/2014 | Pei et al. |
| 9,388,246 B2 | 7/2016 | Gauthier et al. |
| 9,447,194 B2 | 9/2016 | Jensen |
| 9,683,985 B2 | 6/2017 | Kodandapani et al. |
| 9,902,948 B2 | 2/2018 | Horn |
| 10,513,699 B2 | 12/2019 | Short |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2002/0004587 A1 | 1/2002 | Miller et al. |
| 2002/0164328 A1 | 11/2002 | Shinkawa et al. |
| 2003/0096743 A1 | 5/2003 | Senter et al. |
| 2003/0115614 A1 | 6/2003 | Kanda et al. |
| 2003/0130189 A1 | 7/2003 | Senter et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2005/0260186 A1 | 11/2005 | Bookbinder et al. |
| 2005/0260711 A1 | 11/2005 | Datta et al. |
| 2005/0276812 A1 | 12/2005 | Ebens, Jr. et al. |
| 2006/0025576 A1 | 2/2006 | Miller et al. |
| 2006/0104968 A1 | 5/2006 | Bookbinder et al. |
| 2006/0121005 A1 | 6/2006 | Berenson et al. |
| 2007/0111260 A1 | 5/2007 | Gao et al. |
| 2009/0036431 A1 | 2/2009 | Gauzy et al. |
| 2009/0130718 A1 | 5/2009 | Short |
| 2009/0136950 A1 | 5/2009 | DuBridge et al. |
| 2009/0304710 A1 | 12/2009 | Park et al. |
| 2010/0034837 A1 | 2/2010 | Beria et al. |
| 2010/0047257 A1 | 2/2010 | Blanc et al. |
| 2010/0255004 A1 | 10/2010 | DePinho et al. |
| 2011/0076287 A1 | 3/2011 | Cohen et al. |
| 2011/0256157 A1 | 10/2011 | Howard et al. |
| 2012/0171120 A1 | 7/2012 | Dennis et al. |
| 2013/0203609 A1 | 8/2013 | Horn |

(56) References Cited

U.S. PATENT DOCUMENTS

| | | |
|---|---|---|
| 2013/0266579 A1 | 10/2013 | Wei et al. |
| 2013/0280220 A1 | 10/2013 | Ahmed et al. |
| 2014/0170159 A9 | 6/2014 | Wei et al. |
| 2014/0255363 A1 | 9/2014 | Metelitsa et al. |
| 2014/0271617 A1 | 9/2014 | Igawa et al. |
| 2014/0322234 A1 | 10/2014 | Nusse et al. |
| 2014/0322275 A1 | 10/2014 | Brogdon et al. |
| 2014/0378660 A1 | 12/2014 | Short et al. |
| 2015/0038684 A1 | 2/2015 | Jensen |
| 2015/0071923 A1 | 3/2015 | Wei et al. |
| 2017/0002061 A1 | 1/2017 | Ellmark et al. |
| 2017/0260261 A1 | 9/2017 | Short |
| 2019/0010219 A1 | 1/2019 | Short |
| 2019/0010220 A1 | 1/2019 | Short et al. |

FOREIGN PATENT DOCUMENTS

| | | |
|---|---|---|
| EP | 0425235 A2 | 5/1991 |
| JP | 2012-533307 A | 12/2012 |
| JP | 2013-541940 A | 11/2013 |
| WO | WO8101145 A1 | 4/1981 |
| WO | WO9007936 A1 | 7/1990 |
| WO | WO9102805 A2 | 3/1991 |
| WO | WO9301161 A1 | 1/1993 |
| WO | WO9303769 A1 | 3/1993 |
| WO | WO9308829 A1 | 5/1993 |
| WO | WO9310218 A1 | 5/1993 |
| WO | WO9311230 A1 | 6/1993 |
| WO | WO9316185 A2 | 8/1993 |
| WO | WO9319191 A1 | 9/1993 |
| WO | WO9321232 A1 | 10/1993 |
| WO | WO9322429 A1 | 11/1993 |
| WO | WO9325234 A1 | 12/1993 |
| WO | WO9325698 A1 | 12/1993 |
| WO | WO9403622 A1 | 2/1994 |
| WO | WO9411026 A2 | 5/1994 |
| WO | WO9412649 A1 | 6/1994 |
| WO | WO9428938 A1 | 12/1994 |
| WO | WO9429351 A2 | 12/1994 |
| WO | WO9500655 A1 | 1/1995 |
| WO | WO9511984 A2 | 5/1995 |
| WO | WO9617958 A1 | 6/1996 |
| WO | WO9730087 A1 | 8/1997 |
| WO | WO9746313 A1 | 12/1997 |
| WO | WO9858964 A1 | 12/1998 |
| WO | WO9909217 A1 | 2/1999 |
| WO | WO9922764 A1 | 5/1999 |
| WO | WO9936569 A1 | 7/1999 |
| WO | WO9951642 A1 | 10/1999 |
| WO | WO99951773 A1 | 10/1999 |
| WO | WO0061739 A1 | 10/2000 |
| WO | WO0129246 A1 | 4/2001 |
| WO | WO0231140 A1 | 4/2002 |
| WO | WO02088172 A1 | 11/2002 |
| WO | WO03011878 A2 | 2/2003 |
| WO | WO03026577 A2 | 4/2003 |
| WO | WO03043583 A2 | 5/2003 |
| WO | WO03084570 A1 | 10/2003 |
| WO | WO03085107 A1 | 10/2003 |
| WO | WO03085119 A1 | 10/2003 |
| WO | WO2004008147 A2 | 1/2004 |
| WO | WO2004032828 A2 | 4/2004 |
| WO | WO2004056312 A2 | 7/2004 |
| WO | WO2005035586 A1 | 4/2005 |
| WO | WO2005035778 A1 | 4/2005 |
| WO | WO2005053742 A2 | 6/2005 |
| WO | WO2005100402 A1 | 10/2005 |
| WO | 2006023957 A1 | 3/2006 |
| WO | WO2006029879 A2 | 3/2006 |
| WO | WO2006044908 A2 | 4/2006 |
| WO | WO2007008603 A1 | 1/2007 |
| WO | WO2007008848 A2 | 1/2007 |
| WO | WO2008077546 A1 | 7/2008 |
| WO | WO2009016516 A2 | 2/2009 |
| WO | WO2009062690 A1 | 5/2009 |
| WO | WO2009063965 A1 | 5/2009 |
| WO | WO2009089004 A1 | 7/2009 |
| WO | WO2009099741 A1 | 8/2009 |
| WO | WO2010009124 A2 | 1/2010 |
| WO | WO2010025177 A1 | 3/2010 |
| WO | WO2010104821 A1 | 9/2010 |
| WO | 2011009058 A2 | 1/2011 |
| WO | WO2011014457 A1 | 2/2011 |
| WO | WO2011056983 A1 | 5/2011 |
| WO | WO201109726 A2 | 9/2011 |
| WO | WO2011130598 A1 | 10/2011 |
| WO | WO2011157905 A1 | 12/2011 |
| WO | 2012033953 A1 | 3/2012 |
| WO | WO2012031744 A1 | 3/2012 |
| WO | WO2012099973 A2 | 7/2012 |
| WO | WO2012156747 A1 | 11/2012 |
| WO | WO2013103637 A1 | 7/2013 |
| WO | 2013123061 A | 8/2013 |
| WO | 2013126729 A1 | 8/2013 |
| WO | WO2013126733 A1 | 8/2013 |
| WO | WO2013134743 A1 | 9/2013 |
| WO | WO2013152059 A1 | 10/2013 |
| WO | WO2013170168 A1 | 11/2013 |
| WO | WO2014011993 A2 | 1/2014 |
| WO | 2014039523 A1 | 3/2014 |
| WO | WO2014127261 A1 | 8/2014 |
| WO | 2015028444 A1 | 3/2015 |
| WO | WO2016036916 A1 | 3/2016 |
| WO | WO2016138071 A1 | 9/2016 |
| WO | 2018136570 A1 | 7/2018 |

OTHER PUBLICATIONS

Chen et al. (1992) J. Exp. Med., vol. 176, 855-866.*
Sela-Culang et al. (2013) Frontiers in Immunology, vol. 4, pp. 1-13.*
Raso et al. (1997) J Biol Chem vol. 272:27618-22.*
Gandhi. Master's Theses, U. Rhode Island, 2002.*
Liao et al. (2006) J Virol vol. 80:9599-9607.*
Jensen et al. (2014) Immunol Rev Jan. 2014; 25:127-44.*
Notice of Reasons for Rejection for corresponding Japanese Application No. 2017-511696; dated Jul. 9, 2019.
Decision of Rejection for corresponding Japanese application No. 2018-530483; dated Jul. 21, 2020 (13 pages).
Gerweck, Leo E., et al. "Cellular pH Gradient in Tumor versus Normal Tissue: Potential Exploitation for the Treatment of Cancer." Cancer Research 56.6 (1996): 1194-1198.
Aujla, Amandeep, et al. "Inotuzumab ozogamicin in clinical development for acute lymphoblastic leukemia and non-Hodgkin lymphoma." Biomarker Research 7.9 (2019): 1-10.
Long, Adrienne H., et al. "Lessons learned from a highly-active CD22-specific chimeric antigen receptor." Oncoimmunology 2.4 paper e23621 (2013): 1-3.
Haso, Waleed, et al. "A New High Activity Anti-CD22 Chimeric Antigen Receptor (CAR) Targeting B Cell Leukemia." Abstract, Blood 120.21 (2012): 2611-2611.
Haso, Waleed, et al. "CD22-targeted chimeric antigen receptor (CAR) T cells containing the 4-1BB costimulatory domain demonstrate enhanced persistence and superior efficacy against B-cell precursor acute lymphoblastic leukemia (ALL) compared to those containing CD28." Abstract, Blood 122.21 (2013): 1431-1431.
Pop, Laurentiu M., et al. "A reevaluation of CD22 expression in human lung cancer." Cancer Research 74.1 (2014): 263-271.
Tannock, Ian F., et al. "Acid pH in tumors and its potential for therapeutic exploitation." Cancer Research 49.16 (1989): 4373-4384.
Zhang, Li, et al. "Pluripotent stem cell-derived CAR-macrophage cells with antigen-dependent anti-cancer cell functions." Journal of Hematology & Oncology 13.153 (2020): 1-5.
Non-Final Rejection for U.S. Appl. No. 15/504,470; dated Sep. 8, 2021 (55 pages).
Notice of Rejection for Japanese application No. 2018-530483; dated Sep. 28, 2021 (27 pages).
Office Action for Canadian application No. 2,959,141; dated Sep. 14, 2021 (7 pages).

(56) References Cited

OTHER PUBLICATIONS

1st Substantive Examination for Mexican application No. MX/a/2017/002605; dated Sep. 15, 2020 (8 pages).
Communication pursuant to Article 94(3) EPC for European application No. 15836397.8; dated Sep. 16, 2020 (4 pages).
Faes, Seraina, et al. "Acidic pH reduces VEGF-mediated endothelial cell responses by downregulation of VEGFR-2; relevance for anti-angiogenic therapies." Oncotarget 7.52 (2016): 86026.
Non-Final Office Action; dated Sep. 18, 2018 for U.S. Appl. No. 15/504,470.
Bedzyk, William D., et al. "Immunological and structural characterization of a high affinity anti-fluorescein single-chain antibody." Journal of biological chemistry 265.30 (1990): 18615-18620.
Caldwell, Charles R., and Carol E. Whitman. "Temperature-induced protein conformational changes in barley root plasma membrane-enriched microsomes I. Effect of temperature on membrane protein and lipid mobility." Plant physiology 84.3 (1987): 918-923.
Cartellieri, Marc, et al. "Chimeric antigen receptor-engineered T cells for immunotherapy of cancer." BioMed Research International 2010 (2010).
Chaudhary, Vijay K., et al. "A recombinant single-chain immunotoxin composed of anti-Tac variable regions and a truncated diphtheria toxin." Proceedings of the National Academy of Sciences 87.23 (1990): 9491-9494.
Di Russo, Natali V., et al. "pH-Dependent Conformational Changes in Proteins and Their Effect on Experimental pK as: The Case of Nitrophorin 4." PLoS Comput Biol 8.11 (2012): e1002761.
Estrella, Veronica, et al. "Acidity generated by the tumor microenvironment drives local invasion." Cancer research 73.5 (2013): 1524-1535.
Gandhi, Sejal. "Effect of PH and Temperature on Conformational Changes of a Humanized Monoclonal Antibody." (2002).
Grada, Zakaria, et al. "TanCAR: a novel bispecific chimeric antigen receptor for cancer immunotherapy." Molecular Therapy—Nucleic Acids 2.7 (2013): e105.
Hudecek, Michael, et al. "The non-signaling extracellular spacer domain of chimeric antigen receptors is decisive for in vivo antitumor activity." Cancer immunology research (2014): canimm-0127.
Inaguma, Y., et al. "Construction and molecular characterization of a T-cell receptor-like antibody and CAR-T cells specific for minor histocompatibility antigen HA-1H." Gene Therapy 21.6 (2014): 575-584.
Jensen, Michael C., and Stanley R. Riddell. "Design and implementation of adoptive therapy with chimeric antigen receptor-modified T cells." Immunological reviews 257.1 (2014): 127-144.
Ma, Jennifer SY, et al. "Versatile strategy for controlling the specificity and activity of engineered T cells." Proceedings of the National Academy of Sciences (2016): 201524193.
Rothe, Achim, et al. "A phase 1 study of the bispecific anti-CD30/CD16A antibody construct AFM13 in patients with relapsed or refractory Hodgkin lymphoma." Blood 125.26 (2015): 4024-4031.
Xiong, Cheng-Yi, et al. "Development of tumor targeting anti-MUC-1 multimer: effects of di-scFv unpaired cysteine location on PEGylation and tumor binding." Protein Engineering Design and Selection 19.8 (2006): 359-367.
European Search Report; dated Jan. 2, 2018 for EP Application No. EP15836397.8.
Kong, Seogkyoung, et al. "Suppression of human glioma xenografts with second-generation IL13R-specific chimeric antigen receptor-modified T cells." Clinical Cancer Research 18.21 (2012): 5949-5960.
Pirooznia, Nazanin, et al. "The construction of chimeric T-Cell receptor with spacer base of modeling study of VHH and MUC1 interaction." Journal of BioMed Research 2011 (2011).
Sadelain, Michel, Renier Brentjens, and Isabelle Rivière. "The basic principles of chimeric antigen receptor design." Cancer discovery 3.4 (2013): 388-398.
International Search Report; dated Jun. 1, 2016 for PCT Application No. PCT/US2016/019255.

Restriction Requirement; dated Jun. 9, 2017 for U.S. Appl. No. 15/052,487.
Non-Final Office Action; dated Oct. 12, 2017 for U.S. Appl. No. 15/052,487.
Final Office Action; dated Apr. 4, 2018 for U.S. Appl. No. 15/052,487.
Justus, C., et al. "Acidic tumor microenvironment and pH-sensing G protein-coupled receptors." Frontiers in physiology 4 (2013): 354.
Liao, M., et al. "Site-directed antibodies against the stem region reveal low pH-induced conformational changes of the Semliki Forest virus fusion protein." Journal of virology 80.19 (2006): 9599-9607.
Raso, Vic, et al. "Antibodies capable of releasing diphtheria toxin in response to the low pH found in endosomes." Journal of Biological Chemistry 272.44 (1997): 27618-27622.
Extended European Search Report; dated Feb. 20, 2019 for EP Application No. 16839728.9.
Miao, H., et al. "EGFRvIII-Specific Chimeric Antigen Receptor T Cells Migrate to and Kill Tumor." (2014), pp. 1-9.
EP Office Action; dated Nov. 12, 2018 for EP Application No. 15 836 397.8.
Official Notification for Russian application No. 2018110553; dated Nov. 29, 2019 (8 pages).
Non-Final Rejection for U.S. Appl. No. 15/753,872; dated Dec. 23, 2019 (47 pages).
Notice of Reasons for Rejection for Japanese application No. 2018-530483; dated Nov. 19, 2019 (7 pages).
Han, Jianfeng, et al. "CAR-Engineered NK Cells Targeting Wild-Type EGFR and EGFRvIII Enhance Killing of Glioblastoma and Patient-Derived Glioblastoma Stem Cells." Scientific Reports 5 (2015): 11483. (13 pages).
Almagro, Juan C. et al., "Humanization of Antibodies." Frontiers in Bioscience 13 (2008): 1619-1633.
Jena, B. et al. (2010). "Redirecting T-cell specificity by introducing a tumor-specific chimeric antigen receptor." Blood, The Journal of the American Society of Hematology 116.7 (2010): 1035-1044.
Maetzig, Tobias, et al. "Gammaretroviral Vectors: Biology, Technology and Application." Viruses 3.6 (2011): 677-713.
Malik, A. K. et al., "Effects of a second intron on recombinant MFG retroviral vector." Archives of Virology 146.3 (2001): 601-609.
Non-Final Rejection for corresponding U.S. Appl. No. 15/753,872; dated May 14, 2020 (44 pages).
International Search Report and Written Opinion for corresponding International application No. PCT/US2019/047848 dated Feb. 25, 2020 (11 pages).
Communication pursuant to Article 94(3) EPC for corresponding European application No. 16839728.9; dated May 15, 2020 (4 pages).
Examination Report No. 1 for corresponding Australian application No. 2015308818; dated May 1, 2020 (4 pages).
Non-Final Office Action for corresponding U.S. Appl. No. 15/504,470; dated Jul. 30, 2020 (49 pages).
Bridgeman, John S., et al. "The Optimal Antigen Response of Chimeric Antigen Receptors Harboring The Cd3 ζ Transmembrane Domain Is Dependent upon Incorporation of the Receptor into the Endogenous TCR/CD3 Complex." The Journal of Immunology 184.12 (2010): 6938-6949.
Bumbaca, Daniela et al. "Highly specific off-target binding identified and eliminated during the humanization of an antibody against FGF receptor 4" mAbs 3.4 (2011): 376-386.
Devanaboyina, Siva Charan et al. "The effect of pH dependence of antibody-antigen interactions on subcellular trafficking dynamics" mAbs 5.6 (2013): 851-859.
Daugherty, Patrick S. et al. "Quantitative analysis of the effect of the mutation frequency on the affinity mutation of single chain Fv antibodies" Proceedings of the National Academy of Sciences 97.5 (2000): 2029-2034.
Ducancel, Frédéric et al. "Molecular engineering of antibodies for therapeutic and diagnostic purposes" mAbs 4.4 (2012): 445-457.
Haso, Waleed et al. "Anti-CD22-chimeric antigen receptors targeting B-cell precursor acute lymphoblastic leukemia." Blood 121.7 (2013): 1165-1174.

(56) References Cited

OTHER PUBLICATIONS

Ho, Mitchell et al. "In Vitro Antibody Evolution Targeting Germline Hot Spots to Increase Activity of an Anti-CD22 Immunotoxin" The Journal of Biological Chemistry 280.1 (2005): 607-617.

Hudecek, Michael, et al. "Receptor affinity and extracellular domain modifications affect tumor recognition by ROR1-specific chimeric antigen receptor T cells." Clinical Cancer Research 19.12 (2013): 3153-3164.

Igawa, Tomoyuki, et al. "Antibody recycling by engineered pH-dependent antigen binding improves the duration of antigen neutralization." Nature Biotechnology 28.11 (2010): 1203-1207.

Igawa, Tomoyuki, et al. "Engineering the variable region of therapeutic IgG antibodies." MAbs. vol. 3. No. 3. Taylor & Francis (2011): 243-252.

Jellusova, Julia, and Lars Nitschke. "Regulation of B cell functions by the sialic acid-binding receptors siglec-G and CD22." Frontiers in Immunology 2.96 (2012): (14 pages).

Song, Chang W., et al. "Influence of tumor pH on therapeutic response." Cancer Drug Resistance. Humana Press, (2006): 21-42.

Vincent, Karen J., et al. "Current strategies in antibody engineering: Fc engineering and pH-dependent antigen binding bispecific antibodies and antibody drug conjugates." Biotechnology Journal 7.12 (2012): 1444-1450.

Examination Report for Indian application No. 201717006622; dated Jul. 6, 2021 (7 pages).

Examination Report No. 2 for Australian application No. 2016313107; dated Nov. 18, 2020 (5 pages).

First Office Action for Chinese application No. 201680049877.7; dated Jan. 28, 2021 (26 pages).

Final Office Action for U.S. Appl. No. 15/504,470; dated Jan. 13, 2021 (50 pages).

Non-Final Office Action for U.S. Appl. No. 16/125,302; dated Jan. 14, 2021 (18 pages).

Shirmanova, Marina V., et al. "Intracellular pH imaging in cancer cells in vitro and tumors in vivo using the new genetically encoded sensor SypHer2." Biochimica et Biophysica Acta 1850.9 (2015): 1905-1911.

Final Office Action for U.S. Appl. No. 15/504,470 dated Apr. 16, 2019.

Reconsideration Report for Japanese application No. 2018-530483; dated Feb. 26, 2021 (6 pages).

Results of Test of Invention for Patentability for Russian application No. 2018110553; dated Feb. 17, 2021 (20 pages).

Second Office Action for Chinese application No. 201580057728.0; dated May 8, 2021 (19 pages) Machine Translation.

Ramos, Carlos A., et al. "CAR-T Cell Therapy for Lymphoma." Annual Review of Medicine 67 (2016): 165-183.

Newick, Kheng et al. "Chimeric antigen receptor T-cell therapy for solid tumors." Molecular Therapy-Oncolytics 3 (2016): 16006. (7 pages).

Notice of Reasons for Rejection for corresponding Japanese application No. 2017-511696; dated Jun. 2, 2020 (8 pages).

First Office Action for corresponding Chinese application No. 201580057728.0; dated Jun. 10, 2020 (18 pages).

He, Xi et al., "pH-sensitive drug-delivery systems for tumor targeting." Therapeutic Delivery 4.12 (2013): 1499-1510.

Igawa, T. et al., "pH-dependent antigen-binding antibodies as a novel therapeutic modality." Biochimica et Biophysica Acta (BBA)-Proteins and Proteomics 1844.11 (2014): 1943-1950.

Official Notification for corresponding Russian Application No. 2017109966; dated Sep. 6, 2019—Machine Translation.

Reverberi, Roberto et al. "Factors Affecting the Antigen-antibody Reaction." Blood Transfusion 5.4 (2007): 227-240.

Search Report and Written Opinion for corresponding Brazilian application No. BR112017003835; dated Sep. 23, 2020 (6 pages).

Search Report and Written Opinion for corresponding Brazilian application No. BR112018003535; dated Oct. 14, 2020 (7 pages).

Official Action of the Substantive Examination for Russian Application No. 2018110553; dated Jun. 28, 2019.

Kunii, Naoki, et al. "Enhanced function of redirected human T cells expressing linker for activation of T cells that is resistant to ubiquitylation." Human gene therapy 24.1 (2013): 27-37.

Russian Office Action; dated Mar. 11, 2019 for RU Application No. 2017109966.

Jäckel, C., et al. "Protein design by directed evolution." Annu. Rev. Biophys. 37 (2008): 153-173.

Kam, Nadine Wong Shi, et al. "Carbon nanotubes as multifunctional biological transporters and near-infrared agents for selective cancer cell destruction." Proceedings of the National Academy of Sciences of the United States of America 102.33 (2005): 11600-11605.

Morrison, Sherie L., et al. "Chimeric human antibody molecules: mouse antigen-binding domains with human constant region domains." Proceedings of the National Academy of Sciences 81.21 (1984): 6851-6855.

Hellström, Ingegerd, Vera Brankovan, and K. E. Hellström. "Strong antitumor activities of IgG3 antibodies to a human melanoma-associated ganglioside." Proceedings of the National Academy of Sciences 82.5 (1985): 1499-1502.

Hellström, Ingegerd, Paul L Beaumier, and Karl Erik Hellström. "Antitumor effects of L6, an IgG2a antibody that reacts with most human carcinomas." Proceedings of the National Academy of Sciences 83.18 (1986): 7059-7063.

Chothia, Cyrus, and Arthur M. Lesk. "Canonical structures for the hypervariable regions of immunoglobulins" Journal of molecular biology 196.4 (1987): 901-917.

Brüggemann, M., et al. "Comparison of the effector functions of human immunoglobulins using a matched set of chimeric antibodies." The Journal of experimental medicine 166.5 (1987): 1351-1361.

Presta, Leonard G., et al. "Humanization of an anti-vascular endothelial growth factor monoclonal antibody for the therapy of solid tumors and other disorders." Cancer research 57.20 (1997): 4593-4599.

Queen, Cary, et al. "A humanized antibody that binds to the interleukin 2 receptor." Proceedings of the National Academy of Sciences 86.24 (1989): 10029-10033.

Carter, Paul, et al. "Humanization of an anti-p185HER2 antibody for human cancer therapy." Proceedings of the National Academy of Sciences 89.10 (1992): 4285-4289.

Hinman, Lois M., et al. "Preparation and characterization of monoclonal antibody conjugates of the calicheamicins: a novel and potent family of antitumor antibiotics." Cancer research 53.14 (1993): 3336-3342.

Rodrigues, Maria L., et al. "Synthesis and β-lactamase-mediated activation of a cephalosporin-taxol prodrug." Chemistry & biology 2.4 (1995): 223-227.

Rosok, Mae Joanne, et al. "A combinatorial library strategy for the rapid humanization of anticarcinoma BR96 Fab." Journal of Biological Chemistry 271.37 (1996): 22611-22618.

Liu, Changnian, et al. "Eradication of large colon tumor xenografts by targeted delivery of maytansinoids." Proceedings of the National Academy of Sciences 93.16 (1996): 8618-8623.

Baca, Manuel, et al. "Antibody humanization using monovalent phage display." Journal of Biological Chemistry 272.16 (1997): 10678-10684.

Clynes, Raphael, et al. "Fc receptors are required in passive and active immunity to melanoma." Proceedings of the National Academy of Sciences 95.2 (1998): 652-656.

Lode, Holger N., et al. "Targeted Therapy with a Novel Enediyene Antibiotic Calicheamicin ϑI1 Effectively Suppresses Growth and Dissemination of Liver Metastases in a Syngeneic Model of Murine Neuroblastoma." Cancer research 58.14 (1998): 2925-2928.

Pettit, Robin K., George R. Pettit, and Kevin C. Hazen. "Specific activities of dolastatin 10 and peptide derivatives against Cryptococcus neoformans" Antimicrobial agents and chemotherapy 42.11 (1998): 2961-2965.

Chen, Yvonne, et al. "Selection and analysis of an optimized anti-VEGF antibody: crystal structure of an affinity-matured Fab in complex with antigen" Journal of molecular biology 293.4 (1999): 865-881.

Nagy, Attila, Artur Plonowski, and Andrew V. Schally. "Stability of cytotoxic luteinizing hormone-releasing hormone conjugate (AN-152) containing doxorubicin 14-O-hemiglutarate in mouse and

(56) References Cited

OTHER PUBLICATIONS human serum in vitro: implications for the design of preclinical studies." Proceedings of the National Academy of Sciences 97.2 (2000): 829-834.
Klimka, A., et al. "Human anti-CD30 recombinant antibodies by guided phage antibody selection using cell panning." British journal of cancer 83.2 (2000): 252.
Hay, Michael P., et al. "A 2-nitroimidazole carbamate prodrug of 5-amino-1-(chloromethyl)-3-[(5, 6, 7-trimethoxyindol-2-yl) carbonyl]-1,2-dihydro-3H-benz [e] indole (amino-seco-CBI-TMI) for use with ADEPT and GDEPT." Bioorganic & medicinal chemistry letters 9.15 (1999): 2237-2242.
Saleh, Mansoor N., et al. "Phase I Trial of the Anti-Lewis Y Drug Immunoconjugate BR96-Doxorubicin in Patients With Lewis Y-Expressing Epithelial Tumors." Journal of Clinical Oncology 18.11 (2000): 2282-2292.
Idusogie, Esohe E., et al. "Mapping of the C1q binding site on rituxan, a chimeric antibody with a human IgG1 Fc." The Journal of Immunology 164.8 (2000): 4178-4184.
Woyke, Tanja, et al. "In vitro activities and postantifungal effects of the potent dolastatin 10 derivative auristatin PHE." Antimicrobial agents and chemotherapy 45.12 (2001): 3580-3584. 25.
Shields, Robert L., et al. "High resolution mapping of the binding site on human IgG1 for FcγRI, FcγRII, FcγRIII, and FcRn and design of IgG1 variants with improved binding to the FcγR." Journal of Biological Chemistry 276.9 (2001): 6591-6604.
Yu, Tin-Wein, et al. "The biosynthetic gene cluster of the maytansinoid antitumor agent ansamitocin from Actinosynnema pretiosum." Proceedings of the National Academy of Sciences 99.12 (2002): 7968-7973.
Gillies, Robert J., et al. "MRI of the tumor microenvironment." Journal of Magnetic Resonance Imaging 16.4 (2002): 430-450.
Hudson, Peter J., and Christelle Souriau. "Engineered antibodies." Nature medicine 9.1 (2003): 129-134.
Cragg, Mark S., et al. "Complement-mediated lysis by anti-CD20 mAb correlates with segregation into lipid rafts." Blood 101.3 (2003): 1045-1052.
Doronina, Svetlana O., et al. "Development of potent monoclonal antibody auristatin conjugates for cancer therapy." Nature biotechnology 21.7 (2003): 778-784.
Francisco, Joseph A., et al. "cAC10-vcMMAE, an anti-CD30-monomethyl auristatin E conjugate with potent and selective antitumor activity." Blood 102.4 (2003): 1458-1465.
Osbourn, Jane, Maria Groves, and Tristan Vaughan. "From rodent reagents to human therapeutics using antibody guided selection " Methods 36.1 (2005): 61-68.
Kashmiri, Syed VS, et al. "SDR grafting—a new approach to antibody humanization." Methods 36.1 (2005): 25-34.
Cragg, Mark S., and Martin J. Glennie. "Antibody specificity controls in vivo effector mechanisms of anti-CD20 reagents." Blood 103.7 (2004): 2738-2743.
Dall'Acqua, William F., et al. "Antibody humanization by framework shuffling." Methods 36.1 (2005): 43-60.
Petkova, Stefka B., et al. "Enhanced half-life of genetically engineered human IgG1 antibodies in a humanized FcRn mouse model: potential application in humorally mediated autoimmune disease." International immunology 18.12 (2006): 1759-1769.
Kratz, Felix, et al. "Prodrugs of anthracyclines in cancer chemotherapy." Current medicinal chemistry 13.5 (2006): 477-523.
Flatman, Stephen, et al. "Process analytics for purification of monoclonal antibodies." Journal of Chromatography B 848.1 (2007): 79-87.
Henry, C. et al., "Targeting the ROR1 and ROR2 receptors in epithelial ovarian cancer inhibits cell migration and invasion" Oncotarget, Oct. 20, 2015, vol. 6, No. 37, pp. 40310-40326.
Minami, Yasuhiro, et al. "Ror-family receptor tyrosine kinases in noncanonical Wnt signaling: Their implications in developmental morphogenesis and human diseases." Developmental Dynamics 239.1 (2010): 1-15.

Ford, Caroline E., et al. "The dual role of the novel Wnt receptor tyrosine kinase, ROR2, in human carcinogenesis." International journal of cancer 133.4 (2013): 779-787.
Chang, C. et al., "Novel conditionally active biologic anti-Axl antibody-drug conjugate demonstrates anti-tumor efficacy and improved safety profile". AACR Annual Meeting. April 16-20, 2016; New Orleans. USA—Presentation Abstract 3836.
Debebe, Zufan, et al. "Ror2 as a Therapeutic Target in Cancer." Pharmacology & Therapeutics 150 (2015): 143-148.
Knappik Achim, et al. "Fully synthetic human combinatorial antibody libraries (HuCAL) based on modular consensus frameworks and CDRs randomized with trinucleotides." Journal of Molecular Biology 296.1 (2000): 57-86.
Rabia, Lilia A., et al. "Understanding and overcoming trade-offs between antibody affinity, specificity, stability and solubility." Biochemical Engineering Journal 137 (2018): 365-374.
Rudikoff, Stuart, et al. "Single amino acid substitution altering antigen-binding specificity." Proceedings of the National Academy of Sciences 79.6 (1982): 1979-1983.
Edris, Badreddin, et al. "ROR2 is a novel prognostic biomarker and a potential therapeutic target in leiomyosarcoma and gastrointestinal stromal tumour." The Journal of Pathology 227.2 (2012): 223-233.
Zhang, Jie, et al. "Wnt5a signaling pathway and its role in cell motility." Chinese Bulletin of Life Sciences 25.3 (2013): 289-294 (Machine Translation).
Decision of Rejection for Chinese application No. 201580057728.0; dated May 7, 2022 (15 pages).
Cho, Jang Hwan, et al. "Engineering Axl specific CAR and Syn-Notch receptor for cancer therapy." Scientific Reports 8.1 (2018): 1-8.
Extended European Search Report for European application No. 19856976.6; dated May 10, 2022 (13 pages).
Nerreter, T., et al. "ROR2 is a novel target for CAR T cells in breast cancer." Oncology Research and Treatment 40.3 (2017): p. 130 (abstract).
Wei, Jing, et al. "A novel AXL chimeric antigen receptor endows T cells with anti-tumor effects against triple negative breast cancers." Cellular Immunology 331 (2018): 49-58.
Third Office Action for corresponding Chinese application No. 201580057728.0; dated Dec. 3, 2021 (8 pages).
3rd Substantive Examination for corresponding Mexican application No. MX/a/2017/002605; dated Nov. 10, 2021 (6 pages).
1st Substantive Examination for Mexican application No. MX/a/2018/002400; dated Jan. 11, 2022 (9 pages).
Office Action for Canadian application No. 2,996,514; dated Feb. 2, 2022 (6 pages).
Examination Report for Indian application No. 201817005998; dated Feb. 21, 2022 (6 pages).
Notice of Reasons for Refusal for Japanese application No. 2021-082062; dated Feb. 22, 2022 (4 pages) Machine Translation.
Final Office Action for U.S. Appl. No. 15/504,470; dated Mar. 15, 2022 (53 pages).
Petrova, Tatiana V., et al. "VEGFR-3 expression is restricted to blood and lymphatic vessels in solid tumors." Cancer Cell 13.6 (2008): 554-556.
Wang, W., et al. "Specificity redirection by CAR with human VEGFR-1 affinity endows T lymphocytes with tumor-killing ability and anti-angiogenic potency." Gene Therapy 20.10 (2013): 970-978.
Zhao, Yangbing, et al. "A herceptin-based chimeric antigen receptor with modified signaling domains leads to enhanced survival of transduced T lymphocytes and antitumor activity." The Journal of Immunology 183.9 (2009): 5563-5574.
Office Action for corresponding Canadian application No. 2,959,141; dated Aug. 3, 2022 (6 pages).
Notice of Reasons for Rejection for Japanese application No. 2017-511696; dated Jul. 5, 2022 (21 pages).
Extended European Search Report and Written Opinion for European application No. 22164162.4; dated Sep. 15, 2022 (5 pages).
Request for Submission of Opinion for Korean application No. 10-2017-7006675; dated Sep. 6, 2022 (10 pages) Machine Translation.

\* cited by examiner

CONDITIONALLY ACTIVE CHIMERIC ANTIGEN RECEPTORS FOR MODIFIED T-CELLS

RELATED APPLICATION DATA

This application is a divisional of U.S. application Ser. No. 15/052,487, filed Feb. 24, 2016 which, in turn, is a continuation-in-part of International Application No. PCT/US15/47197, filed Aug. 27, 2015, which, in turn claims benefit to U.S. Provisional Application No. 62/043,067, filed Aug. 28, 2014, which applications are hereby incorporated by reference in their entirety.

FIELD OF THE DISCLOSURE

This disclosure relates to the field of protein evolution. Specifically, this disclosure relates to a method of generating a conditionally active chimeric antigen receptor from a wild type protein. The conditionally active chimeric antigen receptor is reversibly or irreversibly inactivated at a wild type normal physiological condition, but is active at an aberrant condition.

BACKGROUND OF THE DISCLOSURE

There is a considerable body of literature describing the potential for evolving proteins for a variety of characteristics, especially enzymes. For example, enzymes may be evolved to be stabilized for operation at different conditions such as at an elevated temperature. In situations where there is an activity improvement at the elevated temperature, a substantial portion of the improvement can be attributed to the higher kinetic activity commonly described by the Q10 rule where it is estimated that in the case of an enzyme the turnover doubles for every increase of 10 degrees Celsius.

In addition, there exist examples of natural mutations that destabilize proteins at their normal operating conditions. Certain mutants can be active at a lower temperature, but at a reduced level compared to the wild type proteins. This is also typically described by a reduction in activity as guided by the Q10 or similar rules.

It is desirable to generate useful molecules that are conditionally activated. For example, it is desirable to generate molecules that are virtually inactive at wild-type operating conditions but are active at other than wild-type operating conditions at a level that is equal to or better than at wild-type operating conditions, or that are activated or inactivated in certain microenvironments, or that are activated or inactivated over time. Besides temperature, other conditions for which the proteins can be evolved or optimized include pH, osmotic pressure, osmolality, oxidative stress and electrolyte concentration. Other desirable properties that can be optimized during evolution include chemical resistance, and proteolytic resistance.

Many strategies for evolving or engineering molecules have been published. However, engineering or evolving a protein to be inactive or virtually inactive (less than 10% activity and preferably less than 1% activity) at a wild type operating condition, while maintaining activity equivalent or better than its corresponding wild type protein at a condition other than a wild-type operating condition, requires that destabilizing mutation(s) co-exist with activity increasing mutations that do not counter the destabilizing effect. It is expected that destabilization would reduce the protein's activity greater than the effects predicted by standard rules such as Q10. Therefore, the ability to evolve proteins that work efficiently at lower temperature, for example, while being inactivated under the normal operating condition for the corresponding wild-type protein, creates an unexpected new class of proteins.

Chimeric antigen receptors (CARs) have been used in treating cancers. US 2013/0280220 discloses methods and compositions providing improved cells encoding a chimeric antigen receptor that is specific for two or more antigens, including tumor antigens. Cells expressing the chimeric antigen receptor may be used in cell therapy. Such cell therapy may be suitable for any medical condition, although in specific embodiments the cell therapy is for cancer, including cancer involving solid tumors.

The present invention provides engineered conditionally active chimeric antigen receptors that are inactive or less active at a normal physiological condition but active at an aberrant physiological condition.

Throughout this application, various publications are referenced by author and date. The disclosures of these publications are hereby incorporated by reference in their entireties into this application in order to more fully describe the state of the art as known to those skilled therein as of the date of the disclosure described and claimed herein.

BRIEF DESCRIPTION OF THE DRAWINGS

The application file contains at least one drawing executed in color. Copies of this patent application publication with color drawings will be provided by the Office upon request and payment of the necessary fee.

SUMMARY OF THE DISCLOSURE

Figure 1:
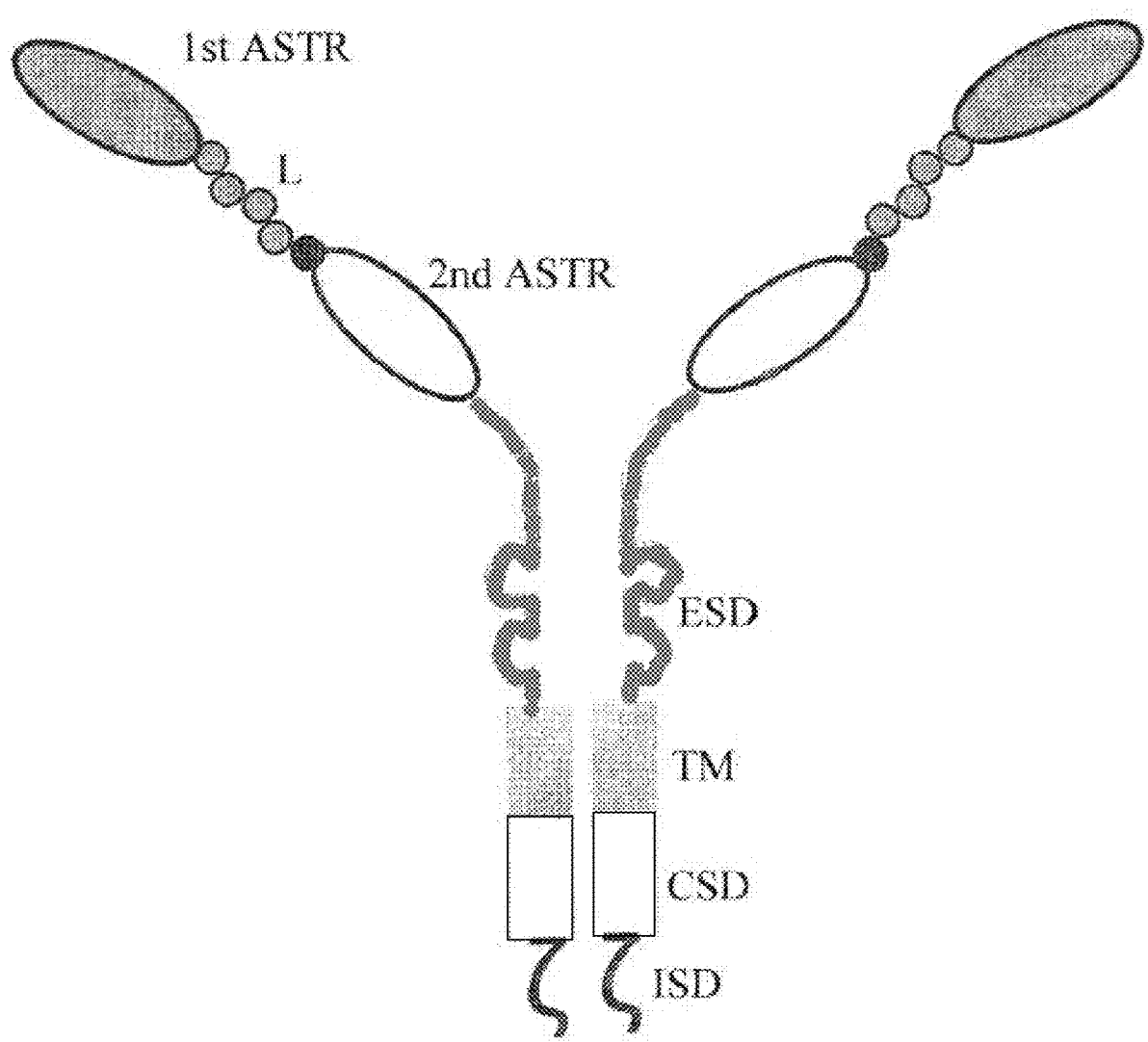
FIG. 1 depicts a schematic representation of a chimeric antigen receptor in accordance with one embodiment of the present invention. ASTR is an antigen-specific targeting region, L is a linker, ESD is an extracellular spacer domain, TM is a transmembrane domain, CSD is a co-stimulatory domain, and ISD is an intracellular signaling domain.

In one aspect, the present invention provides a chimeric antigen receptor (CAR) for binding with a target antigen. The chimeric antigen receptor comprises at least one antigen specific targeting region that is evolved from a wild-type protein or a domain thereof. The CAR further comprises a transmembrane domain and an intracellular signaling domain. The at least one antigen specific targeting region has at least one of: (a) a decrease in activity in an assay at the normal physiological condition compared to the antigen specific targeting region of the wild-type protein or a domain thereof, and (b) an increase in activity in an assay under the aberrant condition compared to the antigen specific targeting region of the wild-type protein or a domain thereof.

In another aspect, the present invention provides an expression vector, including a polynucleotide sequence encoding the chimeric antigen receptor of the invention. The expression vector is selected from lentivirus vectors, gamma retrovirus vectors, foamy virus vectors, adeno associated virus vectors, adenovirus vectors, pox virus vectors, herpes virus vectors, engineered hybrid viruses, and transposon mediated vectors.

In yet another aspect, the present invention provides a genetically engineered cytotoxic cell that includes a polynucleotide sequence encoding the chimeric antigen receptor of the invention. The cytotoxic cell may be a T cell and may be selected from a naive T cell, a central memory T cell, and an effector memory T cell.

In yet another aspect, the present invention provides a pharmaceutical composition, including the chimeric antigen receptor, the expression vector, and/or the genetically engineered cytotoxic cell of the invention, and a pharmaceutically acceptable excipient.

In yet another aspect, the present invention provides a method for treating a cancer in a subject, including the step of introducing an expression vector including a polynucleotide sequence encoding the chimeric antigen receptor of the invention into a cytotoxic cell obtained from the subject to produce a genetically engineered cytotoxic cell; and administering the genetically engineered cytotoxic cell to the subject.

In yet another aspect, the present invention provides a method for producing a chimeric antigen receptor comprising at least one antigen specific targeting region, a transmembrane domain and an intracellular signaling domain. The method comprising the steps of generating the at least one antigen specific targeting region from a wild-type protein or a domain thereof that binds specifically with a target antigen. These steps include (i) evolving the DNA which encodes the wild-type protein or a domain thereof using one or more evolutionary techniques to create mutant DNAs; (ii) expressing the mutant DNAs to obtain mutant polypeptides; (iii) subjecting the mutant polypeptides and the wild-type protein or a domain thereof to an assay under a normal physiological condition and to an assay under an aberrant condition; and (iv) selecting a conditionally active antigen specific targeting region from the mutant polypeptides expressed in step (iii) which exhibits at least one of (a) a decrease in activity in the assay at the normal physiological condition compared to the antigen specific targeting region of the wild-type protein or a domain thereof, and (b) an increase in activity in the assay under the aberrant condition compared to the antigen specific targeting region of the wild-type protein or a domain thereof.

[1] A chimeric antigen receptor for binding with a target antigen. The chimeric antigen receptor comprises at least two antigen specific targeting regions connected by a conditional linker. The conditional linker has a first conformation at an aberrant condition for the at least two antigen specific targeting regions to bind to the target antigen at a higher binding activity than a binding activity of a second conformation of the conditional linker at a normal physiological condition. The chimeric antigen receptor further comprises a transmembrane domain and an intracellular signaling domain.

[2] A chimeric antigen receptor for binding with a target antigen. The chimeric antigen receptor comprises at least one antigen specific targeting region that binds with the target antigen, a transmembrane domain and an intracellular signaling domain. The chimeric antigen receptor further comprises an extracellular spacer domain having a first conformation at an aberrant condition for the at least one antigen specific targeting region to bind to the target antigen at a higher binding activity than a binding activity of a second conformation of a second conformation of the extracellular spacer domain at a normal physiological condition.

[3] A chimeric antigen receptor for binding with a target antigen. The chimeric antigen receptor comprises at least one antigen specific targeting region that binds with the target antigen, a transmembrane domain and an intracellular signaling domain. The chimeric antigen receptor further comprises an extracellular spacer domain having an enhanced ubiquitylation-resistance level at an aberrant condition than at a normal physiological condition.

[4] The chimeric antigen receptor of [1-3], wherein the antigen specific targeting region is evolved from a wild-type protein or a domain thereof and having at least one of: (a) a decrease in activity in an assay at the normal physiological condition compared to the antigen specific targeting region of the wild-type protein or a domain thereof, and (b) an increase in activity in an assay under the aberrant condition compared to the antigen specific targeting region of the wild-type protein or a domain thereof.

Definitions

In order to facilitate understanding of the examples provided herein, certain frequently occurring methods and/or terms will be defined herein.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

The term "agent" is used herein to denote a chemical compound, a mixture of chemical compounds, an array of spatially localized compounds (e.g., a VLSIPS peptide array, polynucleotide array, and/or combinatorial small molecule array), biological macromolecule, a bacteriophage peptide display library, a bacteriophage antibody (e.g., scFv) display library, a polysome peptide display library, or an extract made from biological materials such as bacteria, plants, fungi, or animal (particular mammalian) cells or tissues. Agents are evaluated for potential enzyme activity by inclusion in screening assays described herein below. Agents are evaluated for potential activity as conditionally active biologic therapeutic enzymes by inclusion in screening assays described herein below.

The term "amino acid" as used herein refers to any organic compound that contains an amino group (—NH$_2$) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "amplification" as used herein means that the number of copies of a polynucleotide is increased.

The term "antibody" as used herein refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "antigen" or "Ag" as used herein is defined as a molecule that provokes an immune response. This immune response may involve either antibody production, or the activation of specific immunologically-competent cells, or both. A person skilled in the art will understand that any macromolecule, including virtually all proteins or peptides, can serve as an antigen. Furthermore, antigens can be derived from recombinant or genomic DNA. A person skilled in the art will understand that any DNA, which includes a nucleotide sequence or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled person will understand that an antigen need not be encoded by a "gene" at all. It is readily apparent that an antigen can be generated, synthesized or can be derived from a biological sample. Such a biological sample can include, but is not limited to a tissue sample, a tumor sample, a cell or a biological fluid.

"Antigen loss escape variants" as used herein refer to cells which exhibit reduced or loss of expression of the target antigen, which antigens are targeted by the CARs of the invention.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type 1), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

The term "autologous," as used herein refers to any material derived from the same individual to which it is later to be reintroduced. For example, T cells from a patient may be isolated, genetically engineered to express a CAR and then reintroduced into the patient.

The term "B-cell associated diseases" as used herein include B-cell immunodeficiencies, autoimmune diseases and/or excessive/uncontrolled cell proliferation associated with B-cells (including lymphomas and/or leukemia's).

Examples of such diseases, wherein bispecific CARs of the invention may be used for therapeutic approaches include but are not limited to systemic lupus erythematosus (SLE), diabetes, rheumatoid arthritis (RA), reactive arthritis, multiple sclerosis (MS), pemphigus vulgaris, celiac disease, Crohn's disease, inflammatory bowel disease, ulcerative colitis, autoimmune thyroid disease, X-linked agammaglobulinaemis, pre-B acute lymphoblastic leukemia, systemic lupus erythematosus, common variable immunodeficiency, chronic lymphocytic leukemia, diseases associated with selective IgA deficiency and/or IgG subclass deficiency, B lineage lymphomas (Hodgkin's lymphoma and/or non-Hodgkin's lymphoma), immunodeficiency with thymoma, transient hypogammaglobulinemia and/or hyper IgM syndrome, as well as virally-mediated B-cell diseases such as EBV mediated lymphoproliferative disease, and chronic infections in which B-cells participate in the pathophysiology.

The term "blood-brain barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the central nerve system (CNS), and are herein collectively referred to as the "blood-brain barrier" or "BBB." The BBB also encompasses the blood-cerebral spinal fluid barrier (choroid plexus) where the barrier is included of ependymal cells rather than capillary endothelial cells.

The terms "cancer" and "cancerous" as used herein refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

The term "chimeric antigen receptor" or "CAR" or "CARs" as used herein refers to engineered receptors, which graft antigen specificity onto a cytotoxic cell, for example T cells, NK cells and macrophages. The CARs of the invention may include at least one antigen specific targeting region (ASTR), an extracellular spacer domain (ESD), a transmembrane domain (TM), one or more co-stimulatory domains (CSD), and an intracellular signaling domain (ISD). In an embodiment, the ESD and/or CSD are optional. In another embodiment, the CAR is a bispecific CAR, which is specific to two different antigens or epitopes. After the ASTR binds specifically to a target antigen, the ISD activates intracellular signaling. For example, the ISD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

The term "co-express" as used herein refers to simultaneous expression of two or more genes. Genes may be nucleic acids encoding, for example, a single protein or a chimeric protein as a single polypeptide chain. For example, the CARs of the invention may be co-expressed with a therapeutic control (for example truncated epidermal growth factor (EGFRt)), wherein the CAR is encoded by a first polynucleotide chain and the therapeutic control is encoded by a second polynucleotide chain. In an embodiment, the first and second polynucleotide chains are linked by a nucleic acid sequence that encodes a cleavable linker. Alternately, the CAR and the therapeutic control are encoded by two different polynucleotides that are not linked via a linker but are instead encoded by, for example, two different vectors.

The term "cognate" as used herein refers to a gene sequence that is evolutionarily and functionally related between species. For example, but without limitation, in the human genome the human CD4 gene is the cognate gene to the mouse 3d4 gene, since the sequences and structures of these two genes indicate that they are highly homologous and both genes encode a protein which functions in signaling T cell activation through MHC class II-restricted antigen recognition.

The term "conditionally active biologic protein" refers to a variant, or mutant, of a wild-type protein which is more or less active than the parent wild-type protein under one or more normal physiological conditions. This conditionally active protein also exhibits activity in selected regions of the body and/or exhibits increased or decreased activity under aberrant, or permissive, physiological conditions. The term "normal physiological condition" as used herein refers to one of temperature, pH, osmotic pressure, osmolality, oxidative stress, electrolyte concentration, a concentration of a small organic molecule such as glucose, lactic acid, pyruvate, nutrient components, other metabolites, and the like, a concentration of another molecule such as oxygen, carbonate, phosphate, and carbon dioxide, as well as cell types, and nutrient availability, which would be considered within a normal range at the site of administration, or at the tissue or organ at the site of action, to a subject.

The term "aberrant condition" as used herein refers to a condition that deviates from the normally acceptable range for that condition. In one aspect, the conditionally active biologic protein is virtually inactive at a normal physiological condition but is active at an aberrant condition at a level that is equal or better than the wild-type protein from which it is derived. For example, in one aspect, an evolved conditionally active biologic protein is virtually inactive at body temperature, but is active at lower temperatures. In another aspect, the conditionally active biologic protein is reversibly or irreversibly inactivated at the normal physiological condition. In a further aspect, the wild-type protein is a therapeutic protein. In another aspect, the conditionally active biologic protein is used as a drug, or therapeutic agent. In yet another aspect, the protein is more or less active in highly oxygenated blood, such as, for example, after passage through the lung or in the lower pH environments found in the kidney.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference "TATAC" and is complementary to a reference sequence "GTATA."

The term "co-stimulatory ligand" as used herein includes a molecule on an antigen presenting cell (e.g., dendritic cell, B cell, and the like) that specifically binds a cognate co-stimulatory molecule on a T cell, thereby providing a signal which, in addition to the primary signal provided by, for instance, by the binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, an inducible costimulatory ligand (ICOS-L), an intercellular adhesion molecule (ICAM), CD30L, CD40, CD70, CD83, HLA-G, MICA, MICB, HVEM, a lymphotoxin beta receptor, 3/TR6, ILT3, ILT4, HVEM, an agonist or an antibody that binds to a Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, a lymphocyte function-associated antigen-1 (LFA-1), CD2, CD7, LIGHT, NKG2C, B7-H3, and a ligand that specifically binds with CD83.

The term "co-stimulatory molecule" as used herein refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class 1 molecule, BTLA and a Toll ligand receptor.

The term "co-stimulatory signal" as used herein refers to a signal, which in combination with a primary signal, such as TCR/CD3 ligation, leads to T cell proliferation and/or upregulation or down regulation of key molecules.

The term "cytotoxic cell" as used herein means a cell which can injure or destroy invading microorganisms, tumor cells or other diseased tissue cells. This term is meant to include natural killer (NK) cells, activated NK cells, neutrophils, T cells, eosinophils, basophils, B-cells, macrophages and lymphokine-activated killer (LAK) cells among other cell types. The cytotoxic cell, through an antibody, receptor, ligand or fragments/derivatives thereof, is bound to a target cell to form a stable complex, and stimulates the cytotoxic cell to destroy the target cell.

Cytotoxic cells may also include other immune cells with tumor lytic capabilities including but not limited to natural killer T cells (Heczey et al., "Invariant NKT cells with chimeric antigen receptor provide a novel platform for safe and effective cancer immunotherapy," *Blood*, vol. 124, pp. 2824-2833, 2014) and granulocytes. Further, cytotoxic cells may include immune cells with phagocytic capability including but not limited to macrophages and granulocytes, cells with stem cell and/or progenitor cell properties including, but not limited to, hematopoietic stem/progenitor cells (Zhen et al., "HIV-specific Immunity Derived From Chimeric Antigen Receptor-engineered Stem Cells,"*Mol Ther., vol.* 23, pp. 1358-1367, 2015), embryonic stem cells (ESCs), cord blood stem cells, and induced pluripotent stem cells (iPSCs) (Themeli et al., "New cell sources for T cell engineering and adoptive immunotherapy," *Cell Stem Cell.*, vol. 16, pp. 357-366, 2015). Additionally, cytotoxic cells include "synthetic cells" such as iPSC-derived T cells (TiPSCs) (Themeli et al., "Generation of tumor-targeted human T lymphocytes from induced pluripotent stem cells for cancer therapy," *Nat Biotechnol.*, vol. 31, pp. 928-933, 2013) or iPSC-derived NK cells.

The term "degrading effective" amount refers to the amount of enzyme which is required to process at least 50% of the substrate, as compared to substrate not contacted with the enzyme.

The term "directional ligation" refers to a ligation in which a 5' end and a 3' end of a polynucleotide are different enough to specify a preferred ligation orientation. For example, an otherwise untreated and undigested PCR product that has two blunt ends will typically not have a preferred ligation orientation when ligated into a cloning vector digested to produce blunt ends in its multiple cloning site; thus, directional ligation will typically not be displayed under these circumstances. In contrast, directional ligation will typically be displayed when a digested PCR product having a 5' EcoR I-treated end and a 3' BamH I is ligated into a cloning vector that has a multiple cloning site digested with EcoR I and BamH I.

The term "disease targeted by genetically modified cytotoxic cells" as used herein encompasses the targeting of any cell involved in any manner in any disease by the genetically modified cells of the invention, irrespective of whether the genetically modified cells target diseased cells or healthy cells to effectuate a therapeutically beneficial result. The genetically modified cells include but are not limited to genetically modified T cells, NK cells, and macrophages. The genetically modified cells express the CARs of the invention, which CARs may target any of the antigens expressed on the surface of target cells. Examples of antigens which may be targeted include but are not limited to antigens expressed on B-cells; antigens expressed on carcinomas, sarcomas, lymphomas, leukemia, germ cell tumors, and blastomas; antigens expressed on various immune cells; and antigens expressed on cells associated with various hematologic diseases, autoimmune diseases, and/or inflammatory diseases. Other antigens that may be targeted will be apparent to those of skill in the art and may be targeted by the CARs of the invention in connection with alternate embodiments thereof.

The terms "genetically modified cells", "redirected cells", "genetically engineered cells" or "modified cells" as used herein refer to cells that express the CARs of the invention.

The term "DNA shuffling" is used herein to indicate recombination between substantially homologous but non-identical sequences, in some embodiments DNA shuffling may involve crossover via non-homologous recombination, such as via cer/lox and/or flp/frt systems and the like. DNA shuffling can be random or non-random.

The term "drug" or "drug molecule" refers to a therapeutic agent including a substance having a beneficial effect on a human or animal body when it is administered to the human or animal body. Preferably, the therapeutic agent includes a substance that can treat, cure or relieve one or more symptoms, illnesses, or abnormal conditions in a human or animal body or enhance the wellness of a human or animal body.

An "effective amount" is an amount of a conditionally active biologic protein or fragment which is effective to treat or prevent a condition in a living organism to whom it is administered over some period of time, e.g., provides a therapeutic effect during a desired dosing interval.

The term "electrolyte" as used herein defines a mineral in the blood or other body fluids that carries a charge. For example, in one aspect, the normal physiological condition and aberrant condition can be conditions of "electrolyte concentration". In one aspect, the electrolyte concentration to be tested is selected from one or more of ionized calcium, sodium, potassium, magnesium, chloride, bicarbonate, and phosphate concentration. For example, in one aspect, normal range of serum calcium is 8.5 to 10.2 mg/dL. In this aspect, aberrant serum calcium concentration may be selected from either above or below the normal range, m another example, in one aspect, normal range of serum chloride is 96-106 milliequivalents per liter (mEq/L). In this aspect, aberrant serum chloride concentration may be selected from either above or below the normal range, in another example, in one aspect, a normal range of serum magnesium is from 1.7-2.2 mg/dL. In this aspect, an aberrant serum magnesium concentration may be selected from either above or below the normal range, in another example, in one aspect, a normal range of serum phosphorus is from 2.4 to 4.1 mg/dL. In this aspect, aberrant serum phosphorus concentration may be selected from either above or below the normal range. In another example, in one aspect, a normal range of serum, or blood, sodium is from 135 to 145 mEq/L. In this aspect, aberrant serum, or blood, sodium concentration may be selected from either above or below the normal range. In another example, in one aspect, a normal range of serum, or blood, potassium is from 3.7 to 5.2 mEq/L. In this aspect, aberrant serum, or blood, potassium concentration maybe selected from either above or below the normal range. In a further aspect, a normal range of serum bicarbonate is from 20 to 29 mEq/L. In this aspect, aberrant serum, or blood, bicarbonate concentration may be selected from either above or below the normal range. In a different aspect, bicarbonate levels can be used to indicate normal levels of acidity (pH), in the blood. The term "electrolyte concentration" may also be used to define the condition of a particular electrolyte in a tissue or body fluid other than blood or plasma. In this case, the normal physiological condition is considered to be the clinically normal range for that tissue or fluid. In this aspect, aberrant tissue or fluid electrolyte concentration may be selected from either above or below the normal range.

The term "epitope" as used herein refers to an antigenic determinant on an antigen, such as an enzyme polypeptide, to which the paratope of an antibody, such as an enzyme-specific antibody, binds. Antigenic determinants usually consist of chemically active surface groupings of molecules, such as amino acids or sugar side chains, and can have specific three-dimensional structural characteristics, as well as specific charge characteristics. As used herein "epitope" refers to that portion of an antigen or other macromolecule capable of forming a binding interaction that interacts with the variable region binding body of an antibody. Typically, such binding interaction is manifested as an intermolecular contact with one or more amino acid residues of a CDR.

As used herein, the term "evolution", or "evolving", refers to using one or more methods of mutagenesis to generate a novel polynucleotide encoding a novel polypeptide, which novel polypeptide is itself an improved biological molecule &/or contributes to the generation of another improved biological molecule. In a particular non-limiting aspect, the present disclosure relates to evolution of conditionally active biologic proteins from a parent wild type protein. In one aspect, for example, evolution relates to a method of performing both non-stochastic polynucleotide chimerization and non-stochastic site-directed point mutagenesis disclosed in U.S. patent application publication 2009/0130718. More particularly, the present disclosure provides methods for evolution of conditionally active biologic enzymes which exhibit reduced activity at normal physiological conditions compared to a wild-type enzyme parent molecule, but enhanced activity under one or more aberrant conditions compared to the antigen specific targeting region of the wild-type enzyme.

The terms "fragment", "derivative" and "analog" when referring to a reference polypeptide include a polypeptide which retains at least one biological function or activity that is at least essentially same as that of the reference polypeptide. Furthermore, the terms "fragment", "derivative" or "analog" are exemplified by a "pro-form" molecule, such as a low activity proprotein that can be modified by cleavage to produce a mature enzyme with significantly higher activity.

The term "gene" as used herein means the segment of DNA involved in producing a polypeptide chain; it includes regions preceding and following the coding region (leader and trailer) as well as intervening sequences (nitrons) between individual coding segments (exons).

The term "heterologous" as used herein means that one single-stranded nucleic acid sequence is unable to hybridize to another single-stranded nucleic acid sequence or its complement. Thus, areas of heterology mean that areas of polynucleotides or polynucleotides have areas or regions within their sequence which are unable to hybridize to another nucleic acid or polynucleotide. Such regions or areas are for example areas of mutations.

The term "homologous" or "homeologous" as used herein means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentrations as discussed later. Preferably the region of identity is greater than about 5 bp, more preferably the region of identity is greater than 10 bp.

The benefits of this disclosure extend to "industrial applications" (or industrial processes), which term is used to include applications in commercial industry proper (or simply industry) as well as non-commercial industrial applications (e.g. biomedical research at a non-profit institution). Relevant applications include those in areas of diagnosis, medicine, agriculture, manufacturing, and academia.

The term "immune cell" as used herein refers to cells of the mammalian immune system including but not limited to antigen presenting cells, B-cells, basophils, cytotoxic T cells, dendritic cells, eosinophils, granulocytes, helper T cells, leukocytes, lymphocytes, macrophages, mast cells, memory cells, monocytes, natural killer cells, neutrophils, phagocytes, plasma cells and T cells.

The term "immune response" as used herein refers to immunities including but not limited to innate immunity, humoral immunity, cellular immunity, immunity, inflammatory response, acquired (adaptive) immunity, autoimmunity and/or overactive immunity The term "isolated" as used herein means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The term "isolated nucleic acid" as used herein to define a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

The term "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient ways to deliver a gene delivery vector. HIV, SIV, and FIV are all examples of lentiviruses. Vectors derived from lentiviruses offer the means to achieve significant levels of gene transfer in vivo.

The term "ligand" as used herein refers to a molecule, such as a random peptide or variable segment sequence that is recognized by a particular receptor. As a person skilled in the art will recognize, a molecule (or macromolecular complex) can be both a receptor and a ligand. In general, the binding partner having a smaller molecular weight is referred to as the ligand and the binding partner having a greater molecular weight is referred to as a receptor.

The term "ligation" as used herein refers to the process of forming phosphodiester bonds between two double stranded nucleic acid fragments (Sambrook et al., (1982). Molecular Cloning: A Laboratory Manual. Cold Spring Harbour Laboratory, Cold Spring Harbor, N.Y., p. 146; Sambrook et al., Molecular Cloning: a laboratory manual, $2^{nd}$ Ed., Cold Spring Harbor Laboratory Press, 1989). Unless otherwise provided, ligation may be accomplished using known buffers and conditions with 10 units of T4 DNA ligase ("ligase") per 0.5 micrograms of approximately equimolar amounts of the DNA fragments to be ligated.

The terms "linker" or "spacer" as used herein refer to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein. "Linker" (L) or "linker domain" or "linker region" as used herein refers to an oligo- or polypeptide region of from about 1 to 100 amino acids in length, which links together any of the domains/regions of the CARs of the invention. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. In some embodiments, the linkers include the picornaviral 2A-like linker, CHYSEL sequences of porcine teschovirus (P2A), Thosea asigna virus (T2A) or combinations, variants and functional equivalents thereof. Other linkers will be apparent to those skilled in the art and may be used in connection with alternate embodiments of the invention.

The term "mammalian cell surface display" as used herein refers to a technique whereby a protein or antibody, or a portion of an antibody, is expressed and displayed on a mammalian host cell surface for screening purposes; for example, by screening for specific antigen binding by a combination of magnetic beads and fluorescence-activated cell sorting. In one aspect, mammalian expression vectors are used for simultaneous expression of immunoglobulins as both a secreted and cell surface bound form as in DuBridge et al., US 2009/0136950. In another aspect, the techniques are employed for screening a viral vector encoding for a library of antibodies or antibody fragments that are displayed on the cell membranes when expressed in a cell as in Gao et al., US 2007/0111260. Whole IgG surface display on mammalian cells is known. For example, Akamatsuu et al. developed a mammalian cell surface display vector, suitable for directly isolating IgG molecules based on their antigen-binding affinity and biological activity. Using an Epstein-Barr virus-derived episomal vector, antibody libraries were displayed as whole IgG molecules on the cell surface and screened for specific antigen binding by a combination of magnetic beads and fluorescence-activated cell sorting. Plasmids encoding antibodies with desired binding characteristics were recovered from sorted cells and converted to a form suitable for production of soluble IgG. See Akamatsuu et al. *J. Immunol. Methods*, vol. 327, pages 40-52, 2007. Ho et al. used human embryonic kidney 293T cells that are widely used for transient protein expression for cell surface display of single-chain Fv antibodies for affinity maturation. Cells expressing a rare mutant antibody with higher affinity were enriched 240-fold by a single-pass cell sorting from a large excess of cells expressing WT antibody with a slightly lower affinity. Furthermore, a highly enriched mutant was obtained with increased binding affinity for CD22 after a single selection of a combinatory library randomizing an intrinsic antibody hotspot. See Ho et al., "Isolation of anti-CD22 Fv with high affinity by Fv display on human cells," *Proc Natl Acad Sci USA*, vol. 103, pages 9637-9642, 2006.

B cells specific for an antigen may also be used. Such B cells may be directly isolated from peripheral blood mononuclear cells (PBMC) of human donors. Recombinant, antigen-specific single-chain Fv (scFv) libraries are generated from this pool of B cells and screened by mammalian cell surface display by using a Sindbis virus expression system. The variable regions (VRs) of the heavy chains (HCs) and light chains (LCs) can be isolated from positive clones and recombinant fully human antibodies produced as whole IgG or Fab fragments. In this manner, several hypermutated high-affinity antibodies binding the Qβ virus like particle (VLP), a model viral antigen, as well as antibodies specific for nicotine can be isolated. See Beerli et al., "Isolation of human monoclonal antibodies by mammalian cell display," *Proc Natl Acad Sci USA*, vol. 105, pages 14336-14341, 2008.

Yeast cell surface display may also be used in the present invention, for example, see Kondo and Ueda, "Yeast cell-surface display-applications of molecular display," *Appl. Microbiol. Biotechnol.*, vol. 64, pages 28-40, 2004, which describes for example, a cell-surface engineering system using the yeast *Saccharomyces cerevisiae*. Several representative display systems for the expression in yeast *S. cerevisiae* are described in Lee et al, "Microbial cell-surface display," *TRENDS in Bitechnol.*, vol. 21, pages 45-52, 2003. Also Boder and Wittrup, "Yeast surface display for screening combinatorial polypeptide libraries," *Nature Biotechnol.*, vol. 15, pages 553, 1997.

The term "manufacturing" as used herein refers to production of a protein in a sufficient quantity to permit at least Phase I clinical testing of a therapeutic protein, or sufficient quantity for regulatory approval of a diagnostic protein.

As used herein, the term "microenvironment" means any portion or region of a tissue or body that has a constant or temporal, physical or chemical difference from other regions of the tissue or other regions of the body.

As used herein, the term "molecular property to be evolved" includes reference to molecules included of a polynucleotide sequence, molecules included of a polypeptide sequence, and molecules included in part of a polynucleotide sequence and in part of a polypeptide sequence. Particularly relevant—but by no means limiting—examples of molecular properties to be evolved include protein activities at specified conditions, such as related to temperature; salinity; osmotic pressure; pH; oxidative stress, and concentration of glycerol, DMSO, detergent, and/or any other molecular species with which contact is made in a reaction environment. Additional particularly relevant—but by no means limiting—examples of molecular properties to be evolved include stabilities—e.g. the amount of a residual molecular property that is present after a specified exposure time to a specified environment, such as may be encountered during storage.

The term "mutations" as used herein means changes in the sequence of a wild-type nucleic acid sequence or changes in the sequence of a peptide. Such mutations may be point mutations such as transitions or transversions. The mutations may be deletions, insertions or duplications.

The term "multispecific antibody" as used herein is an antibody having binding affinities for at least two different epitopes. Multispecific antibodies can be prepared as full-length antibodies or antibody fragments (e.g. F(ab')$_2$ bispecific antibodies). Engineered antibodies may bind to two, three or more (e.g. four) antigens (see, e.g., US 2002/0004587 A1). One conditionally active antibody may be engineered to be multispecific, or two antibodies may be engineered to include a hetero-dimer that binds to two antigens. Multispecific antibodies can also be multifunctional.

As used herein, the degenerate "N,N,G/T" nucleotide sequence represents 32 possible triplets, where "N" can be A, C, G or T.

The term "naturally-occurring" as used herein as applied to the object refers to the fact that an object can be found in nature. For example, a polypeptide or polynucleotide sequence that is present in an organism (including viruses) that can be isolated from a source in nature and which has not been intentionally modified by man in the laboratory is naturally occurring. Generally, the term naturally occurring refers to an object as present in a non-pathological (undiseased) individual, such as would be typical for the species.

As used herein, "normal physiological conditions", or "wild type operating conditions", are those conditions of temperature, pH, osmotic pressure, osmolality, oxidative stress and electrolyte concentration which would be considered within a normal range at the site of administration, or the site of action, in a subject.

As used herein, the term "nucleic acid molecule" is included of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules included chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

The terms "nucleic acid sequence coding for" or a "DNA coding sequence of or a "nucleotide sequence encoding" as used herein refer to a DNA sequence which is transcribed and translated into an enzyme when placed under the control of appropriate regulatory sequences such as promoters. A "promotor" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The term "oligonucleotide" (or synonymously an "oligo") refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

As used herein the term "parental polynucleotide set" is a set included of one or more distinct polynucleotide species. Usually this term is used in reference to a progeny polynucleotide set which is preferably obtained by mutagenization of the parental set, in which case the terms "parental", "starting" and "template" are used interchangeably.

The term "patient", or "subject", refers to an animal, for example a mammal, such as a human, who is the object of treatment. The subject, or patient, may be either male or female.

As used herein the term "physiological conditions" refers to temperature, pH, osmotic pressure, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions include 50-200 mM NaCl or KCl, pH 6.5-8.5, 20-45 degrees C. and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., bovine serum albumin (BSA)). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or non-ionic detergents and/or membrane fractions and/or anti-foam agents and/or scintillants. Normal physiological conditions refer to conditions of temperature, pH, osmotic pressure, osmolality, oxidative stress and electrolyte concentration in vivo in a patient or subject at the site of administration, or the site of action, which would be considered within the normal range in a patient.

Standard convention (5' to 3') is used herein to describe the sequence of double stranded polynucleotides.

The term "population" as used herein means a collection of components such as polynucleotides, portions or polynucleotides or proteins. A "mixed population" means a collection of components which belong to the same family of nucleic acids or proteins (i.e., are related) but which differ in their sequence (i.e., are not identical) and hence in their biological activity.

A molecule having a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When two or more chemical modifications (e.g. two proteolytic cleavages, or a proteolytic cleavage and a deglycosylation) can be distinguished en route to the production of a mature molecule, the reference precursor molecule may be termed a "pre-pro-form" molecule.

As used herein, the term "receptor" refers to a molecule that has an affinity for a given ligand. Receptors can be naturally occurring or synthetic molecules. Receptors can be employed in an unaltered state or as aggregates with other species. Receptors can be attached, covalently or non-covalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

The term "reductive reassortment", as used herein, refers to the increase in molecular diversity that is accrued through deletion (and/or insertion) events that are mediated by repeated sequences.

The term "restriction site" as used herein refers to a recognition sequence that is necessary for the manifestation of the action of a restriction enzyme, and includes a site of catalytic cleavage. It is appreciated that a site of cleavage may or may not be contained within a portion of a restriction site that includes a low ambiguity sequence (i.e. a sequence containing the principal determinant of the frequency of occurrence of the restriction site). When an enzyme (e.g. a restriction enzyme) is said to "cleave" a polynucleotide, it is understood to mean that the restriction enzyme catalyzes or facilitates a cleavage of a polynucleotide.

As used herein, the term "single-chain antibody" refers to a polypeptide including a VH domain and a VL domain in polypeptide linkage, generally liked via a spacer peptide, and which may include additional amino acid sequences at the amino- and/or carboxy-termini. For example, a single-chain antibody may include a tether segment for linking to the encoding polynucleotide. As an example a scFv is a single-chain antibody. Single-chain antibodies are generally proteins consisting of one or more polypeptide segments of at least 10 contiguous amino substantially encoded by genes of the immunoglobulin superfamily (e.g, see The Immunoglobulin Gene Superfamily, A. F. Williams and A. N. Barclay, in Immunoglobulin Genes, T. Honjo, F. W. Alt, and THE. Rabbits, eds., (1989) Academic press: San Diego, Calif., pp. 361-368, most frequently encoded by a rodent, non-human primate, avian, porcine bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

The members of a pair of molecules (e.g., an antibody-antigen pair and ligand-receptor pair) are said to "specifically bind" to each other if they bind to each other with greater affinity than to other, non-specific molecules. For example, an antibody raised against an antigen to which it binds more efficiently than to a non-specific protein can be described as specifically binding to the antigen.

The term "stimulation" as used herein means a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

The term "stimulatory molecule" as used herein means a molecule on a T cell that specifically binds with a cognate stimulatory ligand present on an antigen presenting cell.

The term "stimulatory ligand" as used herein means a ligand that when present on an antigen presenting cell (e.g, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "target cell" as used herein refers to cells which are involved in a disease and can be targeted by the genetically modified cytotoxic cells of the invention (including but not limited to genetically modified T cells, NK cells, and macrophages). Other target cells will be apparent to those skilled in the art and may be used in connection with alternate embodiments of the invention.

The terms "T cell" and "T-lymphocyte" are interchangeable and used synonymously herein. Examples include, but are not limited to, naive T cells, central memory T cells, effector memory T cells and combinations thereof.

The term "transduction" as used herein refers to the introduction of a foreign nucleic acid into a cell using a viral vector. "Transfection" as used herein refers to the introduction of a foreign nucleic acid into a cell using recombinant DNA technology. The term "transformation" means the introduction of a "foreign" (i.e. extrinsic or extracellular) gene, DNA or RNA sequence to a host cell, so that the host cell will express the introduced gene or sequence to produce a desired substance, such as a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

"Tumor," as used herein refers to all neoplastic cell growth and proliferation, whether malignant or benign, and all pre-cancerous and cancerous cells and tissues As used herein, the term "tumor microenvironment" refers to any and all elements of the tumor milieu including elements that create a structural and or functional environment for the malignant process to survive and/or expand and/or spread.

As used herein, the term "variable segment" refers to a portion of a nascent peptide which includes a random, pseudorandom, or defined kernal sequence. A "variable segment" refers to a portion of a nascent peptide which includes a random pseudorandom, or defined kernal sequence. A variable segment can include both variant and invariant residue positions, and the degree of residue variation at a variant residue position may be limited: both options are selected at the discretion of the practitioner. Typically, variable segments are about 5 to 20 amino acid residues in length (e.g., 8 to 10), although variable segments may be longer and may include antibody portions or receptor proteins, such as an antibody fragment, a nucleic acid binding protein, a receptor protein, and the like.

"Vector", "cloning vector" and "expression vector" as used herein refer to the vehicle by which a polynucleotide sequence (e.g. a foreign gene) can be introduced into a host cell, so as to transform the host and promote expression (e.g. transcription and translation) of the introduced sequence. Vectors include plasmids, phages, viruses, etc.

As used herein, the term "wild-type" means that the polynucleotide does not include any mutations. A "wild type protein", "wild-type protein", "wild-type biologic protein", or "wild type biologic protein", refers to a protein which can be isolated from nature that will be active at a level of activity found in nature and will include the amino acid sequence found in nature. The terms "parent molecule" and "target protein" also refer to the wild-type protein. The "wild-type protein" preferably has some desired properties, such as higher binding affinity, or enzymatic activity, which may be obtained by screening of a library of proteins for a desired properties, including better stability in different temperature or pH environments, or improved selectivity and/or solubility.

The term "working", as in "working sample", for example, is simply a sample with which one is working. Likewise, a "working molecule", for example is a molecule with which one is working.

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

The present disclosure is directed to a chimeric antigen receptor (CAR) for binding with a target antigen, comprising at least one antigen specific targeting region evolved from a wild-type protein or a domain thereof and having at least one of: (a) a decrease in activity in the assay at the normal physiological condition compared to the antigen specific targeting region of the wild-type protein or a domain thereof, and (b) an increase in activity in the assay under the aberrant condition compared to the antigen specific targeting region of the wild-type protein or a domain thereof; a transmembrane domain; and an intracellular signaling domain. In some embodiments, the chimeric antigen receptor further includes an extracellular spacer domain or at least one co-stimulatory domain.

The CARs of the present invention have at least one of (1) their affinity to the target antigen reversibly or irreversibly reduced at the normal physiological condition, and (2) an increased affinity, in comparison with the same CAR without the conditionally active antigen specific targeting region. These CARs can direct cytotoxic cells to a disease site where an aberrant condition is present, such as a tumor microenvironment or synovial fluid. As a result of these properties, the CARs can preferentially direct the cytotoxic cells to a disease site while because of their low affinity for normal tissue. Such CARs can dramatically reduce side-effects and allow higher doses of therapeutics to be used to increase therapeutic efficacy. The CARs are particularly valuable for development of novel therapeutics that are required for short or limited periods of time within a subject. Examples of beneficial applications include systemic treatments at high dosages, as well as localized treatments at high concentrations.

The chimeric antigen receptor may include an antigen specific targeting region that has a decrease in a binding affinity to the target antigen at a normal physiological condition compared to the antigen specific targeting region of the wild-type protein or the domain thereof.

The chimeric antigen receptor many include an antigen specific targeting region that has an increase in activity in the assay under the aberrant condition compared to the antigen specific targeting region of the wild-type protein or a domain thereof and a decrease in a binding affinity to the target antigen at a normal physiological condition compared to the antigen specific targeting region of the wild-type protein or the domain thereof.

In any of the foregoing chimeric antigen receptors the antigen specific targeting region may also have an increase in selectivity in the assay under the aberrant condition compared to the antigen specific targeting region of the wild-type protein or a domain thereof.

The CAR molecule includes a linker to connect the two antigen specific targeting regions (FIG. 1). The linker orients the two antigen specific targeting regions in such a way that the two antigen specific targeting regions on the CAR-T cells exhibit improved or optimal activity in binding to the target antigen (Jensen et al., "Design and implementation of adoptive therapy with chimeric antigen receptor-modified T cells," *Immunol Rev.*, vol. 257, pp. 127-144, 2014). The linker is thus preferably capable of adopting a specific conformation which enables improved or optimal binding of the two antigen specific targeting regions to the target antigen, thereby increasing the effectiveness of the CAR-T cells.

In some embodiments, the linker may be Gly-Ser tandem repeats in a length of 18-25 amino acids (Grada, "TanCAR: A Novel Bispecific Chimeric Antigen Receptor for Cancer Immunotherapy," *Molecular Therapy Nucleic Acids*, vol. 2, e105, 2013). This flexible linker is capable of adopting many different conformations for improved or optimal presentation of two antigen specific targeting regions for binding to the target antigen.

In some embodiments, the linker is capable of adopting different conformations at a normal physiological condition and an aberrant condition. Particularly, the linker has a first conformation at the aberrant condition which is improved or optimal for presentation of two antigen specific targeting regions for binding to the target antigen, while the same linker has a second conformation at the normal physiological condition which is less effective for presentation of two antigen specific targeting regions for binding to the target antigen than the first conformation of the linker under the aberrant condition. Such a linker may be called a "conditional linker" that allows the two antigen specific targeting regions to bind to the target antigen at a higher binding activity at an aberrant condition than at a normal physiological condition. Therefore, CAR-T cells including such a conditional linker are more active at an aberrant condition than the same CAR-T cells at a normal physiological condition.

Proteins that change conformation at different pH have been described previously, for example, in Di Russo et al. ("pH-Dependent conformational changes in proteins and their effect on experimental pK(a)s: the case of Nitrophorin 4," *PLoS Comput Biol.*, vol. 8, e1002761, 2012). Further, proteins with different conformations at different temperatures have been described in Caldwell, "Temperature-induced protein conformational changes in barley root plasma membrane-enriched microsomes," *Plant Physiol.*, vol. 84, pp. 924-929, 1989. The conformation of antibodies being influenced by pH and/or temperature has been discussed in Gandhi, "Effect of pH and temperature on conformational changes of a humanized monoclonal antibody," Master's thesis from University of Rhode Island, U.S.

It is within the scope of the present invention to select a conditional linker to be used in the CAR molecule. The conditional linker can adopt a first conformation at an aberrant condition, which is improved or optimal for presenting the two antigen specific targeting regions for binding to the target antigen, and adopt a second conformation at a normal physiological condition, which is suboptimal for presenting the two antigen specific targeting regions for binding to the target antigen. In some embodiments, the suboptimal conformation of the linker at the normal physiological condition produces a CAR molecule having a binding activity to the target antigen that is less than about 90%, or about 80%, or about 70%, or about 60%, or about 50%, or about 40%, or about 30%, or about 20%, or about 10%, or about 5% of the binding activity of the CAR molecule with the improved or optimal conformation of the linker at the aberrant condition.

The conditional linker may be generated from a starting linker selected from 2A linkers, 2A-like linkers, picornaviral 2A-like linkers, a 2A peptide of porcine teschovirus (P2A), and a 2A peptide of thosea asigna virus (T2A), as well as variants and functional equivalents thereof. The starting linker is evolved to produce mutant proteins; the mutant proteins are then subjected to an assay at a normal physiological condition and an assay at an aberrant condition. Proteins having a conditional linker are selected from the mutant proteins on the basis that the selected proteins exhibit (a) a conditional linker having a first conformation at the aberrant condition, which is improved or optimal for presenting the two antigen specific targeting regions for binding to the target antigen, and (b) a second conformation of the conditional linker at the normal physiological condition, which is suboptimal for presenting the two antigen specific targeting regions for binding to the target antigen.

The CAR molecule also includes an extracellular spacer domain that connects the two antigen specific targeting regions with the transmembrane domain, which, in turn, connects to the co-stimulatory domain and the intracellular signaling domain inside of the T cells (FIG. 1). The extracellular spacer domain is preferably capable of supporting the antigen specific targeting regions to recognize and bind to the target antigen on the target cells (Hudecek et al., "The non-signaling extracellular spacer domain of chimeric antigen receptors is decisive for in vivo antitumor activity," *Cancer Immunol Res.*, vol. 3, pp. 125-135, 2015). In some embodiments, the extracellular spacer domain is a flexible domain, thus allowing the antigen specific targeting regions to have a structure to optimally recognize the specific structure and density of the target antigens on a cell such as tumor cell (Hudecek et al., "The non-signaling extracellular spacer domain of chimeric antigen receptors is decisive for in vivo antitumor activity," *Cancer Immunol Res.*, vol. 3, pp. 125-135, 2015). The flexibility of the extracellular spacer domain permits the extracellular spacer domain to adopt many different conformations.

In some embodiments, the extracellular spacer domain is capable of adopting different conformations at a normal physiological condition and an aberrant condition. Particularly, the extracellular spacer domain has a first conformation at the aberrant condition which is improved or optimal for presentation of two antigen specific targeting regions for binding to the target antigen, while the same extracellular spacer domain has a second conformation at the normal physiological condition which is suboptimal for presentation of two antigen specific targeting regions for binding to the target antigen. Such an extracellular spacer domain may be called a "conditional extracellular spacer domain" since it enables the two antigen specific targeting regions to bind to the target antigen at a higher binding activity at the aberrant condition than at the normal physiological condition. Therefore, with the conditional extracellular spacer domain, CAR-T cells may be more active at the aberrant condition than the same CAR-T cells at the normal physiological condition.

It is within the scope of the present invention to select a conditional extracellular spacer domain to be used in the CAR molecule. In some embodiments, the suboptimal conformation of the extracellular spacer domain at the normal physiological condition produces a CAR molecule having a binding activity to the target antigen that is less than about 90%, or about 80%, or about 70%, or about 60%, or about 50%, or about 40%, or about 30%, or about 20%, or about 10%, or about 5% of the CAR molecule with the optimal conformation for the same extracellular spacer domain at the aberrant condition.

It has been discovered that the ubiquitylation-resistant form for the region including the extracellular spacer domain and the transmembrane domain can enhance CAR-T cell signaling and thus augment antitumor activity (Kunii et la., "Enhanced function of redirected human t cells expressing linker for activation oft cells that is resistant to ubiquitylation," Human Gene Therapy, vol. 24, pp. 27-37, 2013). Within this region, the extracellular spacer domain is outside of the CAR-T cells, and thus is exposed to different conditions and can potentially be made conditionally ubiquitylation-resistant.

It is within the scope of the present invention that the extracellular spacer domain is conditionally ubiquitylation-resistant. Particularly, the extracellular spacer domain of the CAR molecule is more ubiquitylation-resistant at an aberrant condition than at a normal physiological condition. Therefore, the CAR-T cells having the conditionally ubiquitylation-resistant extracellular spacer domain will have enhanced cytotoxicity at the aberrant condition, relative to their cytotoxicity at the normal physiological condition.

The conditionally ubiquitylation-resistant extracellular spacer domain may be selected to be more ubiquitylation-resistant at an aberrant pH or aberrant temperature, and less ubiquitylation-resistant at a normal physiological pH or normal physiological temperature. In one embodiment, the conditionally ubiquitylation-resistant extracellular spacer domain is more ubiquitylation-resistant at a pH of a tumor microenvironment, and less ubiquitylation-resistant at a normal physiological pH, such as the pH in human blood plasma at pH 7.2-7.6.

To produce a conditional extracellular spacer domain, a starting protein fragment selected from an Fc fragment of an antibody, a hinge region of an antibody, a CH2 region of an antibody, and a CH3 region of an antibody, is evolved to produce mutant proteins. The mutant proteins are subjected to an assay at a normal physiological condition and an assay at an aberrant condition. The conditional extracellular spacer domain is selected from the mutant proteins that exhibit (a) a conditional extracellular spacer domain that has a first conformation at the aberrant condition for the antigen specific targeting region to bind to the target antigen at a higher binding activity and a second conformation of the conditional extracellular binding domain at the normal physiological condition for the antigen specific targeting region to bind to the target antigen at a lower binding activity than at the aberrant condition, or proteins that are (b) more ubiquitylation-resistant at the aberrant condition than at the normal physiological condition.

Any of the foregoing chimeric antigen receptors may be configured such that a protein containing the antigen receptor has an increase in expression level compared to the wild-type protein or a domain thereof.

In an alternative embodiment, the present invention provides a chimeric antigen receptor (CAR) for binding with a target antigen, including at least one antigen specific targeting region evolved from a wild-type protein or a domain thereof and having an increase in selectivity in the assay under the aberrant condition compared to the antigen specific targeting region of the wild-type protein or a domain thereof; a transmembrane domain; and an intracellular signaling domain. In some embodiments, the chimeric antigen receptor further includes an extracellular spacer domain or at least one co-stimulatory domain.

The present disclosure is also directed to methods of evolving a wild-type protein or a domain thereof to generate a conditionally active protein that has at least one of: (a) a decrease in activity in the assay at the normal physiological condition compared to the antigen specific targeting region of the wild-type protein or a domain thereof, and (b) an increase in activity in the assay under the aberrant condition compared to the antigen specific targeting region of the wild-type protein or a domain thereof. The conditionally active protein may be engineered into a CAR.

The chimeric antigen receptor produced by the method may include an antigen specific targeting region that has a decrease in a binding affinity to the target antigen at a normal physiological condition compared to the antigen specific targeting region of the wild-type protein or the domain thereof.

The chimeric antigen receptor produced by the method may include an antigen specific targeting region that has an increase in activity in the assay under the aberrant condition compared to the antigen specific targeting region of the wild-type protein or a domain thereof and a decrease in a binding affinity to the target antigen at a normal physiological condition compared to the antigen specific targeting region of the wild-type protein or the domain thereof.

In any of the foregoing chimeric antigen receptors produced by the method the antigen specific targeting region may also have an increase in selectivity in the assay under the aberrant condition compared to the antigen specific targeting region of the wild-type protein or a domain thereof.

Any of the foregoing chimeric antigen receptors produced by the method may be configured such that a protein containing the antigen receptor has an increase in expression level compared to the wild-type protein or a domain thereof.

In an alternative embodiment of the method, the chimeric antigen receptor (CAR) produced by the method for binding with a target antigen, includes at least one antigen specific targeting region evolved from a wild-type protein or a domain thereof and having an increase in selectivity in the assay under the aberrant condition compared to the antigen specific targeting region of the wild-type protein or a domain thereof; a transmembrane domain; and an intracellular signaling domain. In some embodiments, the chimeric antigen receptor further includes an extracellular spacer domain or at least one co-stimulatory domain.

Chimeric Antigen Receptors

The immune system of mammals, especially humans, has cytotoxic cells for targeting and destroying diseased tissue and/or pathogens. Using these cytotoxic cells to remove unwanted tissue (i.e. target tissue) such as tumors is a promising therapeutic approach. Other tissues that may be targeted for removal include glandular (e.g. prostate) hyperplasia, warts, and unwanted fatty tissue. However, this relatively new therapeutic approach has achieved only limited success so far. For example, using T cells to target and destroy tumors has relatively low long term benefits because the cancer cells may adapted to the new therapy by reducing expression of surface antigens to reduce the effectiveness of this therapy. Cancer cells can even dedifferentiate to evade detection in response to tumor-specific T cells. See Maher, "Immunotherapy of Malignant Disease Using Chimeric Antigen Receptor Engrafted T Cells," *ISRN Oncology*, vol. 2012, article ID 278093, 2012.

Cytotoxic cells expressing chimeric antigen receptors can significantly improve the specificity and sensitivity of these cytotoxic cells. For example, T cells expressing a CAR (CAR-T cells) are capable of using the CAR to direct the T cells to target tumor cells expressing a cell surface antigen that specifically binds to the CAR. Such CAR-T cells can deliver the cytotoxic agent more selectively to the tumor cells. CAR-T cells can directly recognize a target molecule and thus are typically not restricted by polymorphic presenting elements such as human leukocyte antigens (HLAs). Advantages of this CAR targeting strategy are threefold. First, since the CAR-T cell function is not dependent upon HLA status, the same CAR-based approach can in principle be used in all patients with tumors that express the same target surface antigen. Second, corruption of antigen processing and presenting machinery is a common attribute of tumor cells and may facilitate immune escape. However, this affords no protection against CAR-T cells. Third, a range of macromolecules can be targeted using this system, including proteins, carbohydrates, and glycolipids.

A chimeric antigen receptor of the present invention is a chimeric artificial protein including at least one antigen specific targeting region (ASTR), a transmembrane domain (TM), and an intracellular signaling domain (ISD). In some embodiments, the CAR may further include an extracellular spacer domain (ESD) and/or a co-stimulatory domain (CSD). See FIG. 1.

The ASTR is an extracellular region of the CAR for binding to a specific target antigen including proteins, carbohydrates, and glycolipids. In some embodiments, the ASTR includes an antibody, especially a single-chain antibody, or a fragment thereof. The ASTR may include a full length heavy chain, an Fab fragment, a single chain Fv (scFv) fragment, a divalent single chain antibody or a diabody, each of which are specific to the target antigen.

The ASTR may also include another protein functional domain to recognize and bind to the target antigen. Because the target antigen may have other biological functions, such as acting as a receptor or a ligand, the ASTR may alternatively include a functional domain for specifically binding with the antigen. Some examples of proteins with functional domains include linked cytokines (which leads to recognition of cells bearing the cytokine receptor), affibodies, ligand binding domains from naturally occurring receptors, soluble protein/peptide ligands for a receptor, for example on a tumor cell. In fact, almost any molecule that is capable of binding to a given antigen with high affinity can be used in the ASTR, as will be appreciated by those skilled in the art.

In one embodiment, the CAR of the invention includes at least two ASTRs which target at least two different antigens or two epitopes on the same antigen. In an embodiment, the CAR includes three or more ASTRs which target at least three or more different antigens or epitopes. When a plurality of ASTRs is present in the CAR, the ASTRs may be arranged in tandem and may be separated by linker peptides (FIG. 1).

In one embodiment, the ASTR includes a full-length IgG heavy chain that is specific for the target antigen and having the $V_H$, CHL hinge, and the CH2 and CH3 (Fc) Ig domains, if the $V_H$ domain alone is sufficient to confer antigen-specificity ("single-domain antibodies"). If both, the $V_H$ and the $V_L$ domains are necessary to generate a fully active ASTR, the $V_H$-containing CAR and the full-length lambda light chain (IgL) are both introduced into the same cytotoxic cell to generate an active ASTR. In another embodiment, each ASTR of the CAR includes at least two single chain antibody variable fragments (scFv), each specific for a different target antigen. scFvs, in which the C-terminus of one variable domain ($V_H$ or $V_L$) is tethered to the N-terminus of the other variable domain ($V_L$ or $V_H$, respectively) via a polypeptide linker, have been developed without significantly disrupting antigen binding or specificity of the binding (Chaudhary et al., "A recombinant single-chain immunotoxin composed of anti-Tac variable regions and a truncated diphtheria toxin," *Proc. Natl. Acad. Sci*., vol. 87, page 9491, 1990; Bedzyk et al.," "Immunological and structural characterization of a high affinity anti-fluorescein single-chain antibody," *J. Biol. Chem*., vol. 265, page 18615, 1990). These scFvs lack the constant regions (Fc) present in the heavy and light chains of a native antibody. The scFvs, specific for at least two different antigens, are arranged in tandem. In an embodiment, an extracelluar spacer domain may be linked between the ASTR and the transmembrane domain.

In another embodiment, an scFv fragment may be fused to all or a portion of the constant domains of the heavy chain. In a further embodiment, an ASTR of the CAR includes a divalent (or bivalent) single-chain variable fragment (di-scFvs, bi-scFvs). In CARs including di-scFVs, two scFvs each specific for an antigen are linked together to form a single peptide chain with two $V_H$ and two $V_L$ regions (Xiong et al., "Development of tumor targeting anti-MUC-1 multimer: effects of di-scFv unpaired cysteine location on PEGylation and tumor binding," *Protein Engineering Design and Selection*, vol. 19, pages 359-367, 2006; Kufer et al., "A revival of bispecific antibodies," *Trends in Biotechnology*, vol. 22, pages 238-244, 2004).

In yet another embodiment, an ASTR includes a diabody. In a diabody, the scFvs are created with linker peptides that are too short for the two variable regions to fold together, driving the scFvs to dimerize. Still shorter linkers (one or two amino acids) lead to the formation of trimers, the so-called triabodies or tribodies. Tetrabodies may also be used in the ASTR.

When two or more ASTRs are present in a CAR, the ASTRs are connected to each other covalently on a single polypeptide chain, through an oligo- or polypeptide linker, an Fc hinge or a membrane hinge region.

The antigens targeted by the CAR are present on the surface or inside of cells in a tissue that targeted for removal, such as tumors, glandular (e.g. prostate) hyperplasia, warts, and unwanted fatty tissue. While the surface antigens are more efficiently recognized and bound by the ASTR of CARs, intracellular antigens may also be targeted by the CARs. In some embodiments, the target antigens are preferably specific for cancer, inflammatory disease, neuronal-disorders, diabetes, cardiovascular disease, or infectious diseases. Examples of target antigens include antigens expressed by various immune cells, carcinomas, sarcomas, lymphomas, leukemia, germ cell tumors, blastomas, and cells associated with various hematologic diseases, autoimmune diseases, and/or inflammatory diseases.

Antigens specific for cancer which may be targeted by the ASTR include one or more of 4-IBB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2 or vimentin.

Antigens specific for inflammatory diseases which may be targeted by the ASTR include one or more of AOC3 (VAP-1), CAM-3001, CCL11 (eotaxin-1), CD125, CD147 (basigin), CD154 (CD40L), CD2, CD20, CD23 (IgE receptor), CD25 (a chain of IL-2 receptor), CD3, CD4, CD5, IFN-a, IFN-γ, IgE, IgE Fc region, IL-1, IL-12, IL-23, IL-13, IL-17, IL-17A, IL-22, IL-4, IL-5, IL-6, IL-6 receptor, integrin a4, integrin α4β7, *Lama glama*, LFA-1 (CD1 la), MEDI-528, myostatin, OX-40, rhuMAb β7, sclerostin, SOST, TGF beta 1, TNF-a or VEGF-A.

Antigens specific for neuronal disorders which may be targeted by the ASTR of the invention include one or more of beta amyloid or MABT5102A. Antigens specific for diabetes which may be targeted by the ASTR of the invention include one or more of L-Iβ or CD3. Antigens specific for cardiovascular diseases which may be targeted by the ASTR of the invention include one or more of C5, cardiac myosin, CD41 (integrin alpha-lib), fibrin II, beta chain, ITGB2 (CD 18) and sphingosine-1-phosphate.

Antigens specific for infectious diseases which may be targeted by the ASTR of the invention include one or more of anthrax toxin, CCR5, CD4, clumping factor A, cytomegalovirus, cytomegalovirus glycoprotein B, endotoxin, *Escherichia coli*, hepatitis B surface antigen, hepatitis B virus, HIV-1, Hsp90, Influenza A hemagglutinin, lipoteichoic acid, *Pseudomonas aeruginosa*, rabies virus glycoprotein, respiratory syncytial virus and TNF-a.

Further examples of target antigens include surface proteins found on cancer cells in a specific or amplified fashion, e.g. the IL-14 receptor, CD19, CD20 and CD40 for B-cell lymphoma, the Lewis Y and CEA antigens for a variety of carcinomas, the Tag72 antigen for breast and colorectal cancer, EGF-R for lung cancer, folate binding protein and the HER-2 protein which is often amplified in human breast and ovarian carcinomas, or viral proteins, e.g. gp120 and gp41 envelope proteins of HIV, envelope proteins from the Hepatitis B and C viruses, glycoprotein B and other envelope glycoproteins of human cytomegalovirus, and the envelope proteins from oncoviruses such as Kaposi's sarcoma-associated Herpes virus. Other potential target antigens include CD4, where the ligand is the HIV gp120 envelope glycoprotein, and other viral receptors, for example ICAM, which is the receptor for the human rhinovirus, and the related receptor molecule for poliovirus.

In another embodiment, the CAR may target antigens that engage cancer-treating cells, such as NK cells and other cells mentioned herein, to activate the cancer-treating cells by acting as immune effector cells. One example of this is a CAR that targets the CD16A antigen to engage NK cells to fight CD30-expressing malignancies. The bispecific, tetravalent AFM13 antibody is an example of an antibody that can deliver this effect. Further details of this type of embodiment can be found, for example, in Rothe, A., et al., "A phase 1 study of the bispecific anti-CD30/CD16A antibody construct AFM13 in patients with relapsed or refractory Hodgkin lymphoma," *Blood*, 25 Jun. 2015, Vl. 125, no. 26, pp. 4024-4031.

The extracellular spacer domain of the CAR is a hydrophilic region which is located between the ASTR and the transmembrane domain. In some embodiments, this domain facilitates proper protein folding for the CAR. The extracellular spacer domain is an optional component for the CAR. The extracellular spacer domain may include a domain selected from Fc fragments of antibodies, hinge regions of antibodies, CH2 regions of antibodies, CH3 regions of antibodies, artificial spacer sequences or combinations thereof. Examples of extracellular spacer domains include CD8a hinge, artificial spacers made of polypeptides which may be as small as, three glycines (Gly), as well as CH1 and CH3 domains of IgGs (such as human IgG4).

The transmembrane domain of the CAR is a region that is capable of spanning the plasma membrane of the cytotoxic cells. The transmembrane domain is selected from a transmembrane region of a transmembrane protein such as, for example, Type I transmembrane proteins, an artificial hydrophobic sequence or a combination thereof. Examples of the transmembrane domain include the transmembrane regions of the alpha, beta or zeta chain of the T cell receptor, CD28, CD3 epsilon, CD45, CD4, CD5, CD8, CD9, CD16, CD22, CD33, CD37, CD64, CD80, CD86, CD134, CD137, CD154. Synthetic transmembrane domains may include a triplet of phenylalanine, tryptophan and valine. Optionally, a short oligo- or polypeptide linker, preferably between 2 and 10 amino acids in length, may form the linkage between the transmembrane domain and the intracellular signaling domain of the CAR. A glycine-serine doublet provides a particularly suitable linker between the transmembrane domain and the intracellular signaling domain.

The CAR of the invention also includes an intracellular signaling domain. The intracellular signaling domain transduces the effector function signal and directs the cytotoxic cell to perform its specialized function, i.e., harming and/or destroying the target cells. Examples of the intracellular signaling domain include the chain of the $\zeta$ cell receptor complex or any of its homologs, e.g., $\eta$ chain, FcsRly and $\beta$ chains, MB 1 (Iga) chain, B29 (Ig) chain, etc., human CD3 zeta chain, CD3 polypeptides ($\Delta$, $\delta$ and $\epsilon$), syk family tyrosine kinases (Syk, ZAP 70, etc.), src family tyrosine kinases (Lck, Fyn, Lyn, etc.) and other molecules involved in T cell transduction, such as CD2, CD5 and CD28. Specifically, the intracellular signaling domain may be human CD3 zeta chain, FcyRIII, FcsRI, cytoplasmic tails of Fc receptors, an immunoreceptor tyrosine-based activation motif (ITAM) bearing cytoplasmic receptors and combinations thereof.

The intracellular signaling domains used in the CAR may include intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (Park et al., "Are all chimeric antigen receptors created equal?" *J Clin Oncol*., vol. 33, pp. 651-653, 2015). Additionally intracellular signaling domains include signaling domains used by NK and NKT cells (Hermanson, et al., "Utilizing chimeric antigen receptors to direct natural killer cell activity," *Front Immunol*., vol. 6, p. 195, 2015) such as signaling domains of NKp30 (B7-H6) (Zhang et al., "An NKp30-based chimeric antigen receptor promotes T cell effector functions and antitumor efficacy in vivo," *J Immunol*., vol. 189, pp. 2290-2299, 2012), and DAP12 (Topfer et al., "DAP12-based activating chimeric antigen receptor for NK cell tumor immunotherapy," *J Immunol*., vol. 194, pp. 3201-3212, 2015), NKG2D, NKp44, NKp46, DAP10, and CD3z. Additionally intracellular signaling domains also includes signaling domains of human Immunoglobulin receptors that contain immunoreceptor tyrosine based activation motif (ITAM) such as FcgammaRI, FcgammaRIIA, FcgammaRIIC, FcgammaRIIIA, FcRL5 (Gillis et al., "Contribution of Human FcγRs to Disease with Evidence from Human Polymorphisms and Transgenic Animal Studies," *Front Immunol*., vol. 5, p. 254, 2014).

In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79*b*, or CD66d. It is particularly preferred that the intracellular signaling domain in the CAR includes a cytoplasmic signaling domain of human CD3 zeta.

The CAR of the present invention may include a co-stimulatory domain, which has the function of enhancing cell proliferation, cell survival and development of memory cells for the cytotoxic cells that express the CAR. The CAR of the invention may include one or more co-stimulatory domains selected from co-stimulatory domains of proteins in the TNFR superfamily, CD28, CD137 (4-1BB), CD134 (OX40), DaplO, CD27, CD2, CD7, CD5, ICAM-1, LFA-1 (CD1 la/CD18), Lck, TNFR-I, PD-1, TNFR-II, Fas, CD30, CD40, ICOS LIGHT, NKG2C, B7-H3, or combinations thereof. If the CAR includes more than one co-stimulatory domain, these domains may be arranged in tandem, optionally separated by a linker. The co-stimulatory domain is an intracellular domain that may locate between the transmembrane domain and the intracellular signaling domain in the CAR.

In some embodiments, two or more components of the CAR of the invention are separated by one or more linkers. For example, in a CAR including at least two ASTRs, the two ASTRs may be separated by a linker. Linkers are oligo- or polypeptide regions of from about 1 to 100 amino acids in length. In some embodiments, the linkers may be, for example, 5-12 amino acids in length, 5-15 amino acids in length or 5 to 20 amino acids in length. Linkers may be composed of flexible residues like glycine and serine so that the adjacent protein domains are free to move relative to one another. Longer linkers, for example those longer than 100 amino acids, may be used in connection with alternate embodiments of the invention, and may be selected to, for example, ensure that two adjacent domains do not sterically interfere with one another. Examples of linkers which may be used in the instant invention include but are not limited to 2A linkers (for example T2A), 2A-like linkers or functional equivalents thereof.

Conditionally Active Antigen Specific Targeting Region

The CARs are chimeric proteins that are generated by fusing all the different domains discussed above together to form a fusion protein. The CAR is typically generated by an expression vector including polynucleotide sequences that encode the different domains of the CAR. The ASTR of the present invention, which functions to recognize and bind with an antigen on target cells, is conditionally active. Specifically, the ASTR is less active or inactive at a normal physiological condition and active at an aberrant condition for binding with the target antigen, in comparison with an ASTR of the corresponding wild-type protein. The present invention provides a method to generate the conditionally active ASTR from a wild-type protein or its binding domain (wild-type ASTR).

The wild-type protein that suitable to be used in whole or in part for at least its binding domain for the target antigen, as an ASTR in the present invention may be discovered by generating a protein library and screening the library for a protein with a desired binding affinity to the target antigen. The wild-type protein may be discovered by screening a cDNA library. A cDNA library is a combination of cloned cDNA (complementary DNA) fragments inserted into a collection of host cells, which together constitute some portion of the transcriptome of the organism. cDNA is produced from fully transcribed mRNA and therefore contains the coding sequence for expressed proteins of an organism. The information in cDNA libraries is a powerful and useful tool for discovery of proteins with desired properties by screening the libraries for proteins with the desired binding affinity to the target antigen.

In some embodiments where the wild-type proteins are antibodies, the wild-type antibodies can be discovered by generating and screening antibody libraries. The antibody libraries can be either polyclonal antibody libraries or monoclonal antibody libraries. A polyclonal antibody library against a target antigen can be generated by direct injection of the antigen into an animal or by administering the antigen to a non-human animal. The antibodies so obtained represent a library of polyclonal antibodies that bind to the antigen. For preparation of monoclonal antibody libraries, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96). Techniques described for the generating single chain antibodies (see, e.g., U.S. Pat. No. 4,946,778) can be adapted to produce single chain antibody library.

There are other methods for generation and screening of antibody libraries for discovery of the wild-type antibody. For example, fully human antibody display libraries can be utilized. Such a library is a population of antibodies displayed on the surface of host cell(s). Preferably, the antibody library is representative of the human repertoire of antibodies in that they have the capability of binding to a wide range of antigens. Because the antibodies are displayed on the surface of cells, the effective affinity (due to avidity) of each antibody in the library is increased. Unlike other popular library types, such as phage display libraries, where avidity of the antibodies for screening and identification purposes is less desirable, the super avidity provided by cell surface display in the present invention, is desirable. Cell surface display libraries enable the identification of low, medium and high binding affinity antibodies, as well as the identification of non-immunogenic and weak epitopes in the screening or selection step.

Generation of Evolved Molecules from Parent Molecule

The wild-type protein, or its binding domain (wild-type ASTR) undergoes a process of mutagenesis to produce a population of mutant polypeptides, which can then be screened to identify a mutant ASTR with an enhanced binding affinity to the target antigen at an aberrant condition, and optionally, substantially the same or a reduction in binding affinity to the target antigen at a normal physiological condition, in comparison with the wild-type ASTR.

Any chemical synthetic or recombinant mutagenic method may be used to generate the population of mutant polypeptides. The practice of the present invention may employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Cabs eds., 1987, Cold Spring Harbor Laboratory); Methods In Enzymnology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The disclosure provides for a method for generating a nucleic acid mutant encoding a mutant polypeptide being conditionally active, the method including modifying the nucleic acid by (i) substituting one or more nucleotides for a different nucleotide, wherein the nucleotide includes a natural or non-natural nucleotide; (ii) deleting one or more nucleotides, (iii) adding one or more nucleotides, or (iv) any combination thereof. In one aspect, the non-natural nucleotide includes inosine. In another aspect, the method further includes assaying the polypeptides encoded by the modified nucleic acids for altered enzyme activity, thereby identifying the modified nucleic acid(s) encoding a polypeptide having altered enzyme activity. In one aspect, the modifications of step (a) are made by PCR, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturated mutagenesis, ligase chain reaction, in vitro mutagenesis, ligase chain reaction, oligonucleotide synthesis, any DNA-generating technique and any combination thereof. In another aspect, the method further includes at least one repetition of the modifying step.

The disclosure further provides a method for making a polynucleotide from two or more nucleic acids, the method including: (a) identifying regions of identity and regions of diversity between two or more nucleic acids, wherein at least one of the nucleic acids includes a nucleic acid of the disclosure; (b) providing a set of oligonucleotides which correspond in sequence to at least two of the two or more nucleic acids; and, (c) extending the oligonucleotides with a polymerase, thereby making the polynucleotide.

Any technique of mutagenesis can be employed in various embodiments of the disclosure. Stochastic or random mutagenesis is exemplified by a situation in which a parent molecule is mutated (modified or changed) to yield a set of progeny molecules having mutation(s) that are not predetermined. Thus, in an in vitro stochastic mutagenesis reaction, for example, there is not a particular predetermined product whose production is intended; rather there is an uncertainty—hence randomness—regarding the exact nature of the mutations achieved, and thus also regarding the products generated. Stochastic mutagenesis is manifested in processes such as error-prone PCR and stochastic shuffling, where the mutation(s) achieved are random or not predetermined. The variant forms can be generated by error-prone transcription, such as an error-prone PCR or use of a polymerase which lacks proof-reading activity (see, Liao (1990) Gene 88: 107-111), of the first variant form, or, by replication of the first form in a mutator strain (mutator host cells are discussed in further detail below, and are generally well known). A mutator strain can include any mutants in any organism impaired in the functions of mismatch repair. These include mutant gene products of mutS, mutT, mutH, mutL, ovrD, dcm, vsr, umuC, umuD, sbcB, recJ, etc. The impairment is achieved by genetic mutation, allelic replacement, selective inhibition by an added reagent such as a small compound or an expressed antisense RNA, or other techniques. Impairment can be of the genes noted, or of homologous genes in any organism.

Other mutagenesis methods include oligonucleotide-directed mutagenesis technologies, error-prone polymerase chain reactions (error-prone PCR) and cassette mutagenesis, in which a specific region of the parental polynucleotide is replaced with a synthetically mutagenized oligonucleotide. In these cases, a number of mutant sites are generated around certain sites in the parental sequence.

In oligonucleotide-directed mutagenesis, a short sequence is replaced with a synthetically mutagenized oligonucleotide. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfate, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid polynucleotides so mutagenized are introduced into *E. coli* and propagated as a pool or library of hybrid plasmids.

Error-prone PCR uses low-fidelity polymerization conditions to introduce a low level of point mutations randomly over a long sequence. In a mixture of fragments of unknown sequence, error-prone PCR can be used to mutagenize the mixture.

In cassette mutagenesis, a sequence block of a single template is typically replaced by a (partially) randomized sequence. Reidhaar-Olson J F and Sauer R T: Combinatorial cassette mutagenesis as a probe of the informational content of protein sequences. *Science* 241(4861):53-57, 1988.

Alternatively, any technique of non-stochastic or non-random mutagenesis can be employed in various embodiments of the disclosure. Non-stochastic mutagenesis is exemplified by a situation in which a parent molecule is mutated (modified or changed) to yield a progeny molecule having one or more predetermined mutations. It is appreciated that the presence of background products in some quantity is a reality in many reactions where molecular processing occurs, and the presence of these background products does not detract from the non-stochastic nature of a mutagenesis process having a predetermined product. Site-saturation mutagenesis and synthetic ligation reassembly, are examples of mutagenesis techniques where the exact chemical structure(s) of the intended product(s) are predetermined.

One method of site-saturation mutagenesis is disclosed in U.S. patent application publication 2009/0130718 This method provides a set of degenerate primers corresponding to codons of a template polynucleotide, and performs polymerase elongation to produce progeny polynucleotides, which contain sequences corresponding to the degenerate primers. The progeny polynucleotides can be expressed and screened for directed evolution. Specifically, this is a method for producing a set of progeny polynucleotides, including the steps of (a) providing copies of a template polynucleotide, each including a plurality of codons that encode a template polypeptide sequence; and (b) for each codon of the template polynucleotide, performing the steps of (1) providing a set of degenerate primers, where each primer includes a degenerate codon corresponding to the codon of the template polynucleotide and at least one adjacent sequence that is homologous to a sequence adjacent to the codon of the template polynucleotide; (2) providing conditions allowing the primers to anneal to the copies of the template polynucleotides; and (3) performing a polymerase elongation reaction from the primers along the template; thereby producing progeny polynucleotides, each of which contains a sequence corresponding to the degenerate codon of the annealed primer; thereby producing a set of progeny polynucleotides. Site-saturation mutagenesis relates to the directed evolution of nucleic acids and screening of clones containing the evolved nucleic acids for resultant binding activity of interest.

Site saturation mutagenesis relates generally to a method of: 1) preparing a progeny generation of molecule(s) (including a molecule that is included of a polynucleotide sequence, a molecule that is included of a polypeptide sequence, and a molecule that is included in part of a polynucleotide sequence and in part of a polypeptide sequence), that is mutagenized to achieve at least one point mutation, addition, deletion, and/or chimerization, from one or more ancestral or parental generation template(s); 2) screening the progeny generation molecule(s)—preferably using a high throughput method—for desired binding affinity to the target antigen; 3) optionally obtaining &/or cataloguing structural &/or and functional information regarding the parental &/or progeny generation molecules; and 4) optionally repeating any of steps 1) to 3).

In site saturation mutagenesis, there is generated (e.g. from a parent polynucleotide template)—in what is termed "codon site-saturation mutagenesis"—a progeny generation of polynucleotides, each having at least one set of up to three contiguous point mutations (i.e. different bases including a new codon), such that every codon (or every family of degenerate codons encoding the same amino acid) is represented at each codon position. Corresponding to—and encoded by—this progeny generation of polynucleotides, there is also generated a set of progeny polypeptides, each having at least one single amino acid point mutation. In a preferred aspect, there is generated—in what is termed "amino acid site-saturation mutagenesis"-one such mutant polypeptide for each of the 19 naturally encoded polypeptide-forming alpha-amino acid substitutions at each and every amino acid position along the polypeptide. This yields—for each and every amino acid position along the parental polypeptide—a total of 20 distinct progeny polypeptides including the original amino acid, or potentially more than 21 distinct progeny polypeptides if additional amino acids are used either instead of or in addition to the 20 naturally encoded amino acids.

Other mutagenesis techniques can also be employed which involve recombination and more specifically a method for preparing polynucleotides encoding a polypeptide by a method of in vivo re-assortment of polynucleotide sequences containing regions of partial homology, assembling the polynucleotides to form at least one polynucleotide and screening the polynucleotides for the production of polypeptide(s) having a useful property.

In another aspect, mutagenesis techniques exploit the natural property of cells to recombine molecules and/or to mediate reductive processes that reduce the complexity of sequences and extent of repeated or consecutive sequences possessing regions of homology.

Various mutagenesis techniques can be used alone or in combination to provide a method for generating hybrid polynucleotides encoding biologically active hybrid polypeptides. In accomplishing these and other objects, there has been provided, in accordance with one aspect of the disclosure, a method for introducing polynucleotides into a suitable host cell and growing the host cell under conditions that produce hybrid polypeptides.

Chimeric genes have been made by joining 2 polynucleotide fragments using compatible sticky ends generated by restriction enzyme(s), where each fragment is derived from a separate progenitor (or parental) molecule. Another example is the mutagenesis of a single codon position (i.e. to achieve a codon substitution, addition, or deletion) in a parental polynucleotide to generate a single progeny polynucleotide encoding for a single site-mutagenized polypeptide.

Further, in vivo site specific recombination systems have been utilized to generate hybrids of genes, as well as random methods of in vivo recombination, and recombination between homologous but truncated genes on a plasmid. Mutagenesis has also been reported by overlapping extension and PCR.

Non-random methods have been used to achieve larger numbers of point mutations and/or chimerizations, for example comprehensive or exhaustive approaches have been used to generate all the molecular species within a particular grouping of mutations, for attributing functionality to specific structural groups in a template molecule (e.g. a specific single amino acid position or a sequence included of two or more amino acids positions), and for categorizing and comparing specific grouping of mutations.

Any of these or other methods of evolving can be employed in the present disclosure to generate a new population of mutant polypeptides (library) from the wild-type protein.

Expression of Evolved Molecules

The mutant polynucleotides generated from the evolving step may, or may not be size fractionated on an agarose gel according to published protocols, inserted into an expression vector, and transfected into an appropriate host cell to produce the mutant polypeptides (expression). The expression may use routine molecular biology techniques. Thus, the expression step can use various known methods.

For example, briefly, mutant polynucleotides generated from the evolving step are then digested and ligated into an expression vector, such as plasmid DNA using standard molecular biology techniques. The vector is then transformed into bacteria or other cells using standard protocols. This can be done in an individual well of a multi-well tray, such as a 96-well tray for high throughput expression and screening. The process is repeated for each mutant polynucleotide.

Polynucleotides selected and isolated as described are introduced into a suitable host cell. A suitable host cell is any cell which is capable of promoting recombination and/or reductive reassortment. The selected polynucleotides are preferably already in a vector which includes appropriate control sequences. The host cell can be a higher eukaryotic cell, such as a mammalian cell, or a lower eukaryotic cell, such as a yeast cell, or preferably, the host cell can be a prokaryotic cell, such as a bacterial cell. Introduction of the construct into the host cell can be effected by calcium phosphate transfection, DEAE-Dextran mediated transfection, or electroporation (e.g. Ecker and Davis, 1986, Inhibition of gene expression in plant cells by expression of antisense RNA, *Proc Natl Acad Sci USA*, 83:5372-5376).

As representative examples of expression vectors which may be used, there may be mentioned viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), Pl-based artificial chromosomes, yeast plasmids, yeast artificial chromosomes, and any other vectors specific for specific hosts of interest (such as *bacillus, aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Low copy number or high copy number vectors may be employed with the present disclosure.

The mutant polynucleotide sequence in the expression vector is operatively linked to an appropriate expression control sequence(s) (promoter) to direct RNA synthesis. Particular named bacterial promoters include lad, lacZ, T3, T7, gpt, lambda PR, PL and trp. Eukaryotic promoters include CMV immediate early, HSV thymidine kinase, early and late SV40, LTRs from retrovirus, and mouse metallothionein-1. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using chloramphenicol transferase (CAT) vectors or other vectors with selectable markers. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

Eukaryotic DNA transcription can be increased by inserting an enhancer sequence into the expression vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The expression vectors containing the DNA segments of interest can be transferred into host cells by well-known methods, depending on the type of cell production hosts. For example, calcium chloride transfection is commonly utilized for prokaryotic host cells, whereas calcium phosphate treatment, lipofection, or electroporation may be used for eukaryotic host cells. Other methods used to transform mammalian cell production hosts include the use of polybrene, protoplast fusion, liposomes, electroporation, and microinjection (see, generally, Sambrook et al., supra).

Once the expression vector has been introduced into an appropriate host, the host is maintained under conditions suitable for high level expression of the introduced mutant polynucleotide sequences to produce the mutant polypeptides. The expression vector is typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362).

Therefore, in another aspect of the disclosure, mutant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

The cells are then propagated and "reductive reassortment" is effected. The rate of the reductive reassortment process may be stimulated by the introduction of DNA damage if desired, in vivo reassortment is focused on "inter-molecular" processes collectively referred to as "recombination" which in bacteria, is generally viewed as a "RecA-dependent" phenomenon. The disclosure can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process. The end result is a reassortment of the molecules into all possible combinations.

In one aspect, the host organism or cell includes a gram negative bacterium, a gram positive bacterium or a eukaryotic organism. In another aspect of the disclosure, the gram negative bacterium includes *Escherichia coli*, or *Pseudomonas fluorescens*. In another aspect of the disclosure, the gram positive bacterium include *Streptomyces diversa, Lactobacillus gasseri, Lactococcus lactis, Lactococcus cremoris*, or *Bacillus subtilis*. In another aspect of the disclosure, the eukaryotic organism includes *Saccharomyces cerevisiae, Schizosaccharomyces pombe, Pichia pastoris, Kluyveromyces lactis, Hansenula plymorpha*, or *Aspergillus niger*. As representative examples of appropriate hosts, there may be mentioned: bacterial cells, such as *E. coli, Streptomyces, Salmonella typhimurium*; fungal cells, such as yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

In addition to eukaryotic microorganisms such as yeast, mammalian tissue cell culture may also be used to express the mutant polypeptides of the present invention (see, Winnacker, "From Genes to Clones," VCH Publishers, N.Y., N.Y. (1987)). Eukaryotic cells are preferred, because a number of suitable host cell lines capable of secreting intact immunoglobulins have been developed in the art, and include the CHO cell lines, various COS cell lines, HeLa cells, myeloma cell lines, B-cells or hybridomas. Expression vectors for these cells can include expression control sequences, such as an origin of replication, a promoter, an enhancer (Queen et al., *Immunol. Rev.*, vol. 89, page 49, 1986), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

In one embodiment, the eukaryotic host cells are selected from CHO, HEK293, IM9, DS-1, THP-1, Hep G2, COS, NIH 3T3, C33a, A549, A375, SK-MEL-28, DU 145, PC-3, HCT 116, Mia PACA-2, ACHN, Jurkat, MM1, Ovcar 3, HT 1080, Panc-1, U266, 769P, BT-474, Caco-2, HCC 1954, MDA-MB-468, LnCAP, NRK-49F, and SP2/0 cell lines; and mouse splenocytes and rabbit PBMC. In one aspect, the mammalian hoist cell is selected from a CHO or HEK293 cell line. In one specific aspect, the mammalian host cell is a CHO-S cell line. In another specific aspect, the mammalian system is a HEK293 cell line. In another embodiment, the eukaryotic host is a yeast cell system. In one aspect, the eukaryotic host is selected from *S. cerevisiae* yeast cells or picchia yeast cells.

In another embodiment, mammalian host cells may be created commercially by a contract research or custom manufacturing organization. For example, for recombinant antibodies or other proteins, Lonza (Lonza Group Ltd, Basel, Switzerland) can create vectors to express these products using the GS Gene Expression System™ technology with either CHOK1SV or NS0 cell production hosts. Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan.

As discussed above, expression optimization for the conditionally active ASTR can be achieved by optimization of vectors used (vector components, such as promoters, splice sites, 5' and 3' termini and flanking sequences), gene modification of host cells to reduce gene deletions and rearrangements, evolution of host cell gene activities by in vivo or in vitro methods of evolving relevant genes, optimization of host glycosylating enzymes by evolution of relevant genes, and/or by chromosome wide host cell mutagenesis and selection strategies to select for cells with enhanced expression capabilities.

Protein expression can be induced by a variety of known methods, and many genetic systems have been published for induction of protein expression. For example, with appropriate systems, the addition of an inducing agent will induce protein expression. Cells are then pelleted by centrifugation and the supernatant removed. Periplasmic protein can be enriched by incubating the cells with DNAse, RNAse, and lysozyme. After centrifugation, the supernatant, containing the new protein, is transferred to a new multi-well tray and stored prior to assay.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps. The screening of a conditionally active ASTR can be aided by the availability of a convenient high throughput screening or selection process. Cell surface display expression and screening technology (for example, as defined above) can be employed to screen mutant proteins for conditionally active ASTR.

Screening of Mutants to Identify Reversible or Nonreversible Mutants

Identifying desirable molecules is most directly accomplished by measuring protein activity at the permissive condition and the wild type condition. The mutants with the largest ratio of activity (permissive/wild type) can then be selected and permutations of the point mutations are generated by combining the individual mutations using standard methods. The combined permutation protein library is then screened for those proteins displaying the largest differential activity between the permissive and wild type condition.

Activity of supernatants can be screened using a variety of methods, for example using high throughput activity assays, such as fluorescence assays, to identify protein mutants that are sensitive at whatever characteristic one desires (temperature, pH, etc). For example, to screen for temporally sensitive mutants, the enzymatic or antibody activity of each individual mutant is determined at lower temperatures (such as 25 degrees Celsius), and at temperatures which the original protein functions (such as 37 degrees Celsius), using commercially available substrates. Screening can be carried out in a variety of media such as serum and BSA, among others. Reactions can initially be performed in a multi well assay format, such as a 96-well assay, and confirmed using a different format, such as a 14 ml tube format.

In one aspect, the method further includes modifying at least one of the nucleic acids or polypeptides prior to testing the candidates for conditional biologic activity, in another aspect, the testing of step (c) further includes testing for improved expression of the polypeptide in a host cell or host organism, in a further aspect, the testing of step (c) further includes testing for enzyme activity within a pH range from about pH 3 to about pH 12. In a further aspect, the testing of step (c) further includes testing for enzyme activity within a pH range from about pH 5 to about pH 10. In a further aspect, the testing of step (c) further includes testing for enzyme activity within a pH range from about pH 6 to about pH 8. In a further aspect, the testing of step (c) further includes testing for enzyme activity at pH 6.7 and pH 7.5. In another aspect, the testing of step (c) further includes testing for enzyme activity within a temperature range from about 4 degrees C. to about 55 degrees C. In another aspect, the testing of step (c) further includes testing for enzyme activity within a temperature range from about 15 degrees C. to about 47 degrees C. In another aspect, the testing of step (c) further includes testing for enzyme activity within a temperature range from about 20 degrees C. to about 40 degrees C. In another aspect, the testing of step (c) further includes testing for enzyme activity at the temperatures of 25 degrees C. and 37 degrees C. In another aspect, the testing of step (c) further includes testing for enzyme activity under normal osmotic pressure, and aberrant (positive or negative) osmotic pressure, In another aspect, the testing of step (c) further includes testing for enzyme activity under normal electrolyte concentration, and aberrant (positive or negative) electrolyte concentration. The electrolyte concentration to be tested is selected from one of calcium, sodium, potassium, magnesium, chloride, bicarbonate and phosphate concentration, in another aspect, the testing of step (c) further includes testing for enzyme activity which results in a stabilized reaction product.

In another aspect, the disclosure provides for a purified antibody that specifically binds to the polypeptide of the disclosure or a fragment thereof, having enzyme activity. In one aspect, the disclosure provides for a fragment of the antibody that specifically binds to a polypeptide having enzyme activity.

Antibodies and Antibody-Based Screening Methods

The disclosure provides isolated or recombinant antibodies that specifically bind to an enzyme of the disclosure. These antibodies can be used to isolate, identify or quantify the enzymes of the disclosure or related polypeptides. These antibodies can be used to isolate other polypeptides within the scope the disclosure or other related enzymes. The antibodies can be designed to bind to an active site of an enzyme. Thus, the disclosure provides methods of inhibiting enzymes using the antibodies of the disclosure.

The antibodies can be used in immunoprecipitation, staining, immunoaffinity columns, and the like. If desired, nucleic acid sequences encoding for specific antigens can be generated by immunization followed by isolation of polypeptide or nucleic acid, amplification or cloning and immobilization of polypeptide onto an array of the disclosure. Alternatively, the methods of the disclosure can be used to modify the structure of an antibody produced by a cell to be modified, e.g., an antibody's affinity can be increased or decreased. Furthermore, the ability to make or modify antibodies can be a phenotype engineered into a cell by the methods of the disclosure.

Methods of immunization, producing and isolating antibodies (polyclonal and monoclonal) are known to those of skill in the art and described in the scientific and patent literature, see, e.g., Coligan, CURRENT PROTOCOLS IN IMMUNOLOGY, Wiley/Greene, N Y (1991); Stites (eds.) BASIC AND CLINICAL IMMUNOLOGY (7th ed.) Lange Medical Publications, Los Altos, Calif. ("Stites"); Goding, MONOCLONAL ANTIBODIES: PRINCIPLES AND PRACTICE (2d ed.) Academic Press, New York, N.Y. (1986); Kohler (1975) "Continuous cultures of fused cells secreting antibody of predefined specificity", Nature 256: 495; Harlow (1988) ANTIBODIES, A LABORATORY MANUAL, Cold Spring Harbor Publications, New York. Antibodies also can be generated in vitro, e.g., using recombinant antibody binding site expressing phage display libraries, in addition to the traditional in vivo methods using animals. See, e.g., Hoogenboom (1997) "Designing and optimizing library selection strategies for generating high-affinity antibodies", *Trends Biotechnol.* 15:62-70; and Katz (1997) "Structural and mechanistic determinants of affinity and specificity of ligands discovered or engineered by phage display", *Annu. Rev. Biophys. Biomol. Struct.* 26:27-45.

Polypeptides or peptides can be used to generate antibodies which bind specifically to the polypeptides, e.g., the enzymes, of the disclosure. The resulting antibodies may be used in immunoaffinity chromatography procedures to isolate or purify the polypeptide or to determine whether the polypeptide is present in a biological sample. In such procedures, a protein preparation, such as an extract, or a biological sample is contacted with an antibody capable of specifically binding to one of the polypeptides of the disclosure.

In immunoaffinity procedures, the antibody is attached to a solid support, such as a bead or other column matrix. The protein preparation is placed in contact with the antibody under conditions in which the antibody specifically binds to one of the polypeptides of the disclosure. After a wash to remove non-specifically bound proteins, the specifically bound polypeptides are eluted.

The ability of proteins in a biological sample to bind to the antibody may be determined using any of a variety of procedures familiar to those skilled in the art. For example, binding may be determined by labeling the antibody with a detectable label such as a fluorescent agent, an enzymatic label, or a radioisotope. Alternatively, binding of the antibody to the sample may be detected using a secondary antibody having such a detectable label thereon. Particular assays include ELISA assays, sandwich assays, radioimmunoassays, and Western Blots.

Polyclonal antibodies generated against the polypeptides of the disclosure can be obtained by direct injection of the polypeptides into an animal or by administering the polypeptides to a non-human animal. The antibody so obtained will then bind the polypeptide itself. In this manner, even a sequence encoding only a fragment of the polypeptide can be used to generate antibodies which may bind to the whole native polypeptide. Such antibodies can then be used to isolate the polypeptide from cells expressing that polypeptide.

For preparation of monoclonal antibodies, any technique which provides antibodies produced by continuous cell line cultures can be used. Examples include the hybridoma technique, the trioma technique, the human B-cell hybridoma technique, and the EBV-hybridoma technique (see, e.g., Cole (1985) in Monoclonal Antibodies and Cancer Therapy, Alan R. Liss, Inc., pp. 77-96).

Techniques described for the production of single chain antibodies (see, e.g., U.S. Pat. No. 4,946,778) can be adapted to produce single chain antibodies to the polypeptides of the disclosure. Alternatively, transgenic mice may be used to express humanized antibodies to these polypeptides or fragments thereof. Antibodies generated against the polypeptides of the disclosure may be used in screening for similar polypeptides (e.g., enzymes) from other organisms and samples. In such techniques, polypeptides from the organism are contacted with the antibody and those polypeptides which specifically bind the antibody are detected. Any of the procedures described above may be used to detect antibody binding.

Screening Methodologies and "on-Line" Monitoring Devices

In practicing the methods of the disclosure, a variety of apparatus and methodologies can be used to in conjunction with the polypeptides and nucleic acids of the disclosure, e.g., to screen polypeptides for enzyme activity, to screen compounds as potential modulators, e.g., activators or inhibitors, of an enzyme activity, for antibodies that bind to a polypeptide of the disclosure, for nucleic acids that hybridize to a nucleic acid of the disclosure, to screen for cells expressing a polypeptide of the disclosure and the like.

Arrays, or "Biochips"

Nucleic acids or polypeptides of the disclosure can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the disclosure. For example, in one aspect of the disclosure, a monitored parameter is transcript expression of an enzyme gene. One or more, or, all the transcripts of a cell can be measured by hybridization of a sample including transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays including genomic nucleic acid can also be used to determine the genotype of a newly engineered strain made by the methods of the disclosure. Polypeptide arrays" can also be used to simultaneously quantify a plurality of proteins. The present disclosure can be practiced with any known "array," also referred to as a "microarray" or "nucleic acid array" or "polypeptide array" or "antibody array" or "biochip," or variation thereof. Arrays are generically a plurality of "spots" or "target elements," each target element including a defined amount of one or more biological molecules, e.g., oligonucleotides, immobilized onto a defined area of a substrate surface for specific binding to a sample molecule, e.g., mRNA transcripts.

In practicing the methods of the disclosure, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) "Gene chips: Array of hope for understanding gene regulation", *Curr. Biol.* 8:R171-R174; Schummer (1997) "Inexpensive Handheld Device for the Construction of High-Density Nucleic Acid Arrays", *Biotechniques* 23:1087-1092; Kern (1997) "Direct hybridization of large-insert genomic clones on high-density gridded cDNA filter arrays", *Biotechniques* 23:120-124; Solinas-Toldo (1997) "Matrix-Based Comparative Genomic Hybridization: Biochips to Screen for Genomic Imbalances", *Genes, Chromosomes & Cancer* 20:399-407; Bowtell (1999) "Options Available—From Start to Finish~for Obtaining Expression Data by Microarray", *Nature Genetics Supp.* 21:25-32. See also published U.S. patent applications Nos. 20010018642; 20010019827; 20010016322; 20010014449; 20010014448; 20010012537; 20010008765.

Capillary Arrays

Capillary arrays, such as the GIGAMATRIX™ Diversa Corporation, San Diego, Calif., can be used in the methods of the disclosure. Nucleic acids or polypeptides of the disclosure can be immobilized to or applied to an array, including capillary arrays. Arrays can be used to screen for or monitor libraries of compositions (e.g., small molecules, antibodies, nucleic acids, etc.) for their ability to bind to or modulate the activity of a nucleic acid or a polypeptide of the disclosure. Capillary arrays provide another system for holding and screening samples. For example, a sample screening apparatus can include a plurality of capillaries formed into an array of adjacent capillaries, wherein each capillary includes at least one wall defining a lumen for retaining a sample. The apparatus can further include interstitial material disposed between adjacent capillaries in the array, and one or more reference indicia formed within of the interstitial material. A capillary for screening a sample, wherein the capillary is adapted for being bound in an array of capillaries, can include a first wall defining a lumen for retaining the sample, and a second wall formed of a filtering material, for filtering excitation energy provided to the lumen to excite the sample. A polypeptide or nucleic acid, e.g., a ligand, can be introduced into a first component into at least a portion of a capillary of a capillary array. Each capillary of the capillary array can include at least one wall defining a lumen for retaining the first component. An air bubble can be introduced into the capillary behind the first component. A second component can be introduced into the capillary, wherein the second component is separated from the first component by the air bubble. A sample of interest can be introduced as a first liquid labeled with a detectable particle into a capillary of a capillary array, wherein each capillary of the capillary array includes at least one wall defining a lumen for retaining the first liquid and the detectable particle, and wherein the at least one wall is coated with a binding material for binding the detectable particle to the at least one wall. The method can further include removing the first liquid from the capillary tube, wherein the bound detectable particle is maintained within the capillary, and introducing a second liquid into the capillary tube. The capillary array can include a plurality of individual capillaries including at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a micro titer plate having about 100,000 or more individual capillaries bound together.

Engineering Conditionally Active Antibodies

Conditionally active antibodies may be engineered to generate multispecific conditionally active antibodies. The multispecific antibody may be an antibody with polyepitopic specificity, as described in WO 2013/170168. Multispecific antibodies include, but are not limited to, an antibody including a heavy chain variable domain ($V_H$) and a light chain variable domain ($V_L$), where the $V_H V_L$ unit has polyepitopic specificity, antibodies having two or more $V_L$ and $V_H$ domains where each $V_H V_L$ unit binds to a different epitope, antibodies having two or more single variable domains with each single variable domain binding to a different epitope, and antibodies including one or more antibody fragments as well as antibodies including antibody fragments that have been linked covalently or non-covalently.

To construct multispecific antibodies, including bispecific antibodies, antibody fragments having at least one free sulfhydryl group are obtained. The antibody fragments may be obtained from full-length conditionally active antibodies. The conditionally active antibodies may be digested enzymatically to produce antibody fragments. Exemplary enzymatic digestion methods include, but are not limited to, pepsin, papain and Lys-C. Exemplary antibody fragments include, but are not limited to, Fab, Fab', F(ab')2, Fv, diabodies (Db); tandem diabodies (taDb), linear antibodies (see U.S. Pat. No. 5,641,870, Example 2; Zapata et al., *Protein Eng.*, vol. 8, pages 1057-1062 (1995)); one-armed antibodies, single variable domain antibodies, minibodies (Olafsen et al (2004) *Protein Eng. Design & Sel.*, vol. 17, pages 315-323), single-chain antibody molecules, fragments produced by a Fab expression library, anti-idiotypic (anti-Id) antibodies, complementary determining regions (CDRs), and epitope-binding fragments. Antibody fragments may also be produced using DNA recombinant technology. The DNA encoding the antibody fragments may be cloned into plasmid expression vectors or phagemid vectors and expressed directly in *E. Coli*. Antibody enzymatic digestion methods, DNA cloning and recombinant protein expression methods are well known to those skilled in the art.

Antibody fragments may be purified using conventional techniques and may be subjected to reduction to generate a free thiol group. Antibody fragments having a free thiol group may be reacted with a cross-linker, for example, bis-maleimide. Such crosslinked antibody fragments are purified and then reacted with a second antibody fragment having a free thiol group. The final product in which two antibody fragments are crosslinked is purified. In certain embodiments, each antibody fragment is a Fab and the final product, in which the two Fabs are linked through bis-maleimide, is referred to herein as bismaleimido-(thio-Fab) 2, or bis-Fab. Such multispecific antibodies and antibody analogs, including bis-Fabs, can be exploited to quickly synthesize a large number of antibody fragment combinations, or structural variants of native antibodies or particular antibody/fragment combinations.

Multispecific antibodies can be synthesized with modified cross-linkers such that additional functional moieties may be attached to the multispecific antibodies. Modified cross-linkers allow for attachment of any sulfhydryl-reactive moiety. In one embodiment, N-succinimidyl-S-acetylthioacetate (SATA) is attached to bis-maleimide to form bis-maleimido-acetylthioacetate (BMata). After deprotection of the masked thiol group, any functional group having a sulfhydryl-reactive (or thiol-reactive) moiety may be attached to the multispecific antibodies.

Exemplary thiol-reactive reagents include a multifunctional linker reagent, a capture, i.e. an affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). Such multispecific antibodies or antibody analogs having modified cross-linkers may be further reacted with a drug moiety reagent or other label. Reaction of a multispecific antibody or antibody analog with a drug-linker intermediate provides a multispecific antibody-drug conjugate or antibody analog-drug conjugate, respectively.

Other techniques for making multispecific antibodies may also be used in the present invention. References describing these techniques include: (1) Milstein and Cuello, Nature, vol. 305, page 537 (1983)), WO 93/08829, and Traunecker et al., *EMBO J.*, vol. 10, page 3655 (1991) on recombinant co-expression of two immunoglobulin heavy chain-light chain pairs having different specificities; (2) U.S. Pat. No. 5,731,168 on "knob-in-hole" engineering; (3) WO 2009/

089004A1 on engineering electrostatic steering effects for making antibody Fc-heterodimeric molecules; (4) U.S. Pat. No. 4,676,980, and Brennan et al., *Science*, vol. 229, page 81 (1985) on cross-linking two or more antibodies or fragments; (5) Kostelny et al., *J. Immunol.*, vol. 148, pages 1547-1553 (1992) on using leucine zippers to produce bi-specific antibodies; (6) Hollinger et al., *Proc. Natl. Acad. Sci. USA*, vol. 90, pages 6444-6448 (1993) on using "diabody" technology for making bispecific antibody fragments; (7) Gruber et al., *J. Immunol.*, vol. 152, page 5368 (1994) on using single-chain Fv (sFv) dimers; (8) Tutt et al. *J. Immunol.* 147: 60 (1991) on preparing trispecific antibodies; and (9) US 2006/0025576A1 and Wu et al. *Nature Biotechnology*, vol. 25, pages 1290-1297 (2007) on engineered antibodies with three or more functional antigen binding sites, including "Octopus antibodies" or "dual-variable domain immunoglobulins" (DVDs).

Multispecific antibodies of the present invention may also be generated as described in WO/2011/109726.

In one embodiment, a conditionally active antibody for crossing the blood-brain barrier (BBB) is engineered to make a multispecific antibody (e.g. a bispecific antibody). This multispecific antibody includes a first antigen binding site which binds a BBB-R and a second antigen binding site which binds a brain antigen. At least the first antigen binding site for BBB-R is conditionally active. A brain antigen is an antigen expressed in the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

The BBB has endogenous transport systems that are mediated by a BBB receptor (BBB-R), which is a specific receptor that allows transport of macromolecules across the BBB. For example, an antibody that can bind to a BBB-R may be transported across BBB using the endogenous transport systems. Such an antibody may serve as a vehicle for transport of drugs or other agents across BBB by using the endogenous BBB receptor mediated transport system that traverses the BBB. Such antibodies need not have high affinity to a BBB-R. Antibodies that are not conditionally active antibodies with low affinities for BBB-R have been described as crossing the BBB more efficiently than a high affinity antibody, as described in US 2012/0171120.

Another method for engineering antibodies to enter the brain is to engineer antibodies to be delivered to the brain via the central nervous system lymphatic vessels. Thus, the antibodies can be engineered to bind to or mimic immune cells such as T-cells, or synovial or cerebrospinal fluids that travel to the central nervous system via lymphatic vessels. Details of the lymphatic vessels of the central nervous system are described in, for example, Louveau, A., et al., "Structural and functional features of central nervous system lymphatic vessels," Nature 523, pp. 337-341, 16 Jul. 2015 and the articles citing this article that are publicly available as of the date of filing of this application.

Unlike traditional antibodies, conditionally active antibodies are not required to have low affinity for BBB-R to cross the BBB and remain inside the brain. Conditionally active antibodies can have high affinity for the BBB-R on the blood side of the BBB, and little or no affinity on the brain side of the BBB. Drugs, such as drug conjugates, may be coupled to a conditionally active antibody to be transported with the antibody across the BBB into the brain.

A BBB-R is a transmembrane receptor protein expressed on brain endothelial cells which is capable of transporting molecules across the blood-brain barrier. Examples of BBB-R include transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), and heparin-binding epidermal growth factor-like growth factor (HB-EGF). An exemplary BBB-R herein is a transferrin receptor (TfR). The TfR is a transmembrane glycoprotein (with a molecular weight of about 180,000) composed of two disulphide-bonded sub-units (each of apparent molecular weight of about 90,000) involved in iron uptake in vertebrates.

In some embodiments, the present invention provides a conditionally active antibody generated from a parent or wild-type antibody against a BBB-R. The conditionally active antibody binds the BBB-R on the blood side of the BBB, and has a lower affinity to the BBB-R than the parent or wild-type antibody on the brain side of the BBB. In some other embodiments, the conditionally active antibody has affinity to the BBB-R than the wild type or parent antibody on the blood side of the BBB, and has no affinity to the BBB-R on the brain side of the BBB.

Blood plasma is a body fluid that is very different from brain extracellular fluid (ECF). As discussed by Somjen ("Ions in the Brain: Normal Function, Seizures, and Stroke," Oxford University Press, 2004, pages 16 and 33) and Redzic ("Molecular biology of the blood-brain and the blood-cerebrospinal fluid barriers: similarities and differences," *Fluids and Barriers of the CNS*, vol. 8:3, 2011), the brain extracellular fluid has significantly less $K^+$, more $Mg^{2+}$ and $H^+$ than blood plasma. The differences in ion concentrations between blood plasma and brain ECF lead to significant differences in osmotic pressure and osmolality between the two fluids. Table 1 shows the concentrations of common ions in millimoles for both blood plasma and brain ECF.

TABLE 1

Common ions in plasma (arterial plasma) and brain extracellular fluid (CSF)

| | ARTERIAL PLASMA | | CSF | |
|---|---|---|---|---|
| | HUMAN | RAT | HUMAN | RAT |
| $Na^+$ | 150 | 148 | 147 | 152 |
| $K^+$ | 4.6 | 5.3 | 2.9 | 3.4 |
| Ca, total | 2.4 | 3.1 | 1.14 | 1.1 |
| $Ca^{2+}$, free pCa | 1.4 | 1.5 | 1.0 | 1.0 |
| Mg, total | 0.86 | 0.8 | 1.15 | 1.3 |
| $Mg^{2+}$, free | 0.47 | 0.44 | 0.7 | 0.88 |
| $H^+$ | 0.000039 | 0.000032 | 0.000047 | 0.00005 |
| pH | 7.41 | 7.5 | 7.3 | 7.3 |
| $Cl^-$ | 99 | | 119 | |
| $HCO_3^-$ | 26.8 | 31 | 23.3 | 28 |

Brain ECF also contains significantly more lactate than blood plasma and significantly less glucose than blood plasma (Abi-Saab et al., "Striking Differences in Glucose and Lactate Levels Between Brain Extracellular Fluid and Plasma in Conscious Human Subjects: Effects of Hyperglycemia and Hypoglycemia," Journal of Cerebral Blood Flow & Metabolism, vol. 22, pages 271-279, 2002).

Thus, there are several physiological conditions that are different between the two sides of the BBB, such as pH, concentrations of various substances (such as lactose, glucose, K+, Mg2+), osmotic pressure and osmolality. For the physiological condition of pH, human blood plasma has a higher pH than human brain ECF. For the physiological condition of K+ concentration, brain ECF has a lower K+ concentration than human blood plasma. For the physiological condition of Mg2+ concentration, the human brain ECF has significantly more Mg2+ than human blood plasma. For the physiological condition of osmotic pressure, the human brain ECF has an osmotic pressure that is different from that of human blood plasma. In some embodiments, the physiological conditions of brain ECF may be the composition, pH, osmotic pressure and osmolality of brain ECF of patients with a particular neurological disorder, which may be different from the physiological condition of the brain ECF of the general population.

The present invention thus provides a method for evolving a DNA that encodes a template antibody against a BBB-R to create a mutant DNA library. The mutant DNA library is then expressed to obtain mutant antibodies. The mutant antibodies are screened for a conditionally active antibody that has binds to the BBB-R under at least one blood plasma physiological condition and has a low or no affinity to the BBB-R under at least one brain physiological condition in the brain ECF compared to the template antibody. Thus, the selected mutant antibody has a low or high affinity to the BBB-R at the blood plasma side and a low or no affinity to the BBB-R at the brain ECF side. This selected mutant antibody is useful as a conditionally active antibody for transport across the BBB.

Such a conditionally active antibody is advantageous for crossing the BBB and remaining in the brain ECF. The low affinity to the BBB-R at the brain side lowers the rate (or removes) the conditionally active antibody is transported back across the BBB out of the brain and back into the blood relative to the template antibody.

In some other embodiments, the present invention provides a method for evolving a DNA that encodes a template antibody against a BBB-R to create a mutant DNA library. The mutant DNA library is then expressed to obtain mutant antibodies. The mutant antibodies are screened for a conditionally active antibody that binds to the BBB-R under at least one blood plasma physiological condition and little or no affinity to the BBB-R under at least one brain physiological condition. Thus, the selected mutant antibody has affinity to the BBB-R at the plasma side and little or no affinity to the BBB-R at the brain ECF side. This selected mutant antibody is a conditionally active antibody.

Such a conditionally active antibody is advantageous in crossing the BBB and remaining in the brain ECF. After binding to the BBB-R at the blood plasma side, the conditionally active antibody is transported across the BBB, and the little to no affinity to the BBB-R at the brain ECF side means that the conditionally active antibody is unlikely to be transported out of the brain.

The affinity of the conditionally active antibody to a BBB-R may be measured by its half maximal inhibitory concentration (IC50), which is a measure of how much of the antibody is needed to inhibit the binding of a known BBB-R ligand to the BBB-R by 50%. A common approach is to perform a competitive binding assay, such as competitive ELISA assay. An exemplary competitive ELISA assay to measure IC50 on TfR (a BBB-R) is one in which increasing concentrations of anti-TfR antibody compete against biotinylated $TfR^A$ for binding to TfR. The anti-TfR antibody competitive ELISA may be performed in Maxisorp plates (Neptune, N.J.) coated with 2.5 ng/ml of purified murine TfR extracellular domain in PBS at 4° C. overnight. Plates are washed with PBS/0.05% Tween 20 and blocked using Superblock blocking buffer in PBS (Thermo Scientific, Hudson, N.H.). A titration of each individual anti-TfR antibody (1:3 serial dilution) is combined with biotinylated anti-$TfR^A$ (0.5 nM final concentration) and added to the plate for 1 hour at room temperature. Plates are washed with PBS/0.05% Tween 20, and HRP-streptavidin (Southern Biotech, Birmingham) is added to the plate and incubated for 1 hour at room temperature. Plates are washed with PBS/0.05% Tween 20, and biotinylated anti-$TfR^A$ bound to the plate is detected using TMB substrate (BioFX Laboratories, Owings Mills).

A high IC50 indicates that more of the conditionally active antibody is required to inhibit binding of the known ligand of a BBB-R, and thus that the antibody's affinity for that BBB-R is relatively low. Conversely, a low IC50 indicates that less of the conditionally active antibody is required to inhibit binding of the known ligand, and thus that the antibody's affinity for that BBB-R is relatively high.

In some embodiments, the IC50 of the conditionally active antibodies from a BBB-R in the blood plasma may be from about 1 nM to about 100 μM, or from about 5 nM to about 100 μM, or from about 50 nM to about 100 μM, or from about 100 nM to about 100 μM, or from about 5 nM to about 10 μM, or from about 30 nM to about 1 μM, or from about 50 nM to about 1 μM.

Conditionally Active Biologic Proteins for Synovial Fluid

Joint diseases are a major cause of disability and early retirement in the industrialized countries. Joint diseases often lead to damage at a joint which is difficult to repair. Synovial fluid is a body fluid that is found in the synovial cavity of the joints (e.g., knee, hip, shoulder) of a human or animal body between the cartilage and synovium of facing articulating surfaces. Synovial fluid provides nourishment to the cartilage and also serves as a lubricant for the joints. The cells of the cartilage and synovium secrete fluid that serve as a lubricant between the articulating surfaces. Human synovial fluid includes approximately 85% water. It is derived from the dialysate of blood plasma, which itself is made up of water, dissolved proteins, glucose, clotting factors, mineral ions, hormones, etc. Proteins such as albumin and globulins are present in synovial fluid and are believed to play an important role in the lubricating the joint area. Some other proteins are also found in human synovial fluid, including the glycoproteins such as alpha-1-acid glycoprotein (AGP), alpha-1-antitrypsin (AlAT) and lubricin.

Synovial fluid has a composition that is very different from other parts of the body. Thus, synovial fluid has physiological conditions that are different from other parts of the body, such as the blood plasma. For example, synovial fluid has less than about 10 mg/dL of glucose whereas the mean normal glucose level in human blood plasma is about 100 mg/dL, fluctuating within a range between 70 and 100 mg/dL throughout the day. In addition, the total protein level in the synovial fluid is about one third of the blood plasma protein level since large molecules such as proteins do not easily pass through the synovial membrane into the synovial fluid. It has also been found that the pH of human synovial fluid is higher than the pH in human plasma (Jebens et al., "On the viscosity and pH of synovial fluid and the pH of blood," The Journal of Bone and Joint Surgery, vol. 41 B, pages 388-400, 1959; Farr et al., "Significance of the hydrogen ion concentration in synovial fluid in Rheumatoid Arthritis," Clinical and Experimental Rheumatology, vol. 3, pages 99-104, 1985).

Thus, the synovial fluid has several physiological conditions that are different from those of the other parts of body, such as the physiological conditions in the blood plasma. The synovial fluid has a pH that is higher than other parts of the body, especially the blood plasma. The synovial fluid has a lower concentration of glucose than other parts of the body, such as blood plasma. The synovial fluid also has a lower concentration of protein than other parts of the body, such as blood plasma.

Several antibodies have been used to treat joint disease by introducing the antibodies into the synovial fluid. For example, the synovial fluid in an injured joint is known to contain many factors which have an influence on the progression of osteoarthritis (see, for example, Fernandes, et al., "The Role of Cytokines in Osteoarthritis Pathophysiology", *Biorheology*, vol. 39, pages 237-246, 2002). Cytokines, such as Interleukin-1 (IL-I) and Tumor Necrosis Factor-α (TNF-α), which are produced by activated synoviocytes, are known to upregulate matrix metalloproteinase (MMP) gene expression. Upregulation of MMP leads to degredation of the matrix and non-matrix proteins in the joints. Antibodies that neutralize cytokines may stop the progression of osteoarthritis.

Using antibodies as drug is a promising strategy for the treatment of joint diseases. For example, antibodies (such as antibody against aggrecan or aggrecanase) have been developed to treat osteoarthritis, which has by far the greatest prevalence among joint diseases (WO1993/022429A1). An antibody against acetylated high-mobility group box 1 (HMGB1) has been developed for diagnosis or treatment of joint diseases that are inflammatory, autoimmune, neurodegenerative or malignant diseases/disorders, such as arthritis. This antibody may be used to detect the acetylated form of HMGB1 in synovial fluid (WO 2011/157905A1). Another antibody (CD20 antibody) has also been developed to treat damage to connective tissue and cartilage of the joints.

However, the antigens of these antibodies are often expressed in other parts of the body carrying important physiological functions. Antibodies against these antigens, though efficacious in treating joint diseases, may also significantly interfere with the normal physiological functions of these antigens in other parts of the body. Therefore, severe side effects may be experienced by patients. It is thus desirable to develop therapeutics, such as antibodies against cytokines or other antigens that can preferentially bind to their antigens (proteins or other macromolecules) at higher affinity in the synovial fluid, while not binding or only weakly binding to the same antigens in other parts of the body in order to reduce side effects.

Such conditionally active biologic proteins may be conditionally active antibodies. In some embodiments, the present invention also provides conditionally active biologic proteins that are proteins other than antibodies. For example, a conditionally active immune regulator may be developed by the present invention for preferentially regulating the immune response in the synovial fluid, which may less or no effect on the immune response at other parts of the body.

The conditionally active biologic proteins may be conditionally active suppressors of cytokine signaling (SOCS). Many of these SOCS are involved in inhibiting the JAK-STAT signaling pathway. The conditionally active suppressors of cytokine signaling can preferentially suppress the cytokine signaling in the synovial fluid, while not or to a lesser extent suppressing the cytokine signaling in other parts of the body.

In some embodiments, the present invention provides a conditionally active biologic protein derived from a wild-type biologic protein. The conditionally active biologic protein has a lower activity under at least one physiological condition in certain parts of the body such as in blood plasma than the wild-type biologic protein, and has a higher activity than the wild-type biologic protein under at least one physiological condition in the synovial fluid. Such conditionally active biologic proteins can preferentially function in the synovial fluid, but not or to a lesser extent act upon other parts of the body. Consequently, such conditionally active biologic proteins may have reduced side effects.

In some embodiments, the conditionally active biologic proteins are antibodies against an antigen in or exposed to synovial fluid. Such antigens may be any proteins involved in immune response/inflammation in a joint disease, though the antigen is often a cytokine. The conditionally active antibody has a lower affinity to the antigen than the wild-type antibody for the same antigen under at least one physiological condition in other parts of the body (such as blood plasma), while has higher affinity for the antigen than the wild-type antibody under at least one physiological condition of synovial fluid. Such conditionally active antibodies can bind weakly or not at all to the antigen in other parts of the body, but bind, for example bind strongly and tightly or bind stronger to the antigen in synovial fluid.

Conditionally Active Biologic Proteins for Tumors

Cancer cells in a solid tumor are able to form a tumor microenvironment in their surroundings to support the growth and metastasis of the cancer cells. A tumor microenvironment is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

The tumor microenvironment is often hypoxic. As the tumor mass increases, the interior of the tumor grows farther away from existing blood supply, which leads to difficulties in fully supplying oxygen to the tumor microenvironment. The partial oxygen pressure in the tumor environment is below 5 mm Hg in more than 50% of locally advanced solid tumors, in comparison with a partial oxygen pressure at about 40 mm Hg in blood plasma. In contrast, other parts of the body are not hypoxic. The hypoxic environment leads to genetic instability, which is associated with cancer progression, via downregulating nucleotide excision repair and mismatch repair pathways. Hypoxia also causes the upregulation of hypoxia-inducible factor 1 alpha (HIF1-α), which induces angiogenesis, and is associated with poorer prognosis and the activation of genes associated with metastasis. See Weber et al., "The tumor microenvironment," *Surgical Oncology*, vol. 21, pages 172-177, 2012 and Blagosklonny, "Antiangiogenic therapy and tumor progression," *Cancer Cell*, vol. 5, pages 13-17, 2004.

In addition, tumor cells tend to rely on energy generated from lactic acid fermentation, which does not require oxygen. So tumor cells are less likely to use normal aerobic respiration that does require oxygen. A consequence of using lactic acid fermentation is that the tumor microenvironment is acidic (pH 6.5-6.9), in contrast to other parts of the body which are typically either neutral or slightly basic. For example, human blood plasma has a pH of about 7.4. See Estrella et al., "Acidity Generated by the Tumor Microenvironment Drives Local Invasion," *Cancer Research*, vol. 73, pages 1524-1535, 2013. The nutrient availability in the tumor microenvironment is also low due to the relatively high nutrient demand of the proliferating cancer cells, in comparison with cells located in other parts of the body.

Further, the tumor microenvironment also contains many distinct cell types not commonly found in other parts of the body. These cell types include endothelial cells and their precursors, pericytes, smooth muscle cells, Wbroblasts, carcinoma-associated Wbroblasts, myoWbroblasts, neutrophils, eosinophils, basophils, mast cells, T and B lymphocytes, natural killer cells and antigen presenting cells (APC) such as macrophages and dendritic cells (Lorusso et al., "The tumor microenvironment and its contribution to tumor evolution toward metastasis," *Histochem Cell Biol*, vol. 130, pages 1091-1103, 2008).

Accordingly, the tumor microenvironment has at least several physiological conditions that are different from those of other parts of body, such as the physiological conditions in blood plasma. The tumor microenvironment has a pH (acidic) that is lower than other parts of the body, especially the blood plasma (pH 7.4). The tumor microenvironment has a lower concentration of oxygen than other parts of the body, such as blood plasma. Also, the tumor microenvironment has a lower nutrient availability than other parts of the body, especially the blood plasma. The tumor microenvironment also has some distinct cell types that are not commonly found in other parts of the body, especially the blood plasma.

Some cancer drugs include antibodies that can penetrate into the tumor microenvironment and act upon the cancer cells therein. Antibody-based therapy for cancer is well established and has become one of the most successful and important strategies for treating patients with haematological malignancies and solid tumors. There is a broad array of cell surface antigens that are expressed by human cancer cells that are overexpressed, mutated or selectively expressed in cancer cells compared with normal tissues. These cell surface antigens are excellent targets for antibody cancer therapy.

Cancer cell surface antigens that may be targeted by antibodies fall into several different categories. Haematopoietic differentiation antigens are glycoproteins that are usually associated with clusters of differentiation (CD) groupings and include CD20, CD30, CD33 and CD52. Cell surface differentiation antigens are a diverse group of glycoproteins and carbohydrates that are found on the surface of both normal and tumor cells. Antigens that are involved in growth and differentiation signaling are often growth factors and growth factor receptors. Growth factors that are targets for antibodies in cancer patients include CEA2, epidermal growth factor receptor (EGFR; also known as ERBB1)12, ERBB2 (also known as HER2)13, ERBB3 (REF. 18), MET (also known as HGFR)19, insulin-like growth factor 1 receptor (IGF1R)20, ephrin receptor A3 (EPHA3)21, tumor necrosis factor (TNF)-related apoptosis-inducing ligand receptor 1 (TRAILR1; also known as TNFRSF10A), TRAILR2 (also known as TNFRSF10B) and receptor activator of nuclear factor-KB ligand (RANKL; also known as TNFSF11)22. Antigens involved in angiogenesis are usually proteins or growth factors that support the formation of new microvasculature, including vascular endothelial growth factor (VEGF), VEGF receptor (VEGFR), integrin αVβ3 and integrin α5β1 (REF. 10). Tumor stroma and the extracellular matrix are indispensable support structures for a tumor. Stromal and extracellular matrix antigens that are therapeutic targets include fibroblast activation protein (FAP) and tenascin. See Scott et al., "Antibody therapy of cancer," *Nature Reviews Cancer*, vol. 12, pages 278-287, 2012.

In addition to antibodies, other biologic proteins have also shown promise in treating cancers. Examples include tumor suppressors such as Retinoblastoma protein (pRb), p53, pVHL, APC, CD95, ST5, YPEL3, ST7, and ST14. Some proteins that induce apoptosis in cancer cells may also be introduced into tumors for shrinking the size of tumors. There are at least two mechanisms that can induce apoptosis in tumors: the tumor necrosis factor-induced mechanism and the Fas-Fas ligand-mediated mechanism. At least some of the proteins involved in either of the two apoptotic mechanisms may be introduced to tumors for treatment.

Cancer stem cells are cancer cells that have the ability to give rise to all cell types found in a particular cancer sample, and are therefore tumor-forming. They may generate tumors through the stem cell processes of self-renewal and differentiation into multiple cell types. It is believed that cancer stem cells persist in tumors as a distinct population and cause relapse and metastasis by giving rise to new tumors. Development of specific therapies targeted at cancer stem cells may improve the survival and quality of life of cancer patients, especially for sufferers of metastatic disease.

These drugs for treating tumors often interfere with normal physiological functions in other parts of the body besides tumors. For example, proteins inducing apoptosis in tumors may also induce apoptosis in some other parts of the body thus causing side effects. In embodiments where an antibody is used to treat tumors, the antigen of the antibody may also be expressed in other parts of the body where they perform normal physiological functions. For example, monoclonal antibody bevacizumab (targeting vascular endothelial growth factor) to stop tumor blood vessel growth. This antibody can also prevent blood vessel growth or repair in other parts of the body, thus causing bleeding, poor wound healing, blood clots, and kidney damage. Development of a conditionally active biologic protein that concentrates on targeting mainly or solely tumors is highly desirable for more effective tumor therapies.

In some embodiments, the present invention provides a conditionally active biologic protein generated from a wild-type biologic protein that may be a candidate for tumor treatment. The conditionally active biologic protein has lower activity under at least one physiological condition in parts of the body other than the tumor microenvironment such as blood plasma than the wild-type biologic protein, while it has higher activity under at least one physiological condition in the tumor microenvironment than the wild-type biologic protein. Such conditionally active biologic proteins can preferentially act upon cancer cells in the tumor microenvironment for treating tumors, and thus will be less likely to cause side effects. In the embodiment where the biologic protein is an antibody against an antigen on the surface of the tumor cells where the antigen is exposed to the tumor microenvironment, the conditionally active antibody has lower affinity to the antigen than the wild-type antibody in other parts of the body, e.g. a non-tumor microenvironment, while it has higher affinity to the antigen than the wild-type antibody in the tumor microenvironment. Such conditionally active antibodies can bind weakly or not at all to the antigen in other parts of the body, but have greater binding, or bind strongly and tightly, to the antigen in the tumor microenvironment.

In some embodiments, the conditionally active antibody is an antibody against an immune checkpoint protein, resulting in inhibition of the immune checkpoints. Such conditionally active antibodies have at least one of (1) an increased binding affinity to the immune checkpoint protein in a tumor microenvironment in comparison to the wild-type antibody from which the conditionally active antibody is derived, and, (2) a decreased binding affinity to the immune checkpoint protein in a non-tumor microenvironment in comparison to the wild-type antibody from which the conditionally active antibody is derived.

The immune checkpoints function as endogenous inhibitory pathways for the immune system to maintain self-tolerance and modulate the duration and extent of immune response to antigenic stimulation, i.e., foreign molecules, cells and tissues See Pardoll, *Nature Reviews Cancer*, vol. 12, pages 252-264, 2012. Inhibition of immune checkpoints by suppressing one or more checkpoint proteins can cause super-activation of the immune system, especially T-cells, thus inducing the immune system to attack tumors. Checkpoint proteins suitable for the present invention include CTLA4 and its ligands CD80 and CD86, PD1 and its ligands PDL1 and PDL2, T cell immunoglobulin and mucin protein-3 (TIM3) and its ligand GALS, B and T lymphocyte attenuator (BTLA) and its ligand HVEM (herpesvirus entry mediator), receptors such as killer cell immunoglobulin-like receptor (KIR), lymphocyte activation gene-3 (LAG3) and adenosine A2a receptor (A2aR), as well as ligands B7-H3 and B7-H4. Additional suitable immune checkpoint proteins are described in Pardoll, *Nature Reviews Cancer*, vol. 12, pages 252-264, 2012 and Nirschl & Drake, *Clin Cancer Res*, vol. 19, pages 4917-4924, 2013.

CTLA-4 and PD1 are two of the best known immune checkpoint proteins. CTLA-4 can down-regulate pathways of T-cell activation (Fong et al., *Cancer Res.* 69(2):609-615, 2009; and Weber, *Cancer Immunol. Immunother,* 58:823-830, 2009). Blockading CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80 or CD86 thereby blocking the down-regulation of the immune responses elicited by the interaction of CTLA-4 with its ligand.

The checkpoint protein PD1 is known to suppress the activity of T cells in peripheral tissues at the time of an inflammatory response to infection and to limit autoimmunity. An in vitro PD1 blockade can enhance T-cell proliferation and cytokine production in response to stimulation by specific antigen targets or by allogeneic cells in mixed lymphocyte reactions. A strong correlation between PD1 expression and reduced immune response was shown to be caused by the inhibitory function of PD1, i.e., by inducing immune checkpoints (Pardoll, *Nature Reviews Cancer,* 12: 252-264, 2012). A PD1 blockade can be accomplished by a variety of mechanisms including antibodies that bind PD1 or its ligands, PDL1 or PDL2.

Past research has discovered antibodies against several checkpoint proteins (CTLA4, PD1, PD-L1). These antibodies are effective in treating tumors by inhibiting the immune checkpoints thereby super-activating the immune system, especially the T-cells, for attacking tumors (Pardoll, *Nature Reviews Cancer*, vol. 12, pages 252-264, 2012). However, the super-activated T-cells may also attack host cells and/or tissues, resulting in collateral damage to a patient's body. Thus, therapy based on use of these known antibodies for inhibition of immune checkpoints is difficult to manage and the risk to the patient is a serious concern. For example, an FDA approved antibody against CTLA-4 carries a black box warning due to its high toxicity.

The present invention addresses the problem of collateral damage by super-activated T-cells by providing conditionally active antibodies against immune checkpoint proteins. These conditionally active antibodies preferentially activate the immune checkpoints in a tumor-microenvironment. At the same time, the immune checkpoints in the non-tumor-microenvironment(s), e.g. normal body tissue, are not inhibited or are less inhibited by the conditionally active antibodies such that in the non-tumor microenvironment the potential for collateral damage to the body is reduced. This goal is achieved by engineering the conditionally active antibody to be more active in the tumor microenvironment than in the non-tumor microenvironment.

In some embodiments, the conditionally active antibody against an immune checkpoint protein may have a ratio of binding activity to an immune checkpoint protein in the tumor-microenvironment to the binding activity to the same immune checkpoint protein in a non-tumor microenvironment of at least about 1.1, or at least about 1.2, or at least about 1.4, or at least about 1.6, or at least about 1.8, or at least about 2, or at least about 2.5, or at least about 3, or at least about 5, or at least about 7, or at least about 8, or at least about 9, or at least about 10, or at least about 15, or at least about 20. A typical assay for measuring the binding activity of an antibody is an ELISA assay.

Highly immunogenic tumors, such as malignant melanoma, are most vulnerable to a super-activated immune system achieved by immune system manipulation. Thus the conditionally active antibodies against immune checkpoint proteins may be especially effective for treating such highly immunogenic tumors. However, other types of tumors are also vulnerable to a super-activated immune system.

In some embodiments, the conditionally active antibodies against the immune checkpoint proteins may be used in combination therapy. For example, combination therapy may include a conditionally active antibody against a tumor cell surface molecule (tumor specific antigen) and a conditionally active antibody against an immune checkpoint protein. In one embodiment, both the binding activity of the conditionally active antibody to the tumor cell surface molecule and the binding activity of the conditionally active antibody to the immune checkpoint protein may reside in a single protein, i.e., a bispecific conditionally active antibody as disclosed herein. In some further embodiments, combination therapy may include a conditionally active antibody against a tumor cell surface molecule (tumor specific antigen) and two or more conditionally active antibodies against two or more different immune checkpoint proteins. In one embodiment, all of these binding activities may reside in a single protein, i.e., a multispecific antibody as disclosed herein.

Since the conditionally active antibodies are more active in a tumor microenvironment in comparison with the activity of the wild-type antibody against the same tumor cell surface molecule or checkpoint protein from which the conditionally active antibody is derived, these combination therapies can provide both an enhanced efficacy and a significant reduction in toxicity. The reduced toxicity of these conditionally active antibodies, especially the antibodies against the immune checkpoint proteins, can allow safe use of potent antibodies, such as ADC antibodies as described herein, as well as a higher dose of the antibodies.

In some embodiments, the conditionally active antibodies against the checkpoint proteins may be in a prodrug form. For example, the conditionally active antibodies may be prodrugs that have no desired drug activity before being cleaved and turned into a drug form. The prodrugs may be cleaved preferentially in a tumor-microenvironment, either because the enzyme that catalyzes such cleavage exists preferentially in the tumor-microenvironment or because the conditionally active antibodies make the cleavage site more accessible in a tumor microenvironment, in comparison with the accessibility of the cleavage site in a non-tumor microenvironment.

Conditionally Active Biologic Proteins for Stem Cell Niches, Including Tumor Stem Cells Stem cells exist in an environment called stem cell niche in the body, which constitutes a basic unit of tissue physiology, integrating signals that mediate the response of stem cells to the needs of organisms. Yet the niche may also induce pathologies by imposing aberrant functions on stem cells or other targets. The interplay between stem cells and their niches creates the dynamic system necessary for sustaining tissues, and for the ultimate design of stem-cell therapeutics (Scadden, "The stem-cell niche as an entity of action," Nature, vol. 441, pages 1075-1079, 2006). Common stem cell niches in vertebrates include the germline stem cell niche, the hematopoietic stem cell niche, the hair follicle stem cell niche, the intestinal stem cell niche, and the cardiovascular stem cell niche.

The stem cell niche is a specialized environment that is different from other parts of the body (e.g. blood plasma) (Drummond-Barbosa, "Stem Cells, Their Niches and the Systemic Environment: An Aging Network," Genetics, vol. 180, pages 1787-1797, 2008; Fuchs, "Socializing with the Neighbors: Stem Cells and Their Niche," Cell, vol. 116, pages 769-778, 2004). The stem cell niche is hypoxic where oxidative DNA damage is reduced. Direct measurements of oxygen levels have revealed that bone marrow is, in general, quite hypoxic (~1%-2% O2), in comparison to blood plasma (Keith et al., "Hypoxia-Inducible Factors, Stem Cells, and Cancer," Cell, vol. 129, pages 465-472, 2007; Mohyeldin et al., "Oxygen in Stem Cell Biology: A Critical Component of the Stem Cell Niche," Cell Stem Cell, vol. 7, pages 150-161, 2010). In addition, the stem cell niches need to have several other factors to regulate stem cell characteristics within the niches: extracellular matrix components, growth factors, cytokines, and factors of the physiochemical nature of the environment including the pH, ionic strength (e.g. $Ca^{2+}$ concentration) and metabolites.

Accordingly, the stem cell niche has at least several physiological conditions that are different from those of the other parts of body, such as the physiological conditions in the blood plasma. The stem cell niche has a lower oxygen concentration (1-2%) than other parts of the body, especially the blood plasma. Other physiological conditions for the stem cell niche including pH and ionic strength, may also be different from other parts of the body.

Stem cell therapy is an interventional strategy that introduces new adult stem cells into damaged tissue in order to treat disease or injury. This strategy depends on the ability of stem cells to self-renew and give rise to subsequent offspring with variable degrees of differentiation capacities. Stem cell therapy offers significant potential for regeneration of tissues that can potentially replace diseased and damaged areas in the body, with minimal risk of rejection and side effects. Therefore, delivering a drug (biologic protein (e.g. antibody) or chemical compound) to the stem cell niche for influencing the renewal and differentiation of stem cells is an important part of stem cell therapy.

There are several examples on how the stem cell niches influence the renewal and/or differentiation of the stem cells in mammals. The first is in the skin, where the β-1 integrin is known to be differentially expressed on primitive cells and to participate in constrained localization of a stem-cell population through interaction with matrix glycoprotein ligands. Second, in the nervous system, the absence of tenascin C alters neural stem-cell number and function in the subventricular zone. Tenascin C seems to modulate stem-cell sensitivity to fibroblast growth factor 2 (FGF2) and bone morphogenetic protein 4 (BMP4), resulting in increased stem-cell propensity. Third, another matrix protein, the Arg-Gly-Asp-containing sialoprotein, osteopontin (OPN), has now been demonstrated to contribute to haematopoietic stem cell regulation. OPN interacts with several receptors known to be on haematopoietic stem cells, CD44, and α4 and α5β1 integrins. OPN production can vary markedly, particularly with osteoblast activation. Animals deficient in OPN have an increased HS-cell number, because a lack of OPN leads to superphysiologic stem-cell expansion under stimulatory conditions. Therefore, OPN seems to serve as a constraint on haematopoietic stem cell numbers, limiting the number of stem cells under homeostatic conditions or with stimulation. See Scadden, "The stem-cell niche as an entity of action," Nature, vol. 441, pages 1075-1079, 2006.

Xie et al. "Autocrine signaling based selection of combinatorial antibodies that transdifferentiate human stem cells," *Proc Natl Acad Sci USA*, vol. 110, pages 8099-8104, 2013) discloses a method of using antibodies to influence stem cell differentiation. The antibodies are agonists for a granulocyte colony stimulating factor receptor. Unlike the natural granulocyte-colony stimulating factor that activates cells to differentiate along a predetermined pathway, the isolated agonist antibodies transdifferentiated human myeloid lineage CD34+ bone marrow cells into neural progenitors. Melidoni et al. ("Selecting antagonistic antibodies that control differentiation through inducible expression in embryonic stem cells," *Proc Natl Acad Sci USA*, vol. 110, pages 17802-17807, 2013) also discloses a method of using an antibody to interfere the interaction between FGF4 and its receptor FGFR113, therefore block the autocrine FGF4-mediated embryonic stem cell differentiation.

Knowledge of the functions of ligands/receptors in stem cell differentiation has enabled the strategy of applying biologic proteins to interfere with these ligands/receptors for the purpose of regulating or even directing stem cell differentiation. The ability to control differentiation of genetically unmodified human stem cells through the administration of antibodies into the stem cell niche can provide new ex vivo or in vivo approaches to stem cell-based therapeutics. In some embodiments, the present invention provides a conditionally active biologic protein generated from a wild-type biologic protein that is capable of entering the stem cell niches, including cancer stem cells, to regulate stem cell or tumor development. The conditionally active biologic protein has lower activity than the wild-type biologic protein under at least one physiological condition in other parts of the body, while it has higher activity than the wild-type biologic protein under at least one physiological condition in the stem cell niche, for example the cancer stem cell environment. Such conditionally active biologic proteins will be less likely to cause side effects and preferentially act in the stem cell niche to regulate renewal and differentiation of stem cells. In some embodiments, the conditionally active biologic proteins are antibodies. Such conditionally active antibodies can bind weakly or not at all to their antigens in other parts of the body, but bind strongly and tightly to the antigens in the stem cell niche.

The conditionally active biologic proteins for the synovial fluid, tumor microenvironment and stem cell niches of the present invention are generated by a method for evolving a DNA that encodes a wild-type biologic protein to create a mutant DNA library. The mutant DNA library is then expressed to obtain mutant proteins. The mutant proteins are screened for a conditionally active biologic protein that has a higher activity than the wild-type biologic protein under at least one physiological condition of a first part of the body selected from the group consisting of synovial fluid, tumor microenvironment, and stem cell niches, and has lower activity than the wild-type biologic protein under at least one physiological condition at a second part of the body that is different from the first part of the body. The second part of the body may be the blood plasma. Such selected mutant biologic proteins are conditionally active biologic proteins that have high activity in the first part of the body but low activity in the second parts of the body.

Such conditionally active biologic proteins are advantageous in lowering side effects of the wild-type protein, since the conditionally active biologic protein has lower activity in the other parts of the body where the conditionally active biologic protein is not intended to act. For instance, if the conditionally active biologic protein is intended to be introduced into the tumor microenvironment, the fact that the conditionally active biologic protein has low activity in parts of the body other than the tumor microenvironment means such conditionally active biologic protein will be less likely to interfere with normal physiological functions in parts of the body other than the tumor microenvironment. At the same time, the conditionally active biologic protein has high activity in the tumor microenvironment, which gives the conditionally active biologic protein a higher efficacy in treating tumors.

Because of the reduced side effects, the conditionally active biologic protein will allow a significantly higher dose of the protein to be safely used, in comparison with the wild-type biologic protein. This is especially beneficial for an antibody against a cytokine or a growth factor, because antibodies against the cytokine or growth factor may interfere with normal physiological functions of the cytokine or growth factor in other parts of the body. By using a conditionally active biologic protein, with reduced side effects, higher doses may be used to achieve higher efficacy.

The conditionally active biologic proteins for acting in one of a synovial fluid, tumor microenvironment, or stem cell niche can also enable new drug targets to be used. Using traditional biologic proteins as therapeutics may cause unacceptable side effects. For example, inhibition of an epidermal growth factor receptor (EGFR) can very effectively suppress tumor growth. However, a drug inhibiting EGFR will also suppress growth at the skin and gastrointestinal (GI) tract. The side effects render EGFR unsuitable as a tumor drug target. Using a conditionally active antibody that binds to EGFR at high affinity in only the tumor microenvironment, but not or at very low affinity at any other parts of the body, will significantly reduce the side effects and at the same time suppress tumor growth. In this case, EGFR may become an effective new tumor drug target by using conditionally active antibodies.

In another example, suppressing cytokines is often beneficial in repairing joint damage. However, suppressing cytokines in other parts of the body also may suppress the immune response of the body, causing an immune deficiency. Thus, cytokines in synovial fluid are not ideal targets for developing traditional antibody drugs for treatment of joint damage. However, by using conditionally active antibodies that preferentially bind to cytokines in the synovial fluid, while not or only weakly to the same cytokines in other parts of the body, the side effect of immune deficiency can be dramatically reduced. Therefore, cytokines in synovial fluid may become suitable targets for repairing joint damage by using conditionally active antibodies.

Conditionally Active Biologic Proteins for Organs/Tissues Susceptible to Inflammation In some embodiments, the conditionally active biologic proteins are designed to preferentially act in organs or tissues that are susceptible to inflammation, such as a lymph node, a tonsil, an adenoid, and a sinus. Additional organs and tissues that are susceptible to inflammation may be found in anatomy textbooks such as Gray's Anatomy by Henry Gray, $41^{st}$ edition, 2015, published by Elsevier.

These organs and tissues typically exhibit at least one aberrant condition once they are inflamed. For example, these inflamed organs and tissues may have higher osmotic pressure and/or a lower concentration of one or more ions, in comparison with, for example, the normal physiological conditions of other parts of the body such as human blood plasma. Further, there may be higher concentrations of small molecules, lactic acid, cytokines and white blood cells in such inflamed organs and tissues as compared to the normal physiological conditions of other parts of the body such as human blood plasma.

In some embodiments, the conditionally active biologic proteins may be produced by the present invention using an aberrant condition selected from one or more aberrant conditions encountered in an area of inflammation and a normal physiological condition in the human blood plasma. Such conditionally active biologic proteins would thus have a higher activity in the organs/tissues in an inflammatory state than the activity of the wild-type biologic protein and lower activity in human blood plasma than the activity of the wild-type biologic protein. Such conditionally active biologic proteins can preferentially act in an inflamed region of the body, but will have little or no activity in a region of the body that is not inflamed.

Conditionally Active Viral Particles

Viral particles have long been used as delivery vehicles for transporting proteins, nucleic acid molecules, chemical compounds or radioactive isotopes to a target cell or tissue. Viral particles that are commonly used as delivery vehicles include retoviruses, adenoviruses, lentivirus, herpes virus, and adeno-associated viruses. The viral particles recognize their target cells through a surface protein that serves as a recognition protein for specific binding to a cellular protein that serves as target protein of the target cells, often in a ligand-receptor binding system (Lentz, "The recognition event between virus and host cell receptor: a target for antiviral agents," *J. of Gen. Virol.*, vol. 71, pages 751-765, 1990). For example, the viral recognition protein may be a ligand for a receptor on the target cells. The specificity between a ligand and a receptor allows the viral particles to specifically recognize and deliver their content to a target cell.

Techniques for developing artificial viral particles from wild-type viruses are well known to a person skilled in the art. Known artificial viral particles as delivery vehicles include these based on retroviruses (see, e.g., WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP 0 345 242; and WO 91/02805), alphavirus (e.g., Sindbis virus vectors, Semliki forest virus (ATCC VR-67; ATCC VR-1247), Ross River virus (ATCC VR-373; ATCC VR-1246), Venezuelan equine encephalitis virus (ATCC VR-923; ATCC VR-1250; ATCC VR 1249; ATCC VR-532)), and adeno-associated viruses (see, e.g., WO 94/12649, WO 93/03769; WO 93/19191; WO 94/28938; WO 95/11984 and WO 95/00655).

Generally, the artificial viral particles are constructed by inserting a foreign recognition protein into a virus particle, often replacing the native recognition protein by recombinant technology. The foreign recognition protein may be, for example, an antibody, a receptor, a ligand or a collagen binding domain. The present invention provides a conditionally active recognition protein that is inactive or less active for binding to a cell at a normal physiological condition, and that is active or more active for binding to a cell at an aberrant condition. The conditionally active recognition protein can thereby preferentially bind to target cells of diseased tissue and/or at a disease site based on the presence of an abnormal condition at that site and avoid or only minimally bind to the cells of normal tissue where a normal physiological condition exists. The conditionally active recognition protein may be expressed and displayed on the surface of a viral particle.

In some embodiments, the present invention provides a method of evolving a wild-type recognition protein and screening for a conditionally active recognition protein. The conditionally active recognition protein is less active in binding to a cell than the wild-type recognition protein under a normal physiological condition, and more active in binding to a cell than the wild-type recognition protein under an aberrant condition. Such a conditionally active recognition protein may be inserted into a viral particle by well-known recombinant technology to generate a conditionally active viral particle.

In another embodiment, the present invention provides a conditionally active viral particle including a conditionally active recognition protein, which allows the conditionally active viral particle to recognize and bind with the target cells of diseased tissue or at a disease site, but not the cells of normal tissue. Such a conditionally active viral particle can preferentially deliver therapeutics within the viral particle to the disease tissue or disease site, while the conditionally active viral particle delivers less or does not deliver the therapeutics to the cells of normal tissue.

In some embodiments, the target cells at a disease site are inside a zone or microenvironment With an abnormal pH (e.g., pH 6.5) or an abnormal temperature, in comparison with the pH or temperature in other parts of the body that are healthy or not suffering from the particular disease or disease state. In this embodiment, the conditionally active recognition protein is less active than a wild-type recognition protein in binding with a target protein of a target cell at a normal physiological pH or temperature, and more active than a wild-type recognition protein in binding with the target protein of a target cell at an abnormal pH or temperature. In this manner, the recognition protein will preferentially bind at a site where an abnormal pH or temperature is encountered thereby delivering a treatment to the site of a disease.

In one embodiment, the viral particle may include a conditionally active antibody of the present invention, and especially the variable region of an antibody (e.g., Fab, Fab', Fv), Such a conditionally active antibody can bind to the target protein (as antigen) of a target cell with lower affinity than a wild-type antibody under a normal physiological condition which may be encountered at a location with normal tissue, and a higher affinity than the wild-type antibody under aberrant condition which may be encountered at a disease site or diseased tissue. The conditionally active antibody may be derived from the wild-type antibody according to the method of the present invention.

In an embodiment, the target protein on the target cell includes tyrosine kinase growth factor receptors which are overexpressed on the cell surfaces in, for example, many tumors. Exemplary tyrosine kinase growth factors are VEGF receptors, FGF receptors, PDGF receptors, IGF receptors, EGF receptors, TGF-alpha receptors, TGF-beta receptors, HB-EGF receptors, ErbB2 receptors, ErbB3 receptors, and ErbB4 receptors.

Conditionally Active DNA/RNA Modifying Proteins

DNA/RNA modifying proteins have been discovered as a form of new genome-engineering tools, particularly one called CRISPR, which can allow researchers to perform microsurgery on genes, precisely and easily changing a DNA sequence at exact locations on a chromosome (genome editing, Mali et al., "Cas9 as a versatile tool for engineering biology," *Nature Methods*, vol. 10, pages 957-963, 2013). For example, sickle-cell anemia is caused by a single base mutation, which can potentially be corrected using DNA/RNA modifying proteins. The technology may precisely delete or edit bits of a chromosome, even by changing a single base pair (Makarova et al., "Evolution and classification of the CRISPR-Cas systems," *Nature Reviews Microbiology*, vol. 9, pages 467-477, 2011).

Genome editing with CRISPR has the ability to quickly and simultaneously make multiple genetic changes to a cell. Many human illnesses, including heart disease, diabetes, and neurological diseases, are affected by mutations in multiple genes. This CRISPR-based technology has the potential to reverse the disease causing mutations and cure these diseases or at least reduce the severity of these diseases. Genome editing relies on CRISPR associated (Cas) proteins (a family of enzymes) for cutting the genomic DNA. Typically, the Cas protein is guided by a small guide RNA to a targeted region in the genome, where the guide RNA matches the target region. Because the Cas protein has little or no sequence specificity, the guide RNA serves as a pointer for the Cas protein to achieve precise genome editing. In one embodiment, one Cas protein may be used with multiple guide RNAs to simultaneously correct multiple gene mutations.

There are many Cas proteins. Examples include Cas1, Cas2, Cas3', Cas3", Cas4, Cas5, Cas6, Cas6e, Cas6f, Cas7, Cas8a1, Cas8a2, Cas8b, Cm8c, Cas9, Cas10, Cas10d, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4 ((Makarova et al., "Evolution and classification of the CRISPR-Cas systems," *Nature Reviews Microbiology*, vol. 9, pages 467-477, 2011).

To conduct genome editing, the Cas protein has to enter the target cell. Cells in a subject may have a different intracellular pH inside of the cells. Some cells in diseased tissue have an abnormal intracellular pH. For example, some tumor cells tend to have an alkaline intracellular pH of about 7.12-7.65, while cells in normal tissue have a neutral intracellular pH ranging from 6.99-7.20. See Cardone et al., "The role of disturbed p1-1 dynamics and the Na(+)/H(+)

exchanger in metastasis," *Nat. Rev. Cancer*, vol. 5, pages 786-795, 2005. In chronic hypoxia, the cells in diseased tissue have an intracellular pH of about 7.2-7.5, also higher than the intracellular pH of normal tissue (Rios et al., "Chronic hypoxia elevates intracellular pH and activates Na+/H+ exchange in pulmonary arterial smooth muscle cells," *American Journal of Physiology—Lung Cellular and Molecular Physiology*, vol. 289, pages L867-L874, 2005). Further, in ischemia cells, the intracellular pH is typically in a range of 6.55-6.65, which is lower than the intracellular pH of normal tissue (Haqberg, "Intracellular pH during ischemia in skeletal muscle: relationship to membrane potential, extracellular pH, tissue lactic acid and ATP," *Pflugers Arch.*, vol. 404, pages 342-347, 1985). More examples of abnormal intracellular pH in diseased tissue are discussed in Han et al., "Fluorescent Indicators for Intracellular pH," *Chem Rev.*, vol. 110, pages 2709-2728, 2010.

The present invention provides a method for producing a conditionally active Cas protein from a wild-type Cas protein, where the conditionally active Cas protein has at least one of (1) a decreased enzymatic activity relative to the activity of the wild-type Cas protein under a normal physiological condition inside a normal cell, and (2) an increased enzymatic activity relative to the activity of the wild-type Cas protein under an aberrant condition inside a target cell such as one of the diseased cells discussed above. In some embodiments, the normal physiological condition is an intracellular pH about neutral, and the aberrant condition is a different intracellular pH that is above or below neutral. In an embodiment, the aberrant condition is an intracellular pH of from 7.2 to 7.65 or an intraceullurlar pH of from 6.5-6.8.

In some embodiments, the conditionally active Cas protein may be delivered to a target cell using the conditionally active viral particle of the present invention. The conditionally active viral particle includes the conditionally active Cas protein and at least one guide RNA for directing the Cas protein to the location at which Cas protein will edit the genomic DNA.

Multispecific antibodies have high selectivity at preferentially targeting tissues containing all or most of the targets (antigens) that a multispecific antibody can bind to. For example, a bispecific antibody provides selectivity for target cells by displaying greater preference to target cells that express both of the antigens recognized by the bispecific antibody, in comparison with non-target cells that may express only one of the antigens. Therefore, due to the dynamism of the system, there are more bispecific antibodies being bound to the target cells than non-target cells at equilibrium.

The multispecific antibodies engineered herein, or their antigen-recognition fragments, may be used as the ASTR in the chimeric antigen receptor of the present invention.

Engineering Cytotoxic Cells

Once a conditionally active ASTR is identified by the screening step, the chimeric antigen receptor may be assembled by ligating the polynucleotide sequences encoding the individual domains to form a single polynucleotide sequence (the CAR gene, which encodes the conditionally active CAR). The individual domains include a conditionally active ASTR, a TM, and an ISD. In some embodiments, other domains may also be introduced in the CARs, including an ab ESD and a CSD (FIG. 1). If the conditionally active CAR is a bispecific CAR, the CAR gene may be, for example, in the following configuration in the N-terminal to C-terminal direction: N-terminal signal sequence—ASTR1-linker-ASTR2-extracellular spacer domain-transmembrane domain-co-stimulatory domain-intracellular signaling domain. In one embodiment, such a CAR gene may include two or more co-stimulatory domains.

Alternatively, the polynucleotide sequence encoding the conditionally active CAR may be in the following configuration in the N-terminal to C-terminal direction: N-terminal signal sequence—ASTR 1-linker-ASTR 2-transmembrane domain-co-stimulatory domain-intracellular signaling domain. In an embodiment, such a CAR may include two or more co-stimulatory domains. If a CAR includes more than two ASTRs, the polynucleotide sequence encoding the CAR may be in the following configuration in the N-terminal to C-terminal direction: N-terminal signal sequence-ASTR1-linker-ASTR2-linker-(antigen-specific targeting region)$_n$-transmembrane domain-co-stimulatory domain-intracellular signaling domain. Such a CAR may further include an extracellular spacer domain. Each ASTR may be separated by a linker. In an embodiment, such a CAR may include two or more co-stimulatory domains.

The conditionally active CAR is introduced into the cytotoxic cells by an expression vector. Expression vectors including a polynucleotide sequence encoding a conditionally active CAR of the invention are also provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR gene in the host cell. The adenovirus genome is a 36 kb, linear, double stranded DNA, where a foreign DNA sequence (such as CAR genes) may be inserted to substitute large pieces of adenoviral DNA in order to make the expression vector of the present invention (Grunhaus and Horwitz, "Adenoviruses as cloning vectors," *Seminars Virol.*, vol. 3, pages 237-252, 1992).

Another expression vector is based on an adeno associated virus, which takes advantage of the adenovirus coupled systems. This AAV expression vector has a high frequency of integration into the host genome. It can even infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retrovirus vector is constructed by inserting a nucleic acid (e.g., one encoding the CAR) into the viral genome at certain locations to produce a virus that is replication defective. Though the retrovirus vectors are able to infect a broad variety of cell types, integration and stable expression of the CAR gene requires the division of host cells.

Lentivirus vectors are derived from lentiviruses, which are complex retroviruses that, in addition to the common retroviral genes gag, pol, and env, contain other genes with regulatory or structural function (U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentivirus vectors have been generated by multiply attenuating the HIV virulence genes, for example, the genes env, vif, vpr, vpu and nef are deleted making the vector biologically safe. Lentivirus vectors are capable of infecting non-dividing cells and can be used for both in vivo and ex vivo gene transfer and expression of the CAR gene (U.S. Pat. No. 5,994,136).

Expression vectors including the conditionally active CAR gene can be introduced into a host cell by any means known to person skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and screened by virtue of a marker present in the vectors. Various markers that may be used include hprt, neomycin resistance, thymidine kinase, hygromycin resistance, etc. As used herein, the terms "cell," "cell line," and "cell culture" may be used interchangeably. In some embodiments, the host cell is a T cell, NK cell and NKT cell.

In another aspect, the present invention also provides genetically engineered cytotoxic cells which include and stably express the conditionally active CAR of the invention. In one embodiment, the genetically engineered cells include T-lymphocytes (T cells), naive T cells ($T_N$), memory T cells (for example, central memory T cells ($TC_M$), effector memory cells ($T_{EM}$)), natural killer cells, and macrophages capable of giving rise to therapeutically relevant progeny. In another embodiment, the genetically engineered cells are autologous cells. Examples of suitable T cells include CD4$^+$/CD8$^-$, CD4$^-$/CD8$^+$, CD4$^-$/CD8$^-$ or CD4$^+$/CD8$^+$ T cells. The T cells may be a mixed population of CD4$^+$/CD8$^-$ and CD4$^-$/CD8$^+$ cells or a population of a single clone. CD4$^+$ T cells of the invention may also produce IL-2, IFN-gamma, TNF-alpha and other T cell effector cytokines when co-cultured in vitro with cells expressing the target antigens (for example CD20$^+$ and/or CD 19$^+$ tumor cells). CD8$^+$ T cells of the invention may lyse cells expressing the target antigen. In some embodiments, T cells may be any one or more of CD45RA$^+$ CD62L$^+$ naive cells, CD45RO CD62I7 central memory cells, CD62L" effector memory cells or a combination thereof (Berger et al., "Adoptive transfer of virus-specific and tumor-specific T cell immunity," *Curr. Opin. Immunol.*, vol. 21, pages 224-232, 2009).

Genetically engineered cytotoxic cells may be produced by stably transfecting host cells with an expression vector including the CAR gene of the invention. Additional methods to genetically engineer the cytotoxic cells using the expression vector include chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells demonstrating the presence of a single integrated un-rearranged vector and expressing the conditionally active CAR may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, for example, Sambrook et al. (2001, Molecular Cloning: A Laboratory Manual, Cold Spring Harbor Laboratory, New York). Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

After the expression vector containing the CAR gene is introduced into the host cells, the CAR gene will be expressed thus producing a CAR molecule that can bind to the target antigen. The produced CAR molecule becomes a transmembrane protein by virtue of having a transmembrane domain. The host cells will then be converted to CAR cells such as CAR-T cells. The process for producing engineered cytotoxic cells with the CAR molecule, for example CAR-T cells, has been described in, for example, (Cartellieri et al., "Chimeric antigen receptor-engineered T cells for immunotherapy of cancer," *Journal of Biomedicine and Biotechnology*, vol. 2010, Article ID 956304, 2010; and Ma et al., "Versatile strategy for controlling the specificity and activity of engineered T cells," PNAS, vol. 113, E450-E458, 2016).

Whether prior to or after genetic modification of the cytotoxic cells to express a desirable conditionally active CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and US 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or au anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) and these can be used in the invention, as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

In various embodiments, the present invention provides pharmaceutical compositions including a pharmaceutically acceptable excipient and a therapeutically effective amount of the conditionally active CAR of the invention. The conditionally active CAR in the composition may be any one or more of a polynucleotide encoding the CAR, a protein including the CAR or genetically modified cells expressing the CAR protein. The CAR protein may be in the form of a pharmaceutically acceptable salt. Pharmaceutically acceptable salts refers to salts which can be used as salts of a therapeutic protein in the pharmaceutical industry, including for example, salts of sodium, potassium, calcium and the like, and amine salts of procaine, dibenzylamine, ethylenediamine, ethanolamine, methylglucamine, taurine, and the like, as well as acid addition salts such as hydrochlorides, and basic amino acids and the like.

The pharmaceutically acceptable excipient may include any excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. One type of excipient includes pharmaceutically acceptable carriers, which may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar and gelatin. The carrier may also include a sustained release material such as glyceryl monostearate or glyceryl distearate, alone or with a wax.

The pharmaceutically acceptable carriers are determined in part by the particular composition being administered, as well as by the particular method used to administer the composition. Accordingly, there are a wide variety of suitable formulations of pharmaceutical compositions of the present invention. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjustment agents and buffering agents, toxicity adjusting agents and the like, for example, sodium acetate, sodium chloride, potassium chloride, calcium chloride, sodium lactate and the like. The concentration of CAR in these formulations can vary widely, and will be selected primarily based on fluid volumes, viscosities, and body weight in accordance with the particular mode of administration selected and the patient's needs.

In various embodiments, the pharmaceutical compositions according to the invention may be formulated for delivery via any suitable route of administration. "Route of administration" may refer to any administration pathway known in the art, including but not limited to aerosol, nasal, oral, intravenous, intramuscular, intraperitoneal, inhalation, transmucosal, transdermal, parenteral, implantable pump, continuous infusion, topical application, capsules and/or injections.

The pharmaceutical compositions according to the invention can be encapsulated, tableted or prepared in an emulsion or syrup for oral administration. The pharmaceutical compositions are made following the conventional techniques of pharmacy involving milling, mixing, granulation, and compression, when necessary, for tablet forms; or milling, mixing and filling for hard gelatin capsule forms. When a liquid carrier is used, the preparation may be in the form of syrup, elixir, emulsion or an aqueous or non-aqueous suspension. Such a liquid formulation may be administered directly p.o. or filled into a soft gelatin capsule.

The pharmaceutical compositions may be formulated as: (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Particularly, suitable dosage forms include, but are not limited to, tablets, pills, powder, dragees, capsules, liquids, lozenges, gels, syrups, slurries, suspensions, etc.

The solid formulations include suitable solid excipients such as carbohydrates or protein fillers including, e.g., sugars such as lactose, sucrose, mannitol, or sorbitol; starch from corn, wheat, rice, potato, or other plants; cellulose such as methyl cellulose, hydroxypropylmethyl cellulose, and sodium carboxy-methylcellulose; and gums including arabic and tragacanth; and proteins, e.g., gelatin and collagen. Disintegrating or solubilizing agents may be added, such as cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscannellose sodium, talc, magnesium stearate, stearic acid, and other excipients, colorants, fillers, binders, diluents, buffering agents, moistening agents, preservatives, flavoring agents, dyes, disintegrating agents, and pharmaceutically acceptable carriers.

The liquid suspensions include a conditionally active CAR, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The liquid suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolality.

The lozenge forms can include the active ingredient in a flavor, usually sucrose and acacia or tragacanth, as well as pastilles including the active ingredient in an inert base, such as gelatin and glycerin or sucrose and acacia emulsions, gels, and the like containing, in addition to the active ingredient, carriers known in the art. It is recognized that the conditionally active CAR, when administered orally, must be protected from digestion. This is typically accomplished either by complexing the conditionally active CAR with a composition to render it resistant to acidic and enzymatic hydrolysis or by packaging the conditionally active CAR in an appropriately resistant carrier such as a liposome. Means of protecting proteins from digestion are well known in the art. The pharmaceutical compositions can be encapsulated, e.g., in liposomes, or in a formulation that provides for slow release of the active ingredient.

The pharmaceutical composition may be formulated as aerosol formulations (e.g., they can be "nebulized") to be administered via inhalation. Aerosol formulations can be placed into pressurized acceptable propellants, such as dichlorodifluoromethane, propane, nitrogen, and the like. Suitable formulations for rectal administration include, for example, suppositories, which consist of the packaged nucleic acid with a suppository base. Suitable suppository bases include natural or synthetic triglycerides or paraffin hydrocarbons, in addition, it is also possible to use gelatin rectal capsules which consist of a combination of the packaged nucleic acid with a base, including, for example, liquid triglycerides, polyethylene glycols, and paraffin hydrocarbons.

The pharmaceutical composition may be formulated for parenteral administration, such as, for example, by intra-articular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives, in the practice of this invention, compositions can be administered, for example, by intravenous infusion, orally, topically, intraperitoneally, intravesically or intrathecally. In one aspect, parenteral modes of administration are preferred methods of administration for compositions including the CAR protein or genetically engineered cytotoxic cells. The compositions may conveniently be administered in unit dosage form and may be prepared by any of the methods well-known in the pharmaceutical art, for example as described in Remington's Pharmaceutical Sciences, Mack Publishing Co. Easton Pa., 18$^{th}$ Ed., 1990. Formulations for intravenous administration may contain a pharmaceutically acceptable carrier such as sterile water or saline, polyalkylene glycols such as polyethylene glycol, oils of vegetable origin, hydrogenated naphthalenes and the like.

The pharmaceutical composition may be administered by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further include administering, prior to, concurrently, or after the conditionally active CAR at least one composition including an effective amount of at least one compound or protein selected from at least one of a detectable label or reporter, a TNF antagonist, an antirheumatic, a muscle relaxant, a narcotic, a non-steroid anti-inflammatory drug (NSAK)), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, or an antiproliferative agent.

The types of cancers to be treated with the genetically engineered cytotoxic cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. The cancers may be non-solid tumors (such as hematological tumors) or solid tumors. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, *Schwannoma craniopharyogioma*, ependymoma, pinealoma, hemangioblastoma, acoustic neuroma, oligodendroglioma, menangioma, neuroblastoma, retinoblastoma and brain metastases).

The present invention also provides a medical device, including at least one CAR protein, a polynucleotide sequence encoding a CAR, or a host cell expressing a CAR, wherein the device is suitable for administering the at least one conditionally active CAR by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the invention provides a kit including at least one CAR protein, a polynucleotide sequence encoding a CAR, or a host cell expressing a CAR, in lyophilized form in a first container, and an optional second container including sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of conditionally active CAR or a specified portion or variant in the first container is reconstituted to a concentration of about 0.1 mg/ml to about 500 mg/ml with the contents of the second container. In another aspect, the second container further includes an isotonic agent. In another aspect, the second container further includes a physiologically acceptable buffer. In one aspect, the disclosure provides a method of treating at least one wild-type protein mediated condition, including administering to a patient in need thereof a formulation provided in a kit and reconstituted prior to administration.

Also provided is an article of manufacture for human pharmaceutical or diagnostic use including a packaging material and a container including a solution or a lyophilized form of at least one CAR protein, polynucleotide sequence encoding a CAR, or a host cell expression a CAR. The article of manufacture can optionally include having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

In some embodiments, the present invention provides a method including retrieving cytotoxic cells from a subject, genetically engineering the cytotoxic cells by introducing a CAR gene of the present invention into the cytotoxic cells, and administering the genetically engineered cytotoxic cells to the subject. In some embodiments, the cytotoxic cells are selected from T cells, naive T cells, memory T cells, effector T cells, natural killer cells, and macrophages. In one embodiment, the cytotoxic cells are T cells.

In one embodiment, the T cells are obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from blood collected from a subject using any number of techniques known to the skilled artisan, such as Ficoll™ separation.

In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or another saline solution with or without buffer. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient or by counter-flow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. To enrich $CD4^+$ cells by negative selection, a monoclonal antibody cocktail typically includes antibodies to CD 14, CD20, CD11b, CD 16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled person would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

The obtained cytotoxic cells are then genetically engineered as described herein. A polynucleotide encoding the CAR, typically located in an expression vector, is introduced into the cytotoxic cells such that the cytotoxic cells will express, preferably stably, the CAR. The polynucleotide encoding the CAR is typically integrated into the cytotoxic cell host genome. In some embodiments, the polynucleotide introduction need not result in integration but rather only transient maintenance of the polynucleotide introduced may be sufficient. In this way, one could have a short term effect, where cytotoxic cells could be introduced into the host and then turned on after a predetermined time, for example, after the cells have been able to migrate to a particular site for treatment.

Depending upon the nature of the cytotoxic cells and the diseases to be treated, the genetically engineered cytotoxic cells may be introduced into the subject, e.g. a mammal, in a wide variety of ways. The genetically engineered cytotoxic cells may be introduced at the site of the tumor. In one embodiment, the genetically engineered cytotoxic cells navigate to the cancer or are modified to navigate to the cancer. The number of genetically engineered cytotoxic cells that are employed will depend upon a number of factors such as the circumstances, the purpose for the introduction, the lifetime of the cells, the protocol to be used. For example, the number of administrations, the ability of the cells to multiply, and the stability of the recombinant construct. The genetically engineered cytotoxic cells may be applied as a dispersion injected at or near the site of interest. The cells may be in a physiologically-acceptable medium.

It should be appreciated that the treatment method is subject to many variables, such as the cellular response to the CAR, the efficiency of expression of the CAR by the cytotoxic cells and, as appropriate, the level of secretion, the activity of the expressed CAR, the particular need of the subject, which may vary with time and circumstances, the rate of loss of the cellular activity as a result of loss of genetically engineered cytotoxic cells or the expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

The following examples are illustrative, but not limiting, of the methods of the present disclosure. Other suitable modifications and adaptations of the variety of conditions and parameters normally encountered in the field, and which are obvious to those skilled in the art, are within the scope of this disclosure.

EXAMPLES

Example 1: Generation of scFv Conditionally Active Antibodies

Figure 2:
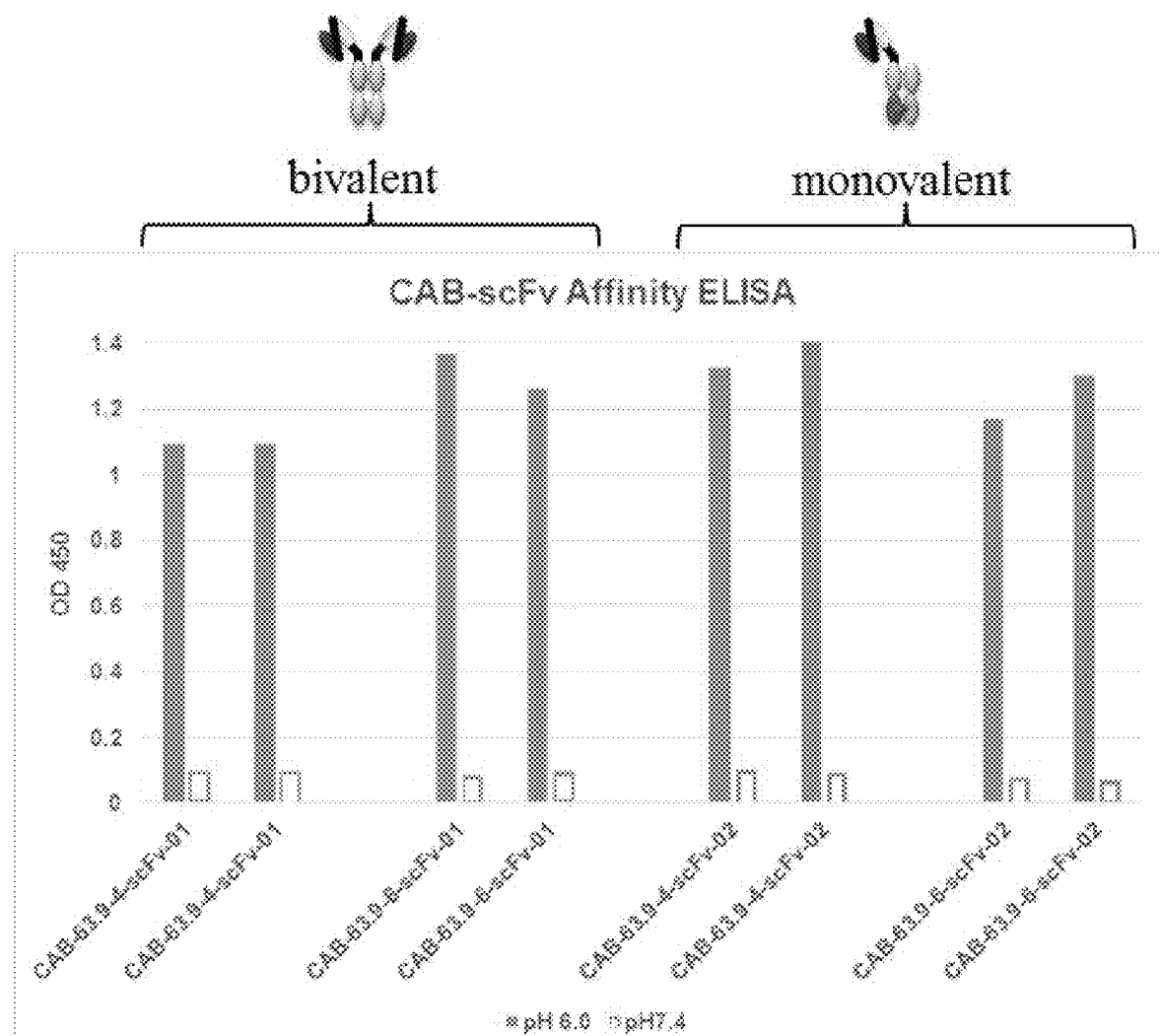
FIGS. 2 and 3 show that expressing the conditionally active antibodies of Example 1 as bivalent or monovalent antibodies does not significantly alter that selectivity of these antibodies under pH 6.0 and over pH 7.4.
Figure 3:
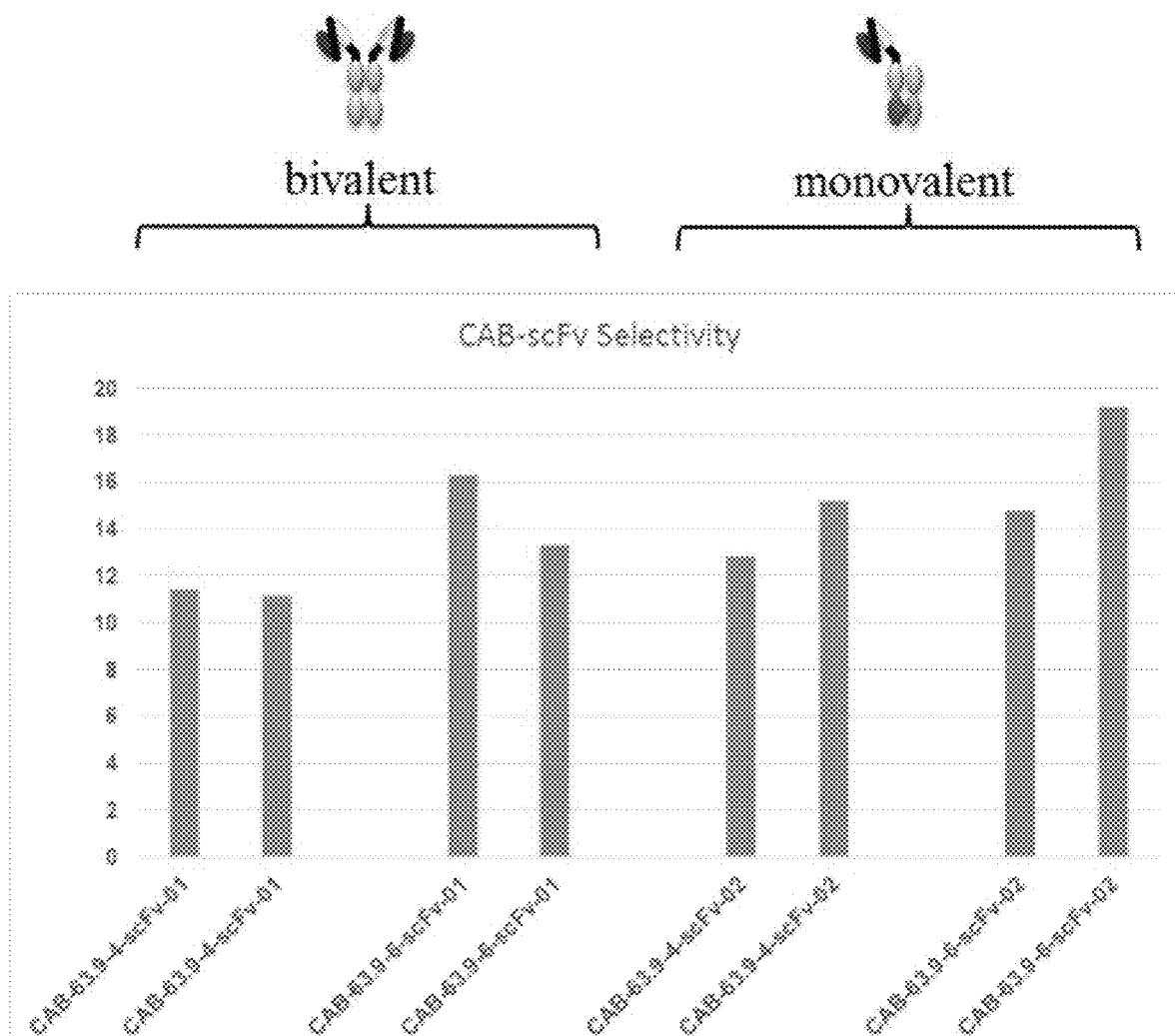

Two conditionally active antibodies (CAB-scFv-63.9-4 and CAB-scFv-63.9-6) for a drug target antigen X1 were expressed as homodimers with wild type human IgG1 Fc (resulting in bivalent antibodies CAB-scFv-63.9-4-01 and CAB-scFv-63.9-6-01 in FIGS. 2-3), as well as heterodimers in the knob-in-hole system resulting in a monovalent scFv (resulting in monovalent antibodies scFv CAB-scFv-63.9-4-02 and CAB-scFv-63.9-6-02 in FIGS. 2-3).

The binding affinities of these antibodies to the drug target antigen X1 at pH 6.0 and pH 7.4 were measured by the ELISA assay. As show in FIG. 2, the scFv antibodies showed affinities to drug target antigen X1 at both pH 6.0 and pH 7.4, which were comparable to the full bivalent antibodies. Further, the selectivity of these scFv antibodies at pH 6.0 over pH 7.4 as shown in FIG. 3 was also comparable to the full bivalent antibodies. This example demonstrated that the conditionally active antibodies of the present invention have comparable affinity and selectivity either as scFv antibodies or full bivalent antibodies. Thus, the conditionally active antibodies of the present invention may be inserted as a single DNA chain in a DNA molecule that encodes CAR in the CAR-T platform of the present invention.

Example 2: scFv Antibodies Against Target Antigen X1 for Constructing CAR-T Cells Conditionally active antibodies for the drug target antigen X1 were generated by simultaneously screening for selectivity and affinity, as well as expression level at both pH 6.0 and pH 7.4, in accordance with one embodiment of the present invention. The screening was done in serum using a FLAG tag because there were human antibodies in the serum which might cause false positives for the screening. The screening buffer was a carbonate buffer (krebs buffer with ringer—standard buffer but different from PBS). The generated conditionally active antibodies were found to have a higher affinity to the drug target antigen X1 at pH 6.0 but lower affinity to the same drug target antigen X1 at pH 7.4, both in comparison with the wild-type antibody. Further, these conditionally active antibodies all have high expression levels as shown in Table 2 below, with column "Clone" showing the antibodies and the expression level "mg/ml" being shown in the second column.

The clones of these antibodies were sent to a service provider with a requested expression level ("amount ordered", expected expression levels). However, the actual expression levels of these antibodies ("amount delivered") were very high and exceeded the expected expression levels.

TABLE 2

Conditionally active antibodies with high expression levels

| Clone | mg/ml | amount targeted | amount obtained |
|---|---|---|---|
| BAP063.6-hum10F10-FLAG | 7 | 150 | 294 |
| BAP063.6-HC-H100Y-FLAG | 6.6 | 150 | 238 |
| BAP063.8-LC046HC04-FLAG | 7 | 200 | 332.5 |
| BAP063.8-LC062HC02-FLAG | 5.8 | 200 | 220.4 |
| BAP063.9-13-1-FLAG | 5.3 | 50 | 123 |
| BAP063.9-29-2-FLAG | 4.9 | 50 | 102 |
| BAP063.9-45-2-FLAG | 5.4 | 50 | 129 |
| BAP063.9-13-3-FLAG | 5.9 | 50 | 130 |
| BAP063.9-21-3-FLAG | 5.3 | 50 | 117 |
| BAP063.9-21-4-FLAG | 7 | 50 | 176 |
| BAP063.9-29-4-FLAG | 8.2 | 50 | 196 |
| BAP063.9-48-3-FLAG | 7 | 50 | 125 |
| BAP063.9-49-4-FLAG | 5.3 | 50 | 126 |
| BAP063.9-61-1-FLAG | 5.1 | 50 | 97 |
| BAP063.9-61-2-FLAG | 5 | 50 | 92 |

Figure 4:
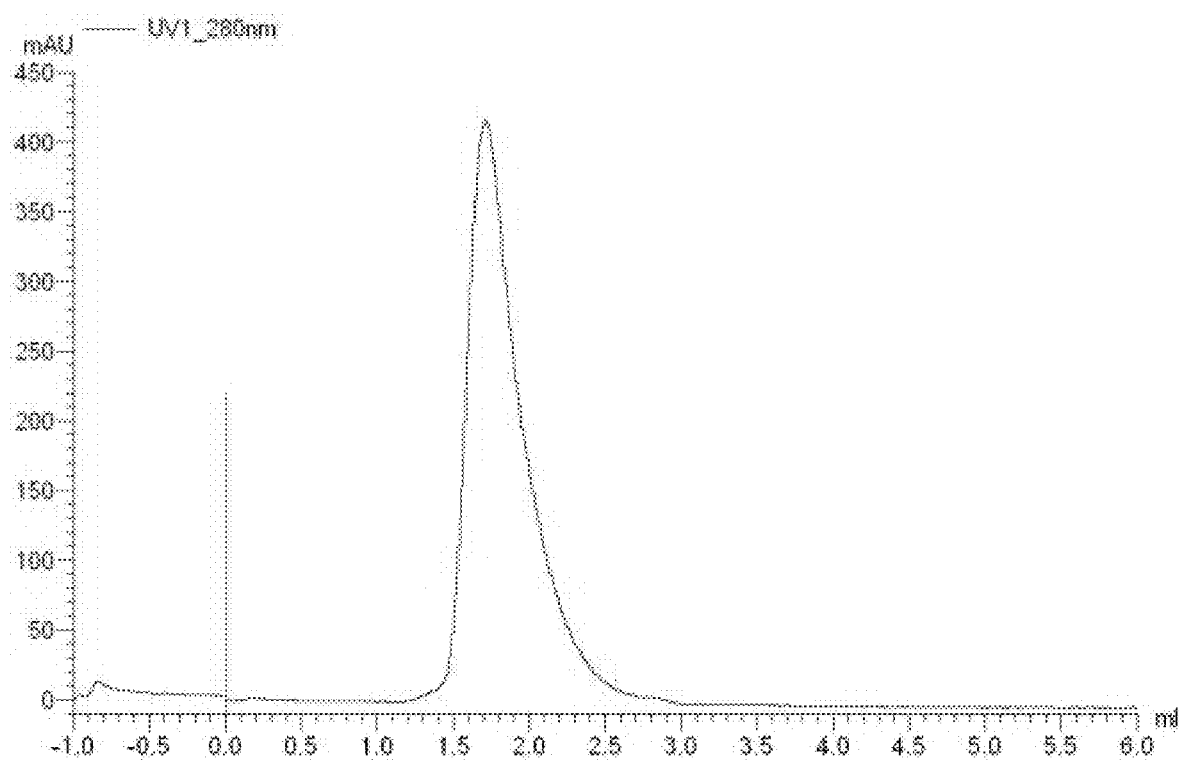
FIG. 4 is a profile of a size exclusive chromatograph indicating that the conditionally active antibodies of Example 2 do not aggregate.

The conditionally active antibodies did not show aggregation in a buffer as demonstrated in FIG. 4, using BAP063.9-13-1 antibody as an example. The BAP063.9-13-1 antibody was analyzed by size exclusion chromatography. In FIG. 4, only one peak was detected, demonstrating little or no aggregation of the antibody.

The conditionally active antibodies were also assayed using surface plasmon resonance (SPR) to measure their on and off rates to the drug target antigen X1. The SPR assay has been known to measure on and off rates for the conditionally active antibodies. The SPR assay was performed in the presence of bicarbonate. The in vivo on and off rate (in animals and humans) of the conditionally active antibodies is a very important feature for the conditionally active antibodies.

Figure 5:
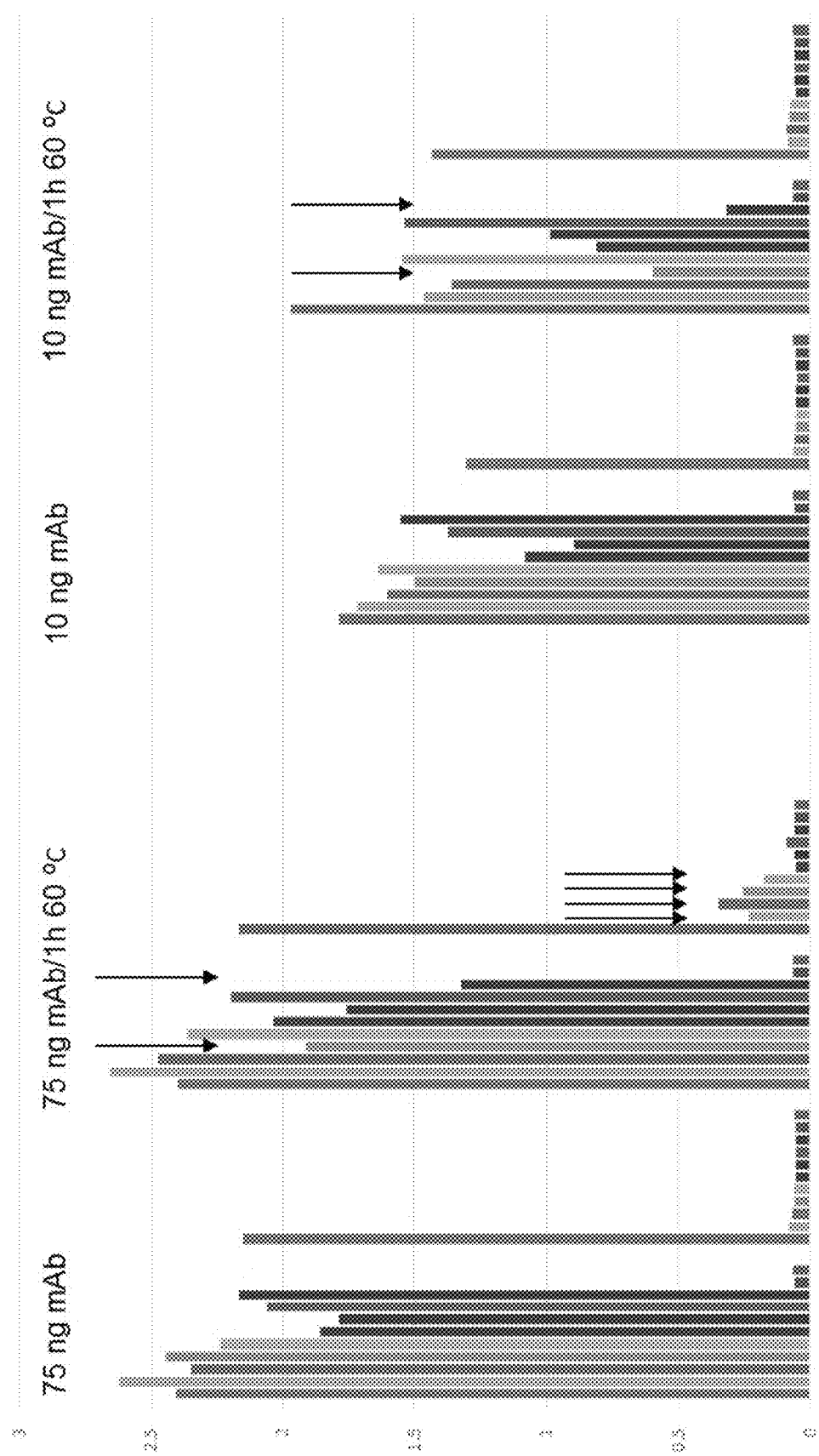
FIG. 5 shows on and off rates for the conditionally active antibodies of Example 2 as measured by a surface plasmon resonance (SPR) assay.
Figure 6A:
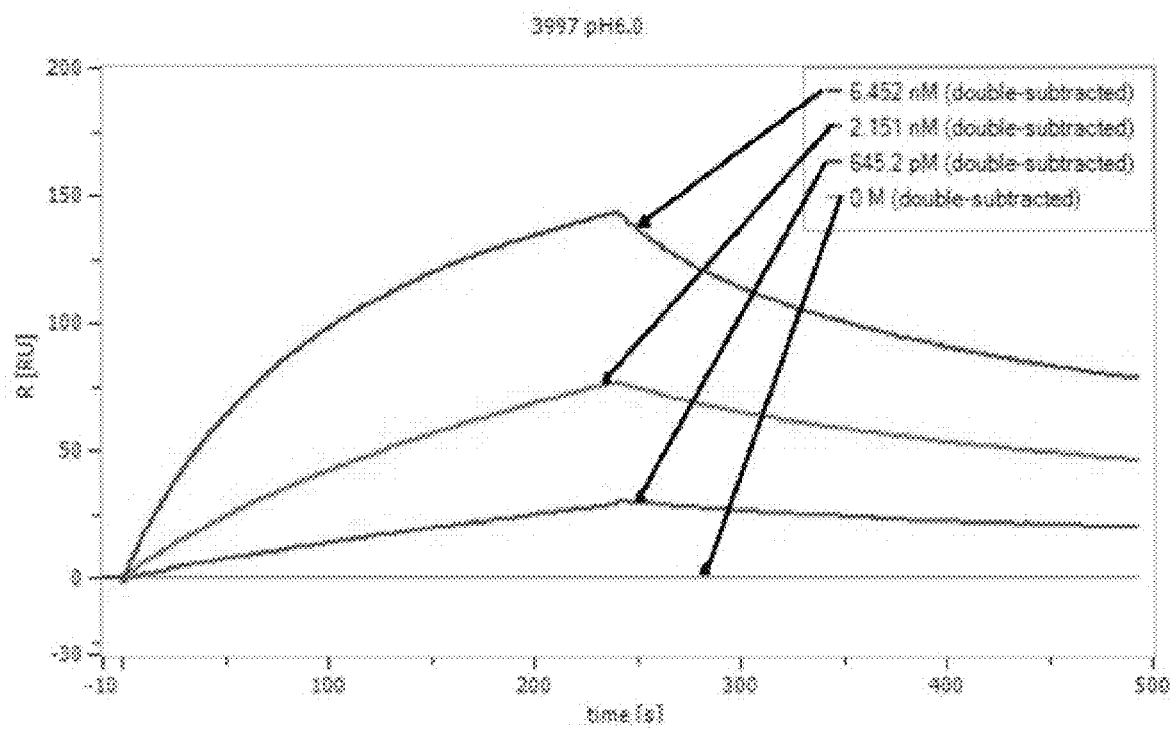
FIGS. 6A-6B show the selectivity of the conditionally active antibodies as measured by the SPR assay of Example 2.
Figure 6B:
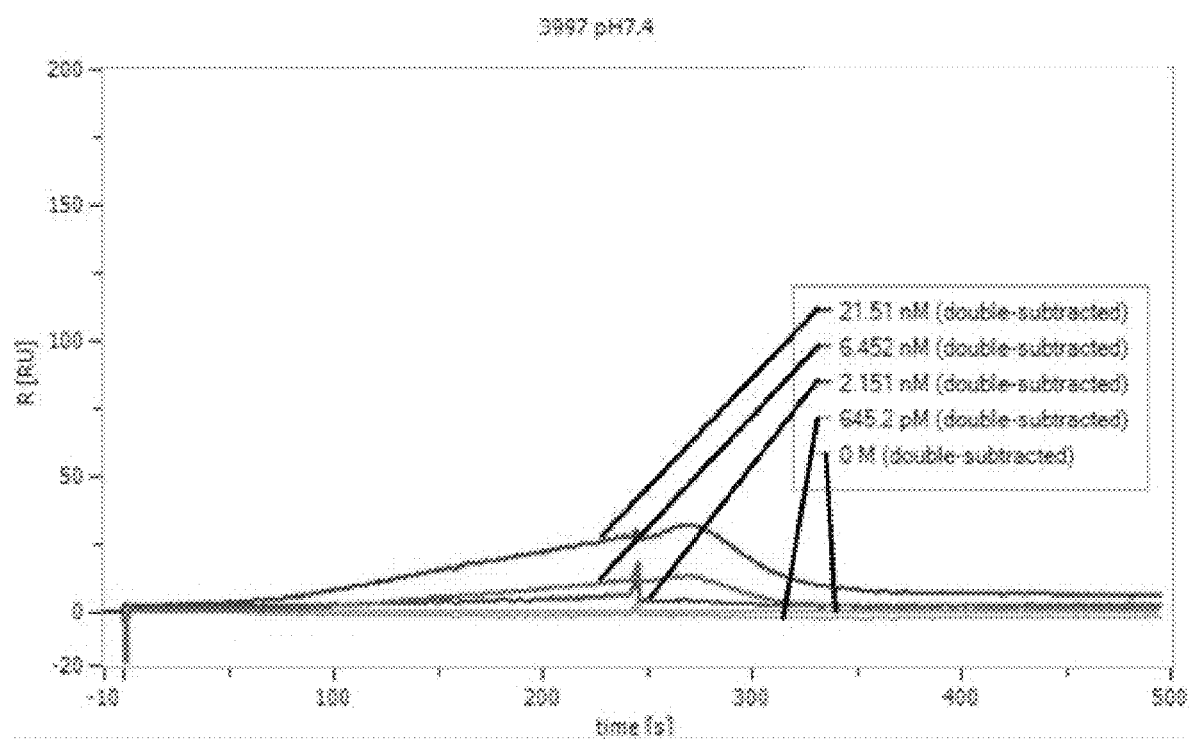

It was observed that the conditionally active antibodies have quick on-rates at pH 6.0 and slower on-rates at pH 7.4, in comparison with the negative control (BAP063 10F10 which has similar on-rates at both pH 6.0 and pH 7.4 (FIG. 5). In addition, raising the temperature from room temperature to 60° C. does not significantly alter the SPR assay results (FIG. 5). The SPR assay also showed that these conditionally active antibodies were highly selective at pH 6.0 as compared to pH 7.4 (FIGS. 6A-6B show one antibody as an example).

The conditionally active biological antibodies are summarized in Table 3. Two of the antibodies were expressed as scFv (BAP063.9-13.3 and BAP063.9-48.3), which were ready to be inserted into a CAR in the CAR-T platform. Incubating the antibodies at 60° C. for one hour did not change the affinities of most of the antibodies ("Thermostability"). In the two columns reporting data using SPR to measure binding activity at pH 6.0 and pH 7.4 (the last two columns of Table 3), a comparison was made to "BAP063.6-hum10F10-FLAG" (a negative control, second row in Table 3). The selectivity of these antibodies may be determined by the differences between the data in the two last columns. The two scFv antibodies had very high selectivity (75% and 50% at pH 6 over 0% at pH 7.4).

Figure 7A:
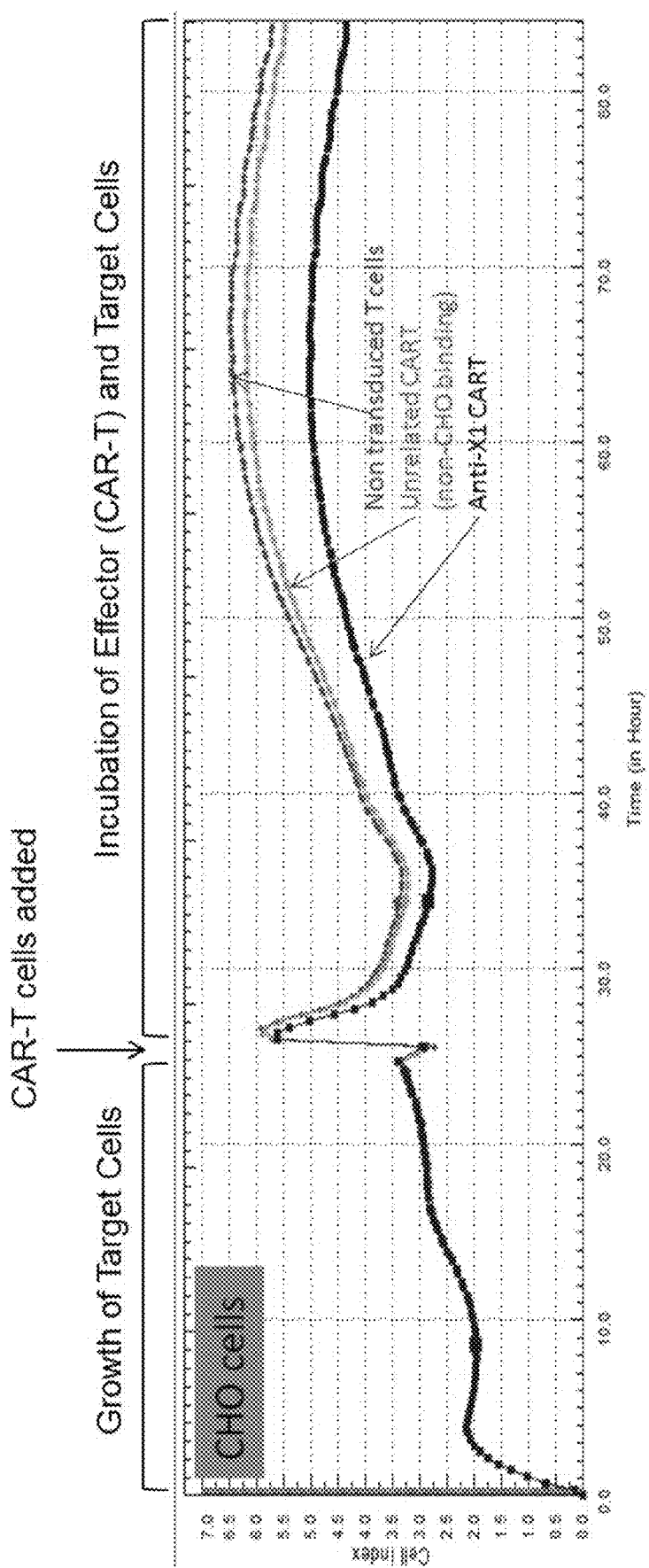
FIG. 7A shows that CAR-T cells had no effect on a population of CHO cells that do not express the target antigen X1 of the CAR-T cells. The CAR molecule in the CAR-T cells of this example included an antibody against target antigen X1, though this antibody was not conditionally active (Comparative Example A).

FIG. 7A), with a decrease in cell index indicating cytotoxicity (cell killing) by the CAR-T cells.

Referring to FIG. 7A, before addition of the T cells, the CHO cells showed growth. After addition of the CAR-T cells that bind to target antigen X1, the cell index initially decreased, indicating non-specific cytotoxicity of the T cells. However, the CHO cells resumed growing shortly thereafter. More importantly, the differences among the three treatments were insignificant, indicating no significant cytotoxicity to the CHO cells that do not express target antigen X1 of the CAR-T cells with the non-conditionally active antibody against target antigen X1.

Figure 7B:
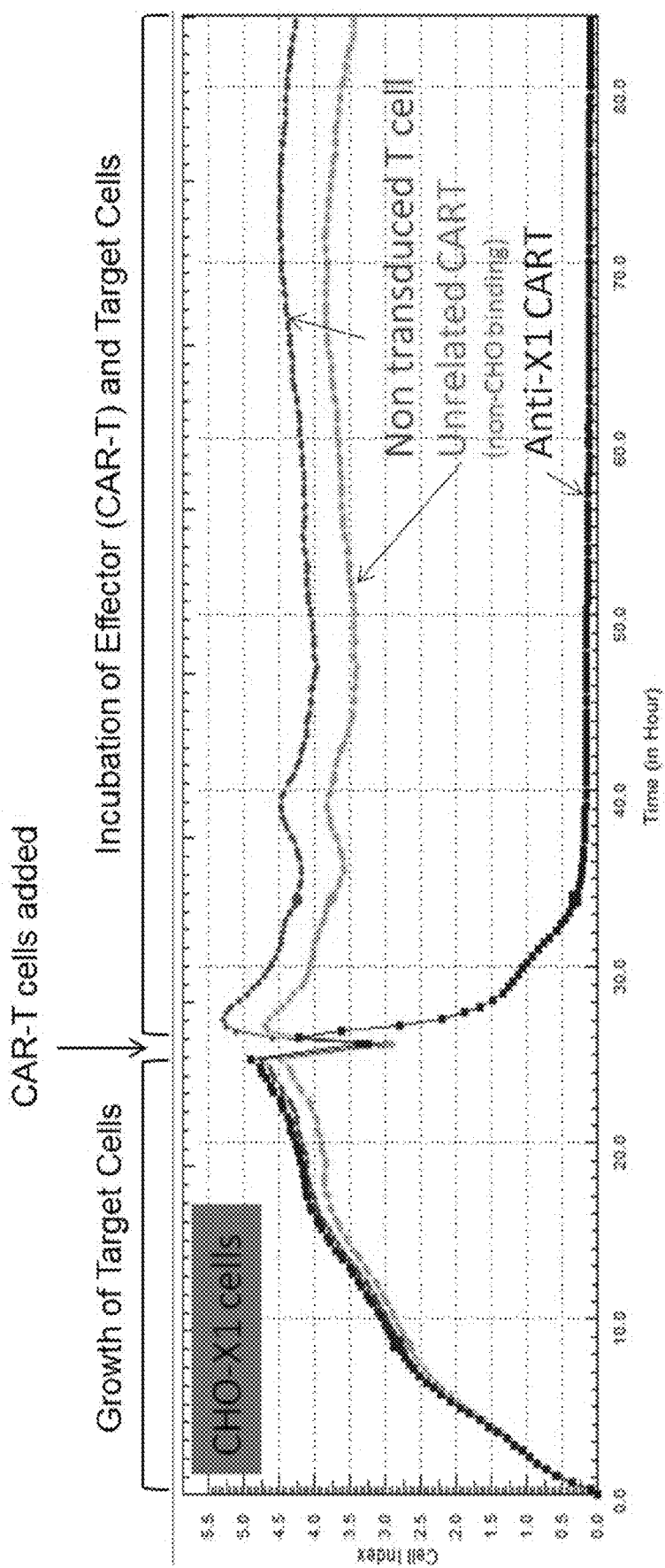
FIG. 7B shows that CAR-T cells reduced the population of CHO-63 cells that express the target antigen X1 of the CAR-T cells. These CAR-T cells are the same cells as were used to generate the data shown in FIG. 7A (Comparative Example A).

CHO cells that express target antigen X1 were then treated in the same manner as above with: (1) T cells not transduced with a CAR molecule, (2) T cells transduced with a CAR molecule that does not bind to target antigen X1, and (3) T cells transduced with a CAR molecule with a non-conditionally active antibody against target antigen X1 (FIG. 7B). After addition of the T cells, the cell index is significantly decreased by the treatment with the CAR-T cells with the non-conditionally active antibody against

TABLE 3

Summary of the conditionally active antibodies

| Clone | CAB scFv | mg/ml | amount ordered | amount delivered | Aggregation (PBS, pH 7.4) | Thermostability (1 h 60° C.) | Increased binding at pH 7.4 after heat treatment |
|---|---|---|---|---|---|---|---|
| BAP063.6-hum10F10-FLAG | | 7 | 150 | 294 | No | 100% | No |
| BAP063.6-HC-H100Y-FLAG | | 6.6 | 150 | 238 | N.D. | | |
| BAP063.9-13-1-FLAG | | 5.3 | 50 | 123 | No | 100% | Yes |
| BAP063.9-29-2-FLAG | | 4.9 | 50 | 102 | No | 100% | Yes |
| BAP063.9-45-2-FLAG | | 5.4 | 50 | 129 | No | reduced | Yes |
| BAP063.9-13-3-FLAG | Yes | 5.9 | 50 | 130 | No | 100% | Yes |
| BAP063.9-21-3-FLAG | | 5.3 | 50 | 117 | No | 100% | No |
| BAP063.9-21-4-FLAG | | 7 | 50 | 176 | No | 100% | No |
| BAP063.9-29-4-FLAG | | 8.2 | 50 | 196 | No | 100% | (yes) |
| BAP063.9-48-3-FLAG | Yes | 7 | 50 | 125 | <5% | reduced | No |

| Clone | Ka [M · s] | Kd [s$^{-1}$] | KD [M] pH 6.0 | SPR activity pH 6.0 | SPR activity pH 7.4 |
|---|---|---|---|---|---|
| BAP063.6-hum10F10-FLAG | 5.14E+06 | 8.38E−04 | 1.63E−10 | 100% | 100% |
| BAP063.6-HC-H100Y-FLAG | 2.41E+06 | 5.12E−03 | 2.12E−09 | 80% | 40% |
| BAP063.9-13-1-FLAG | 1.98E+06 | 2.88E−03 | 1.46E−09 | 100% | 75% |
| BAP063.9-29-2-FLAG | 1.19E+06 | 2.14E−03 | 1.79E−09 | 90% | 50% |
| BAP063.9-45-2-FLAG | 1.53E+06 | 2.31E−03 | 1.51E−09 | 75% | 25% |
| BAP063.9-13-3-FLAG | 1.42E+06 | 1.82E−03 | 1.28E−09 | 75% | 0% |
| BAP063.9-21-3-FLAG | 1.53E+06 | 4.13E−03 | 2.69E−09 | 50% | 25% |
| BAP063.9-21-4-FLAG | 1.03E+06 | 3.26E−03 | 3.16E−09 | 50% | 0% |
| BAP063.9-29-4-FLAG | 1.40E+06 | 2.21E−03 | 1.58E−09 | 75% | 0% |
| BAP063.9-48-3-FLAG | 8.92E+05 | 2.33E−03 | 2.61E−09 | 50% | 0% |

Comparative Example A: CAR-T Cells with Non-Conditionally Active Antibody Against Target Antigen X1

A non-conditionally active scFv antibody against target antigen X1 was used to construct CAR-T cells that bind to target antigen X1 or CHO cells expressing target antigen X1 on the cell surface (CHO-X1), FIGS. 7A-7B. The non-conditionally active antibody was used as the ASTR of the CAR molecule that was inserted into T cells to construct CAR-T cells that can bind to target antigen X1.

As a comparison, CHO cells that do not express target antigen X1 were treated with: (1) T cells not transduced with a CAR molecule, (2) T cells transduced with a CAR molecule that does not bind to target antigen X1, and (3) T cells transduced with a CAR molecule with a non-conditionally active antibody against target antigen X1 (FIG. 7A). The CHO cell population is indicated by the cell index (Y-axis in target antigen X1, but not by the other two treatments, indicating cytotoxicity to the CHO-X1 cells that express target antigen X1 by the CAR-T cells with the non-conditionally active antibody against target antigen X1.

Example 3: CAR-T Cells with a Conditionally Active scFv Antibody Against Target Antigen X1

A conditionally active scFv antibody against target antigen X1 was used to construct a CAR molecule. T cells were transduced with the CAR molecule such that the T cells expressed the CAR molecule (CAR-T cells). CHO cells expressing target antigen X1 (CHO-63 cells) or regular CHO cells that do not express target antigen X1 (CHO cells) were separately treated with the CAR-T cells. Non-transduced T-cells (without the CAR molecule) were used as a control (FIGS. 8A-8B).

Figure 8A:
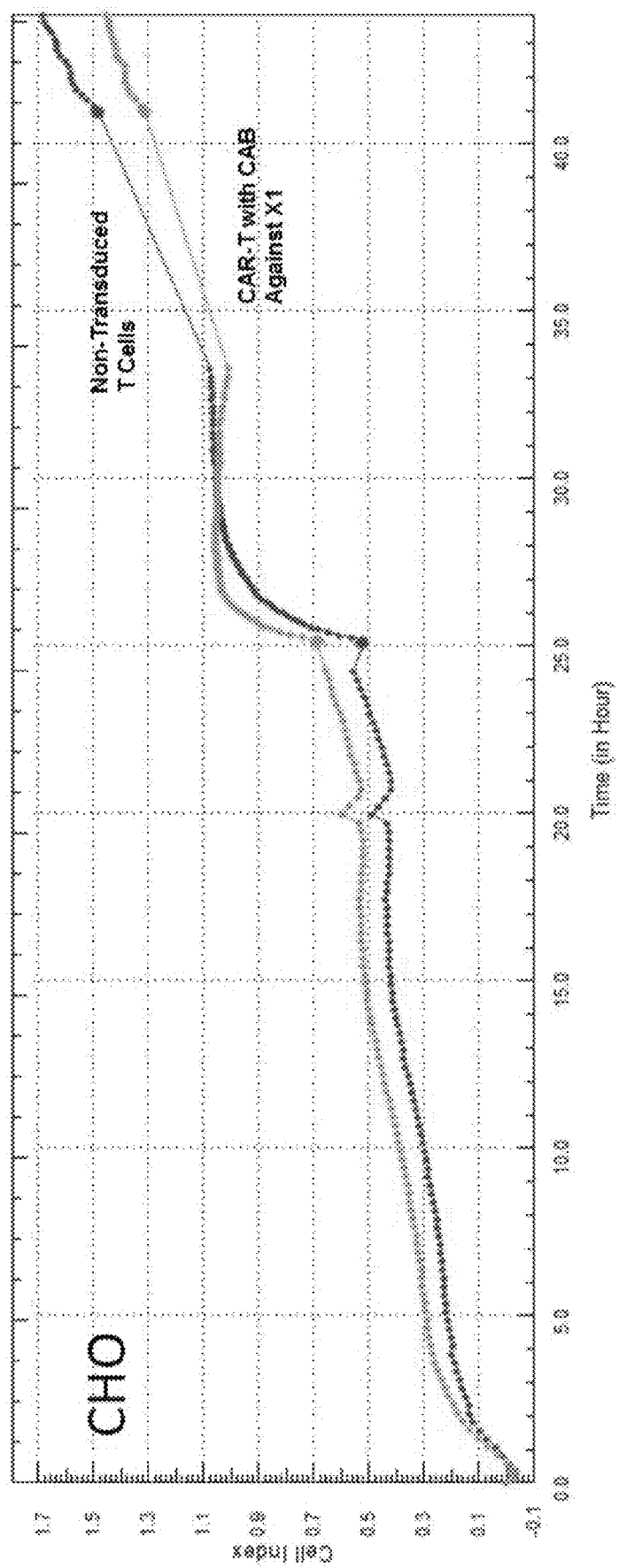
FIG. 8A shows that CAR-T cells had no effect on a population of CHO cells that do not express the target antigen X1 of the CAR-T cells. The CAR molecule in the CAR-T cells of this Example 3 included a conditionally active antibody against target antigen X1.
Figure 8B:
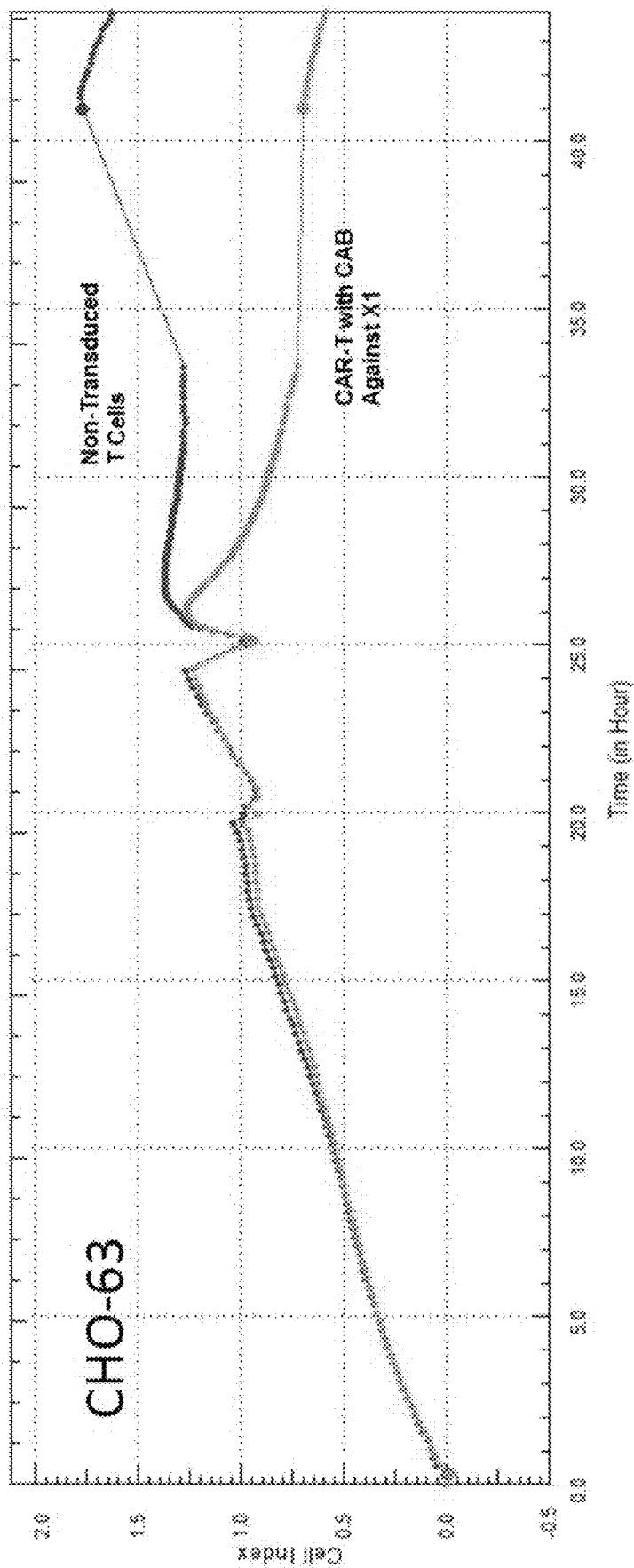
FIG. 8B shows that CAR-T cells reduced the population of CHO-63 cells that express the target antigen X1 of the CAR-T cells as tested in Example 3. These CAR-T cells are the same cells as were used to generate the data shown in FIG. 8A.

Referring to FIG. 8A, CHO cells that do not express the target antigen X1 were treated with the CAR-T cells and non-transduced T-cells. There was no significant difference between the two treatments, indicating no cytotoxicity of the CAR-T cells to the CHO cells. Referring to FIG. 8B where CHO cells expressing target antigen X1 (CHO-63) were similarly treated, the CAR-T cells with a conditionally active antibody against target antigen X1 significantly reduced the CHO-63 cell population, in comparison with non-transduced T-cells. This indicated that CAR-T cells with a conditionally active antibody against target antigen X1 were cytotoxic to the CHO-63 cells.

Figure 9A:
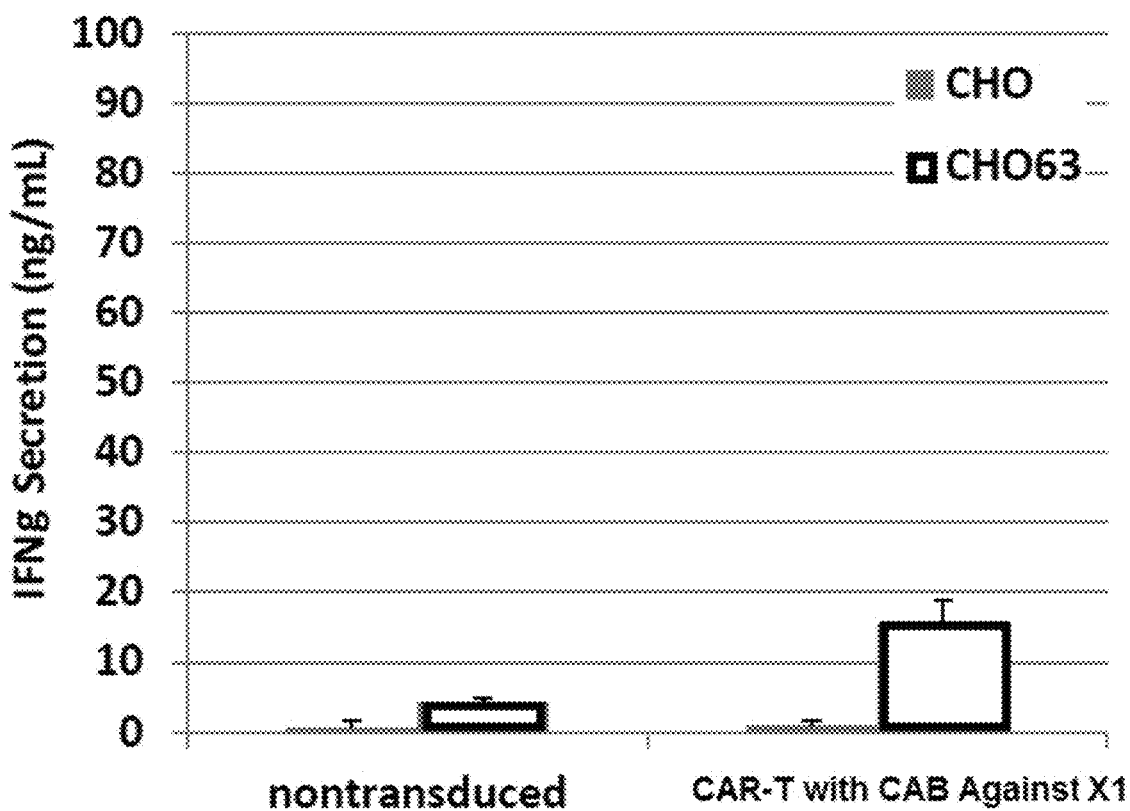
FIGS. 9A-9B show cytokine release induced by binding of CAR-T cells with the target antigen X1, as described in Example 3.
Figure 9B:
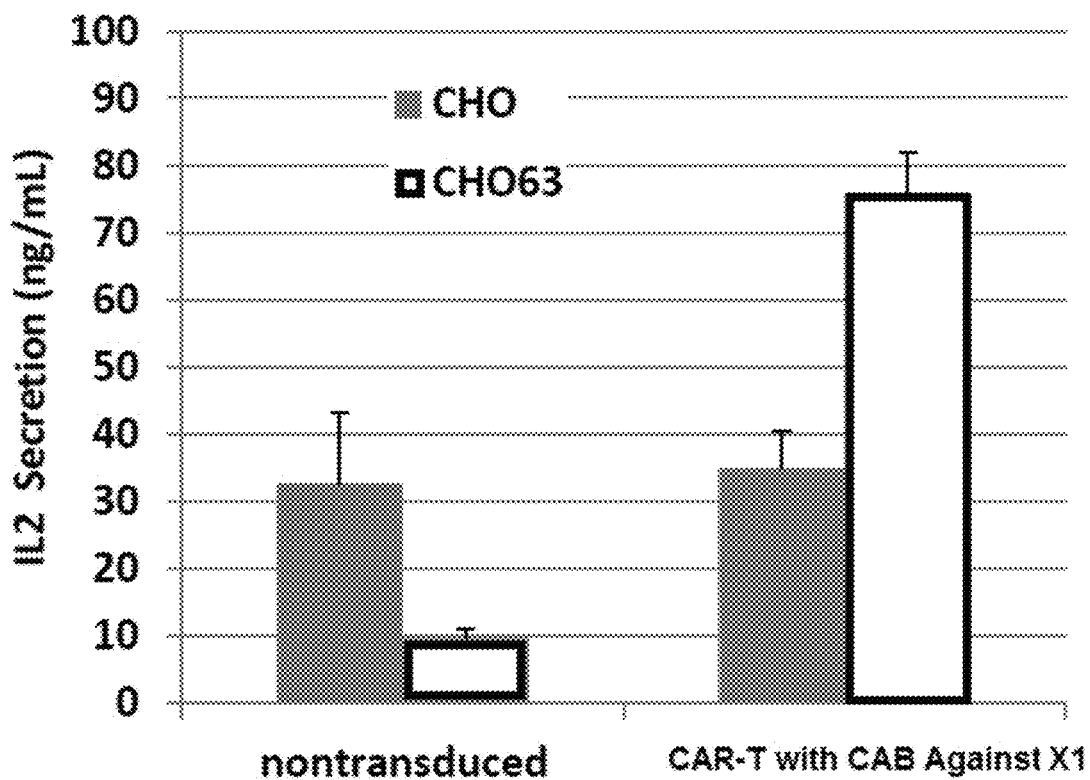

The CAR-T cells, once bound to target antigen X1, induced cytotoxicity. This effect was confirmed by measurement of the levels of the cytokines interferon gamma (INFg) and IL2. The cytokine data is shown in FIGS. 9A-9B. In FIG. 9A, the binding of CAR-T cells with target antigen X1 on the CHO-63 cells triggered significant release of INFg, in comparison with non-transduced T cells, as shown by the increased cytokine levels that were observed. Similarly, in FIG. 9B, the binding of CAR-T cells with target antigen X1 on the CHO-63 cells triggered significant release of IL2, in comparison with non-transduced T cells, as shown by the increased cytokine levels that were observed.

Example 4: CAR-T Cells with a Conditionally Active scFv Antibody Against Target Antigen X2

Conditionally active scFv antibodies against target antigen X2 were produced. Their binding activity to target antigen X2 was measured using an ELISA assay (FIG. 10).

Figure 10:
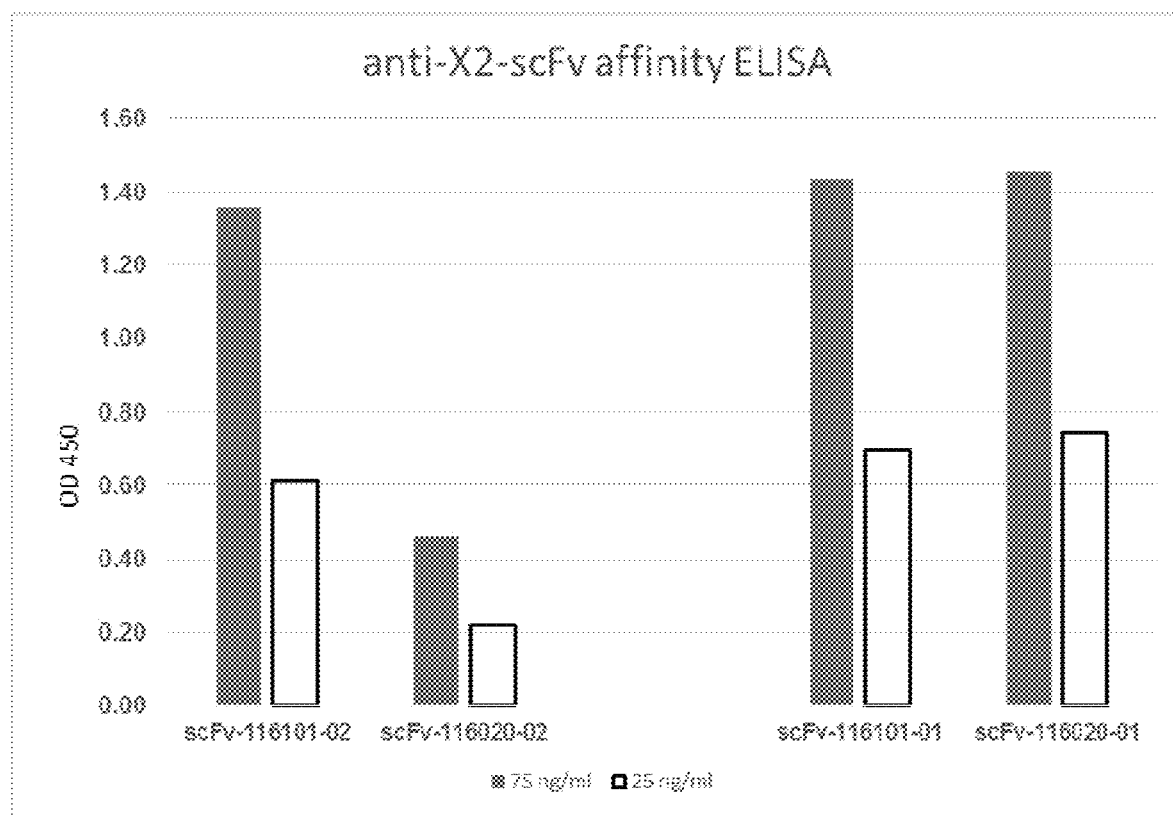
FIG. 10 shows conditionally active antibodies against target antigen X2.
Figure 11A:
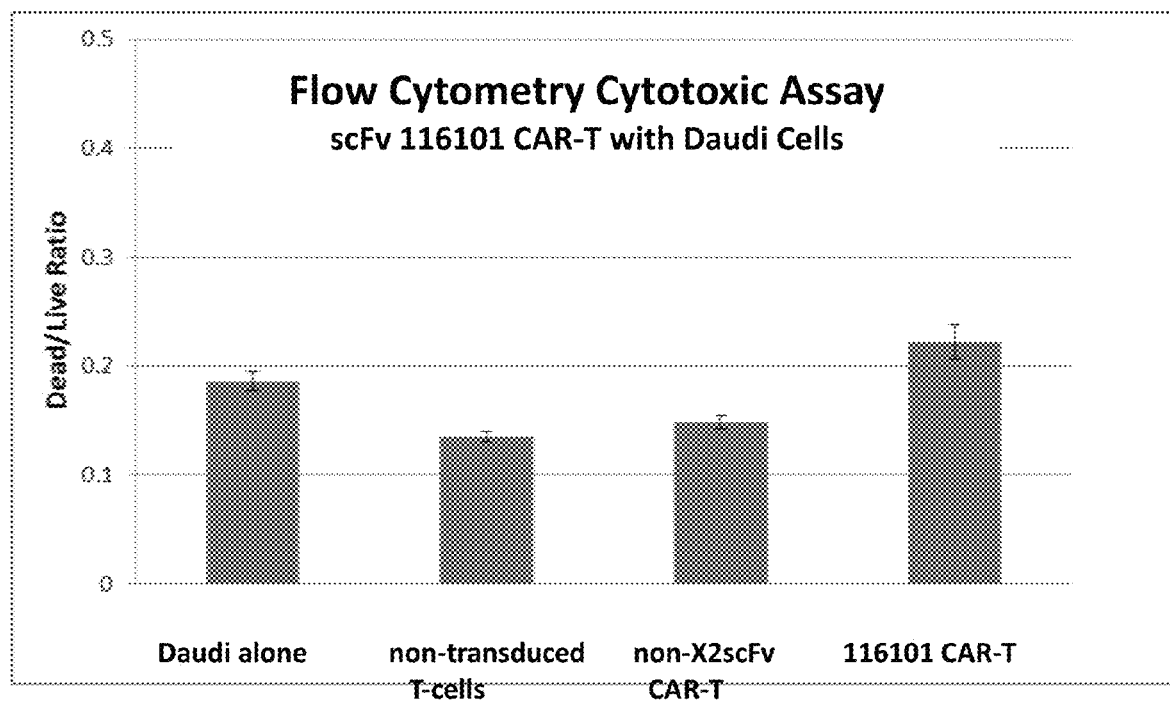
FIG. 11A shows the cytotoxic effect induced by CAR-T cells binding to Daudi cells that express target antigen X2 and the cytotoxic effect induced by CAR-T cells on HEK293 cells that do not express target antigen X2, as described in Example 4.

One of the scFv antibodies shown in FIG. 10, scFv-116101, was used to construct CAR molecules for producing CAR-T cells (116101 CAR-T). The constructed CAR-T cells were used to target Daudi cells that express target antigen X2. The negative controls were T-cells not transduced with a CAR molecule (non-transduced T cells) and CAR-T cells transduced with a CAR molecule not capable of binding to target antigen X2 (non-X2 scFv CAR-T). The results are shown in FIG. 11A. The ratio of the number of T cells to the number of Daudi cells in these treatments was 10:1. The CAR-T cells with the scFv antibody targeting target antigen X2 on the Daudi cells (116101 CAR-T) induced significant cell death for the Daudi cells as shown by the higher dead/live cell ratio in FIG. 11A.

Figure 11B:
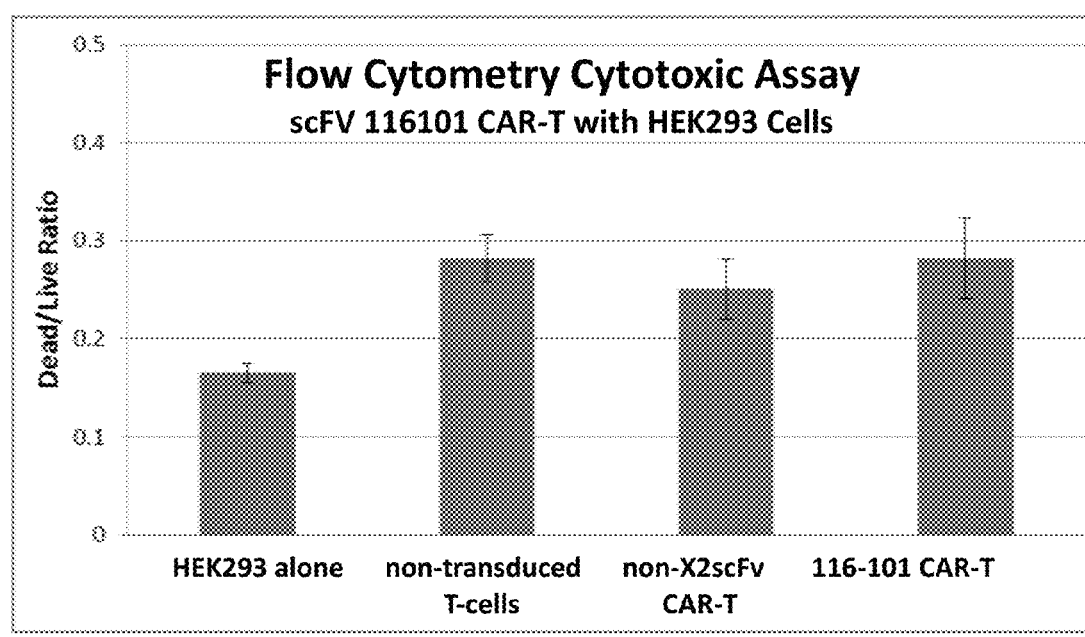
FIG. 11B shows the results of treating HEK293 cells with the same CART-T cells as were used to treat the Daudi cells, as described in Example 4. Since HEK293 cells do not express target antigen X2 on the cell surface, the CAR-T cells with the scFv antibody targeting target antigen X2 (116101 CAR-T) did not induce significant cell death in the HEK293 cells, as compared with the negative controls.

HEK293 cells were treated with the same T cells as were used to treat the Daudi cells. The results are shown in FIG. 11B. Since HEK293 cells do not express target antigen X2 on the cell surface, the CAR-T cells with the scFv antibody targeting target antigen X2 (116101 CAR-T) did not induce significant cell death in the HEK293 cells, as compared with the negative controls (FIG. 11B).

Example 5: Cytokine Release of CAR-T Cells with Antibodies Against Target Antigens X1 and X2

Figure 12A:
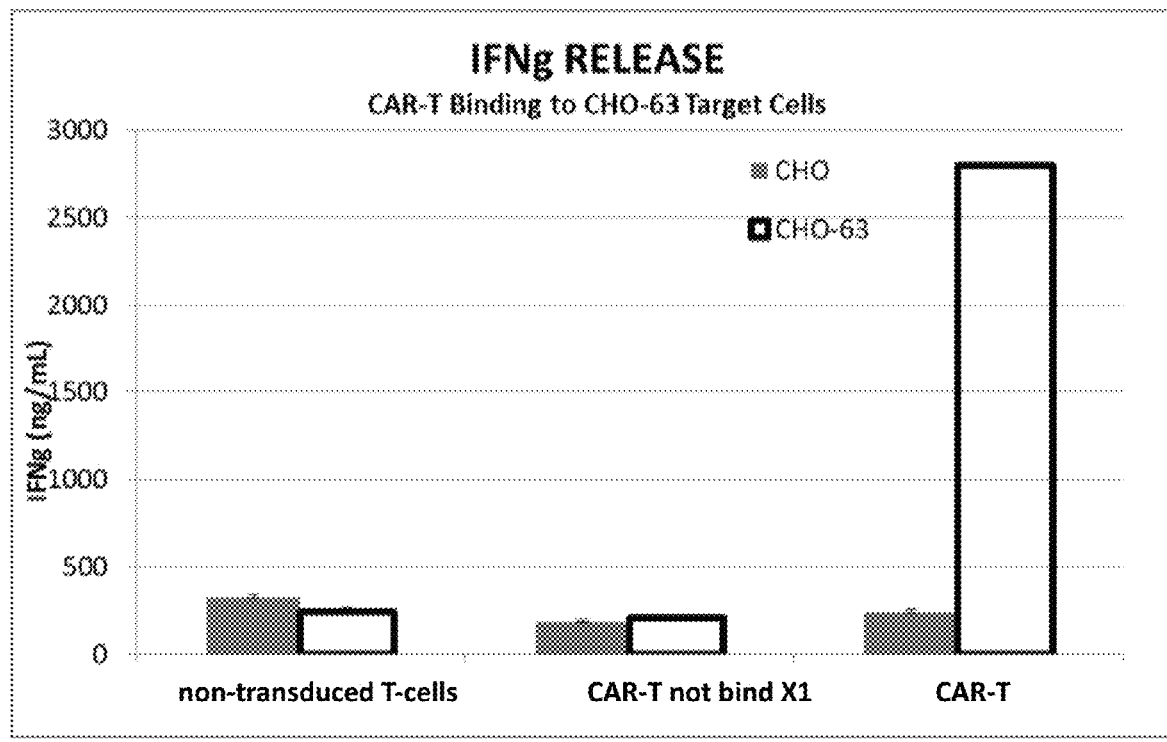
FIGS. 12A-12B show cytokine release induced by binding of CAR-T cells with the target antigen X1, as described in Example 5.
Figure 12B:
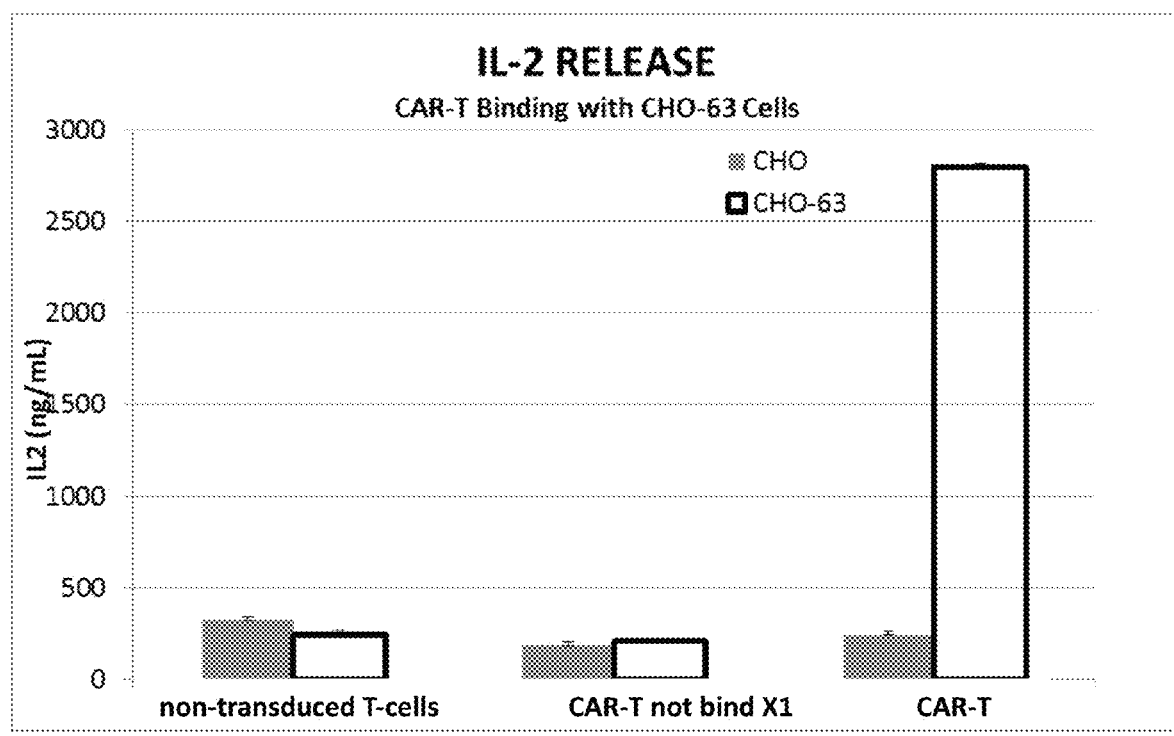

The cytokine release induced by binding of CAR-T cells with target antigens was measured in this example. FIGS. 12A-12B show INFg and IL2 release after binding of CAR-T cells containing a conditionally active scFv antibody against target antigen X1 with CHO-63 cells expressing target antigen X1. After treating the CAR-T cells with these CHO-63 cells for 24 hours, there was a significant increase both the INFg and IL2 cytokine levels indicating release of both INFg and IL2 cytokines, in comparison with controls where the same CAR-T cells were used to treat CHO cells that do not express target antigen X1. Further, T cells not transduced with a CAR molecule and CAR-T cells that did not bind with target antigen X1 did not result in significant release of INFg and IL2 cytokines.

Figure 13A:
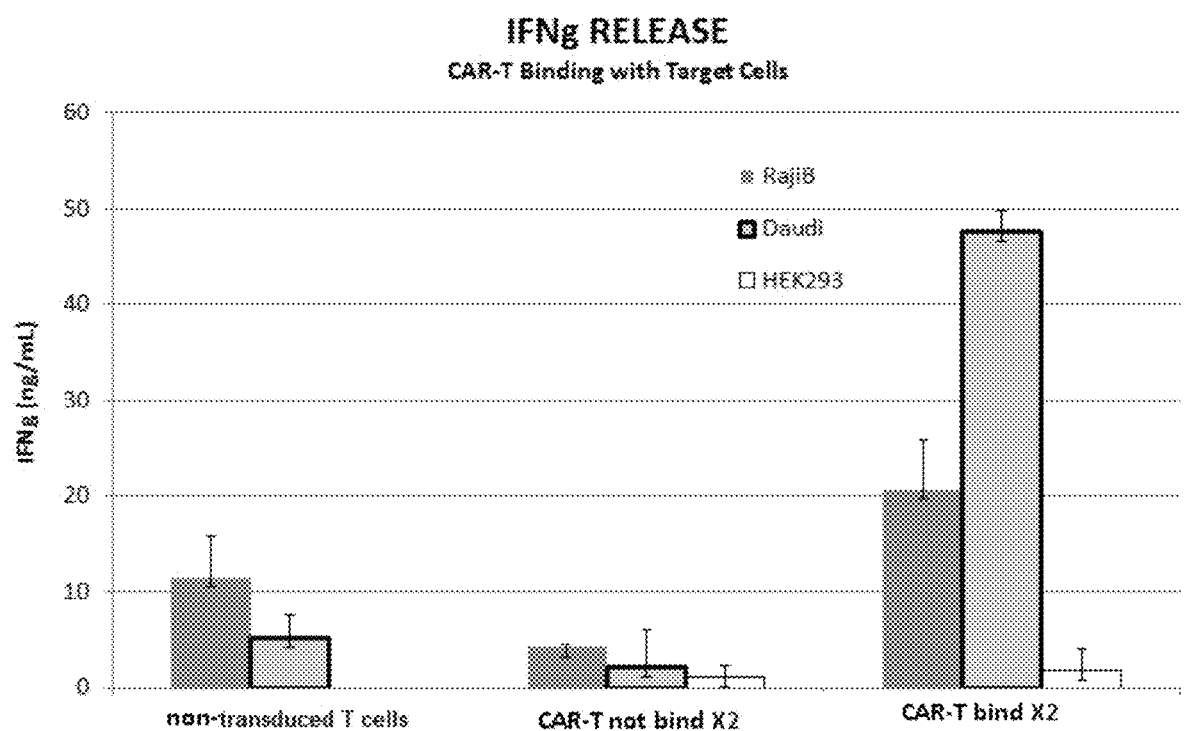
FIGS. 13A-13B show cytokine release induced by binding of CAR-T cells with the target antigen X2, as described in Example 5.
Figure 13B:
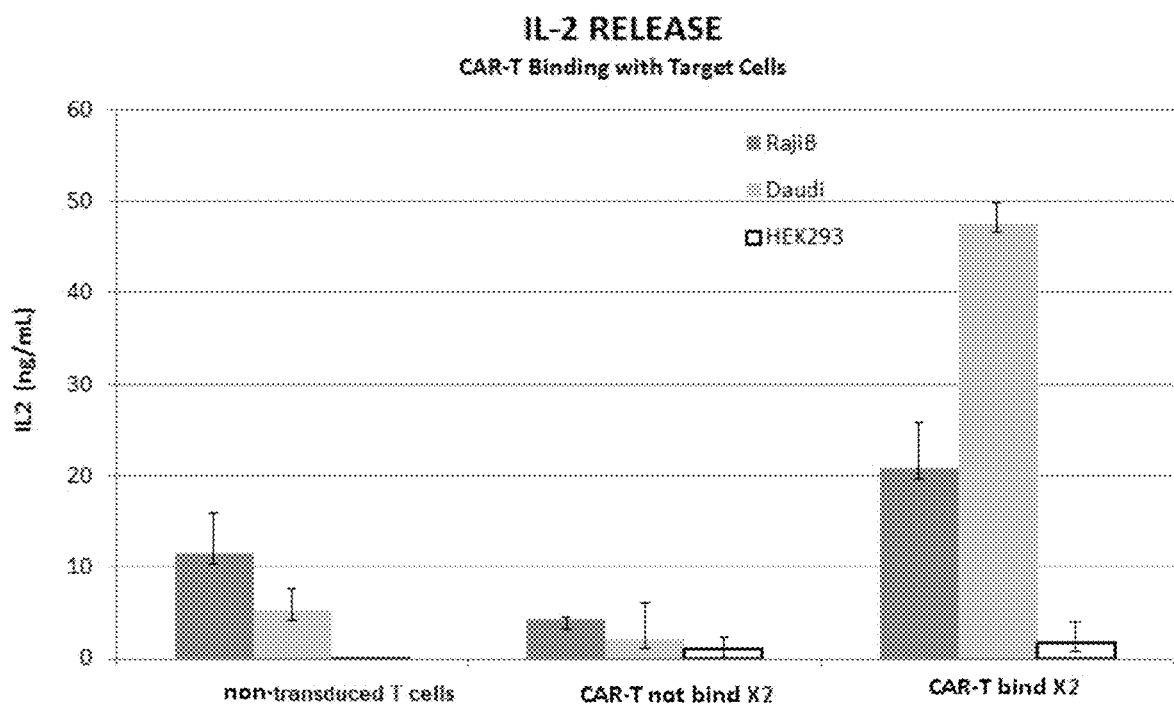
Figure 14:
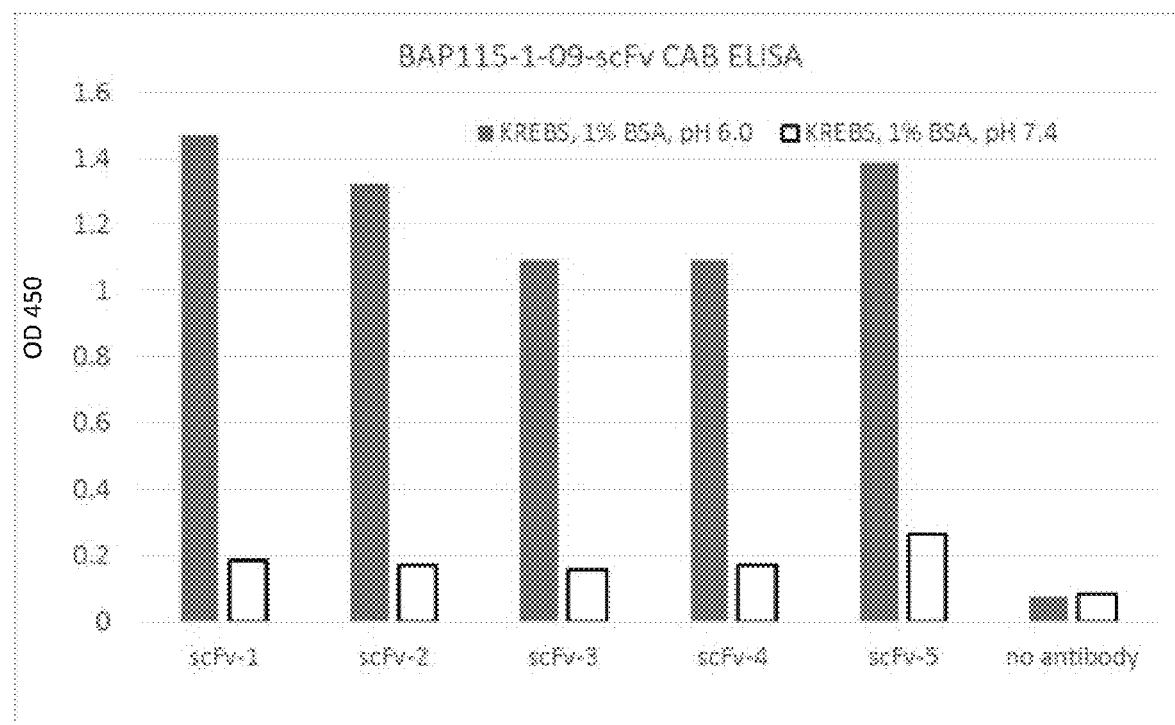
FIG. 14 shows conditionally active antibodies against target antigen X3 that are suitable for construction of CAR-T cells.

FIGS. 13A-13B show INFg and IL cytokine levels after binding of CAR-T cells containing a conditionally active scFv antibody against target antigen X2 with Rajib cells and Daudi cells both of which express target antigen X2. After treating the Rajib cells and Daudi cells with CAR-T cells for 24 hours, a significant increase in INFg and IL2 cytokine levels was observed, in comparison with controls where the same CAR-T cells were used to treat HEK293 cells that do not express target antigen X2. Further, T cells not transduced with a CAR molecule and CAR-T cells that did not bind with target antigen X2 did not significantly increase cytokine levels thereby indicating a failure to induce significant release of INFg and IL2 cytokines.

Example 6: Conditionally Active scFv Antibodies Against Target Antigen X3

Five conditionally active scFv antibodies against target antigen X3 were selected. The selected conditionally active scFv antibodies are more active at pH 6.0 than at pH 7.4. These conditionally active scFv antibodies may be used to construct CAR-T cells binding to cells expressing target antigen X3.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

What is claimed is:

1. A method for producing a chimeric antigen receptor for binding with a target antigen that is a cancer cell surface antigen tyrosine kinase growth factor receptor, said chimeric antigen receptor comprising at least one antigen specific targeting region, a transmembrane domain and an intracellular signaling domain, said method comprising the steps of generating the at least one antigen specific targeting region from a parent protein or a domain thereof that binds specifically with the target antigen that is the cancer cell surface antigen tyrosine kinase growth factor receptor, by:
  i. evolving the DNA which encodes the parent protein or a domain thereof using one or more evolutionary techniques to create mutant DNAs;
  ii. expressing the mutant DNAs to obtain mutant polypeptides;
  iii. subjecting the mutant polypeptides to an assay under a normal physiological pH in a range of 7.2-7.6 and to an assay under an aberrant pH below the normal physiological pH; and
  iv. selecting a conditionally active antigen specific targeting region from the mutant polypeptides expressed in step (iii) which exhibits a decrease in binding activity to the cancer cell surface antigen tyrosine kinase growth factor receptor in the assay at the normal physiological pH compared to a same binding activity of the mutant polypeptide to the cancer cell surface antigen tyrosine growth factor receptor in the assay under the aberrant pH; and linking the selected conditionally active antigen specific targeting region to the transmembrane domain and the intracellular signaling domain.

2. The method of claim 1, wherein the chimeric antigen receptor further comprises an extracellular spacer domain or at least one co-stimulatory domain and the linking step further comprises linking to the chimeric antigen receptor the extracellular spacer domain or the at least one co-stimulatory domain.

3. The method of claim 2, wherein the chimeric antigen receptor comprises the extracellular spacer domain and the extracellular spacer domain is selected from an Fc fragment of an antibody, a hinge region of an antibody, a CH2 region of an antibody, a CH3 region of an antibody, an artificial spacer sequence and combinations thereof.

4. The method of claim 2, wherein the chimeric antigen receptor comprises the extracellular spacer domain and further comprising as step of determining the ubiquitylation resistance of the extracellular spacer domain at the aberrant pH and the normal physiological pH and selecting the extracellular spacer domain that has an enhanced ubiquitylation-resistance level at the aberrant pH as compared to the ubiquitylation-resistance level of the extracellular spacer domain at the normal physiological pH.

5. The method of claim 1, wherein the at least one antigen specific targeting region comprises two antigen specific targeting regions that are connected with a linker.

6. The method of claim 5, wherein each of the two antigen specific targeting regions binds with a different target antigen or a different epitope of the same target antigen.

7. The method of claim 5, wherein the linker has a first conformation at the aberrant pH for the at least two antigen specific targeting regions to bind to the target antigen at a higher binding activity than a binding activity of a second conformation of the linker at the normal physiological pH.

8. The method of claim 1, wherein the at least one antigen specific targeting region is selected from an antibody, a fragment of an antibody, a divalent single chain antibody or a diabody, a ligand, a receptor binding domain of a ligand, a receptor, a ligand binding domain of a receptor, and an affibody.

9. The method of claim 1, wherein the at least one antigen specific targeting region is a multi-specific antibody.

10. The method of claim 1, wherein the transmembrane domain is selected from an artificial hydrophobic sequence and transmembrane domains of a Type I transmembrane protein, an alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, and CD154.

11. The method of claim 2, wherein the chimeric antigen receptor comprises the co-stimulatory domain and the co-stimulatory domain is selected from co-stimulatory domains of proteins in the TNFR superfamily, CD28, CD137, CD134, Dap10, CD27, CD2, CD5, ICAM-1, LFA-1, Lck, TNFR-I, TNFR-II, Fas, CD30, CD40, ICOS LIGHT, NKG2C, and B7-H3.

12. The method of claim 1, wherein the intracellular signaling domain is selected from cytoplasmic signaling domains of a human CD3 zeta chain, FcγRIII, FcεRI, a cytoplasmic tail of a Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

13. The method of claim 1, wherein the aberrant pH is present in a location selected from a tumor microenvironment, a brain extracellular fluid, a stem cell niche, a lymph node, a tonsil, an adenoid, a sinus, and a synovial fluid.

14. The method of claim 13, wherein the aberrant pH is present in a tumor microenvironment.

* * * * *

UNITED STATES PATENT AND TRADEMARK OFFICE
CERTIFICATE OF CORRECTION

| | | |
|---|---|---|
| PATENT NO. | : 11,584,927 B2 | Page 1 of 1 |
| APPLICATION NO. | : 16/053166 | |
| DATED | : February 21, 2023 | |
| INVENTOR(S) | : Short | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1170 days.

Signed and Sealed this
Fourteenth Day of January, 2025

Derrick Brent
*Acting Director of the United States Patent and Trademark Office*